(12) United States Patent
Seleznev et al.

(10) Patent No.: US 10,451,763 B2
(45) Date of Patent: Oct. 22, 2019

(54) EVALUATION OF FORMATION UTILIZING WIDEBAND ELECTROMAGNETIC MEASUREMENTS

(71) Applicant: SCHLUMBERGER TECHNOLOGY CORPORATION, Sugar Land, TX (US)

(72) Inventors: Nikita Valentinovich Seleznev, Cambridge, MA (US); Chang-Yu Hou, Cambridge, MA (US); Denise Freed, Newton Highlands, MA (US); Ridvan Akkurt, London (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 350 days.

(21) Appl. No.: 15/336,494

(22) Filed: Oct. 27, 2016

(65) Prior Publication Data

US 2018/0120468 A1 May 3, 2018

(51) Int. Cl.
*G01V 3/20* (2006.01)
*G01N 15/08* (2006.01)
*G01N 33/24* (2006.01)

(52) U.S. Cl.
CPC ............. *G01V 3/20* (2013.01); *G01N 15/088* (2013.01); *G01N 33/24* (2013.01)

(58) Field of Classification Search
CPC ....................................................... G01V 3/20
See application file for complete search history.

(56) References Cited

U.S. PATENT DOCUMENTS

| 4,703,277 | A | * | 10/1987 | Kenyon | .................. G01V 11/00 |
| | | | | | 250/256 |
| 7,363,160 | B2 | | 4/2008 | Seleznev et al. | |
| 7,376,514 | B2 | | 5/2008 | Habashy et al. | |
| 7,863,901 | B2 | | 1/2011 | Seleznev et al. | |

(Continued)

OTHER PUBLICATIONS

Revil, Effective conductivity and permittivity of unsaturated porous materials in the frequency range 1 mHz-1GHz, Water Resources Research, vol. 49, 306-327 (Year: 2013).*

(Continued)

*Primary Examiner* — Manuel L Barbee
*Assistant Examiner* — Raymond L Nimox

(57) ABSTRACT

Methods and systems are provided for investigating a rock sample, in which wideband electromagnetic response data are obtained and processed by inversion in order to determine values for a plurality of parameters of the rock sample. The wideband electromagnetic response data is derived from electromagnetic measurements of the rock sample at frequencies that fall within a wideband of frequencies, wherein the wideband of frequencies includes a low frequency sub-band that is sensitive to conductivity of the rock sample and a high frequency sub-band that is sensitive to the permittivity of the rock sample. In one embodiment, the inversion can employ a wideband model that accounts for two different polarization mechanisms. The wideband model can be used to describe predicted electromagnetic response of the rock sample at frequencies that fall within the wideband of frequencies.

23 Claims, 42 Drawing Sheets

(56) References Cited

U.S. PATENT DOCUMENTS

| | | | |
|---|---|---|---|
| 2007/0061082 A1* | 3/2007 | Seleznev | G01V 3/26 |
| | | | 702/11 |
| 2012/0153958 A1* | 6/2012 | Anderson | G01V 3/30 |
| | | | 324/332 |
| 2015/0025807 A1* | 1/2015 | Anderson | G01V 3/30 |
| | | | 702/11 |
| 2015/0192004 A1 | 7/2015 | Saeedfar | |
| 2015/0361789 A1 | 12/2015 | Donderici et al. | |
| 2016/0139293 A1 | 5/2016 | Misra et al. | |
| 2016/0187525 A1 | 6/2016 | Wilson et al. | |
| 2017/0276832 A1* | 9/2017 | Kouchmeshky | G01V 99/005 |

OTHER PUBLICATIONS

Attia,, A. M., "Effects of petrophysical rock properties on tortuosity factor", Journal of Petroleum Science and Engineering, 2005, 48(3-4), pp. 185-198.

Chassagne, C. et al. "The dielectric response of a colloidal spheroid", Journal of Colloid and Interface Science, 2008, 326(1), pp. 240-253.

Chew, W. C. et al., "Dielectric enhancement due to electrochemical double layer: Thin double layer approximation", The Journal of Chemical Physics, 1982, 77, pp. 4683-4693.

Da Rocha, B. R. P et al., "Fractal geometry, porosity and complex resistivity: from rough pore interfaces to hand specimens", Geological Society, London, Special Publications, 1997, 122(1), pp. 277-286.

Freed, D. et al., "A Physics-Based Model for the Dielectric Response of Shaly Sands", presented at the SPWLA 57th Annual Logging Symposium, Reykjavik, Iceland, 2016, 20 pages.

Han, M. et al., "Continous Estimate of Cation Exchange Capacity from Log Data: A New Approach Based on Dielectric Dispersion Analysis", presented at the SPWLA 53rd Annual Logging Symposium. Society of Petrophysicists and Well-Log Analysts, 2012, 15 pages.

Hizem, M. et al., "Dielectric Dispersion: A New Wireline Petrophysical Measurement", presented at the Annual Technical Conference and Exhibition, Denver, Colorado, USA, SPE-116130, 2008, 21 pages.

Klein, L. et al., "An improved model for the dielectric constant of sea water at microwave frequencies", IEEE Transactions on Antennas and Propagation, 1977, 25(1), pp. 104-111.

Brown, R. J. S. , "Connection between formation factor for electrical resistivity and fluid-solid coupling factor in Biot's equations for acoustic waves in fluid-filled porous media", Geophysics, 1980 45(8), pp. 1269-1275.

Sen, P. N. et al., "A self-similar model for sedimentary rocks with application to the dielectric constant of fused glass beads", Geophysics, 1981, 46(5), pp. 781-795.

Vinegar, H. J. et al., "Induced Polarization of Shaly Sands", Geophysics, 1984, 49(8), pp. 1267-1287.

Wang, H. et al.,"The Broadband Electromagnetic Dispersion Logging Data in a Gas Shale Formation: A Case Study", presented at the SPWLA 54th Annual Logging Symposium in New Orleans, Louisiana, USA, Society of Petrophysicists and Well-Log Analysts, 2013, 12 pages.

Ben-Isreal, A. "A Newton-Raphson Method for the Solution of Systems of Equations", Journal of Mathematical Analysis and Applications, 1966, 15(2), 1966, pp. 243-252.

Seleznev, N. et al., "Dielectric Measurements on Artificial Compacted Clay-Quartz Mixtures", presented at the International Symposium of the Society of Core Analysts, Aberdeen, Scotland, UK, 2012, 6 pages.

Titov, K. et al., "Relationships between induced polarization relaxation time and hydraulic properties of sandstone", Geophysical Journal International, 2010, 180(3), pp. 1095-1106.

Maxwell-Garnett, J. C., "Colors in Metal Glasses and in Metal Films," Transaction of the Royal Society, vol. CCIII, 1904, pp. 385-420.

Moré, J. J. , "The Levenberg-Marquardt Algorithm: Implementation and Theory", in Numerical Analysis. Lecture Notes in Mathematics, Watson, G. A. (eds), Springer Berlin Heidelberg, 1978, 630, pp. 105-116.

Search Report and Written Opinion of International Patent Application No. PCT/US2017/058660, dated Feb. 13, 2018 (19 pages).

* cited by examiner

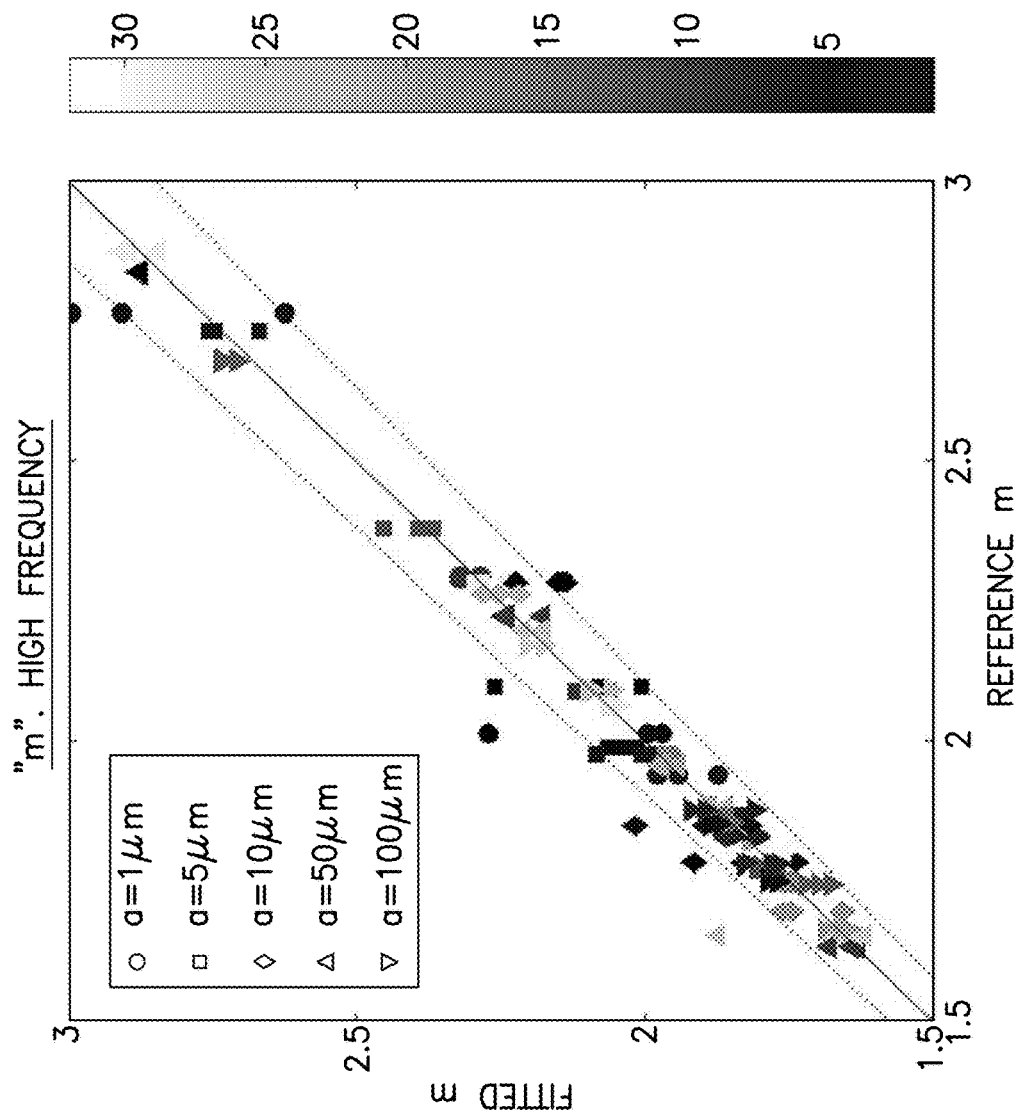

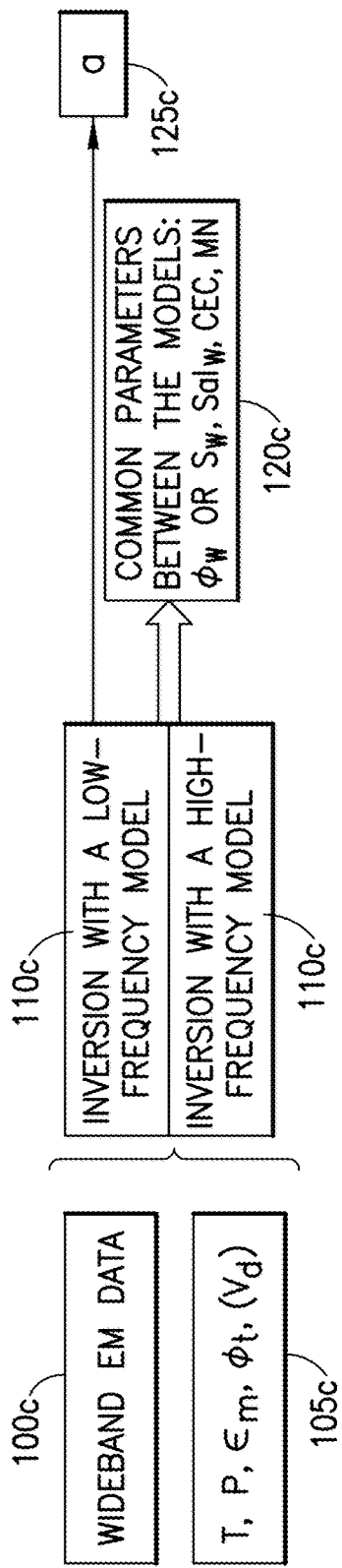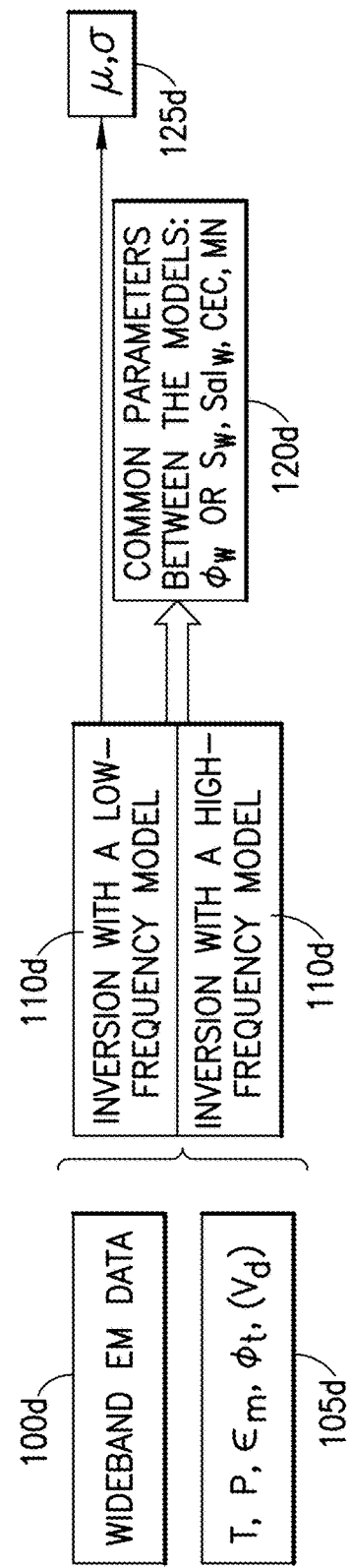
FIG. 16C
FIG. 16D

EVALUATION OF FORMATION UTILIZING WIDEBAND ELECTROMAGNETIC MEASUREMENTS

FIELD

The subject disclosure relates to the evaluation of geological formations. More particularly, the subject disclosure relates to using electromagnetic logs or measurements for determining values for the parameters of a formation or the rock thereof.

BACKGROUND

Presently, in investigating rock samples, electromagnetic (EM) evaluation methods exploit the response of an apparatus either to a single frequency or to multiple frequencies that are essentially governed by the same physics. Most EM formation evaluation is carried out by resistivity logging tools that are based on induction or galvanic principles. Multi-frequency measurements employed by resistivity tools are primarily used to optimize the measurement sensitivity for various formation and borehole properties, but do not provide substantially different information in terms of formation EM properties.

More recently, use of EM formation dispersion properties in the microwave frequency range has been proposed to obtain new petrophysical information. See, e.g., U.S. Pat. No. 7,376,514 to Habashy et al., U.S. Pat. No. 7,363,160 to Seleznev et al., and Freed, D., et al., "A Physics-Based Model for the Dielectric Response of Shaly Sands," Trans. of SPWLA Annual Symposium, Jun. 25-29, 2016, which are all hereby incorporated by reference herein in their entireties.

EM formation evaluation has also been proposed in the low-frequency range of the EM spectrum (from a fraction of 1 Hz to hundreds of kiloHertz). See, U.S. Pat. No. 7,863,901 to Seleznev et al. In this frequency range, the formation response is governed by the physical phenomena collectively referred to as the "induced polarization effects". See, Schlumberger, C., "Etude Sur la Prospection Electrique du Sous-Sol", Paris Gauthier-Villars et Cie., 1920.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, investigation of a rock sample involves the use of EM measurements of the rock sample in which wideband electromagnetic response data are obtained and processed by inversion in order to determine values for a plurality of parameters of the rock sample. The wideband electromagnetic response data is derived from EM measurements of the rock sample at frequencies that fall within a wideband of frequencies, wherein the wideband of frequencies includes a low frequency sub-band that is sensitive to conductivity of the rock sample and a high frequency sub-band that is sensitive to the permittivity of the rock sample. In embodiments, the low frequency sub-band includes one or more frequencies less than 10 KHz, and the high frequency sub-band includes one or more frequencies greater than 10 MHz.

In one embodiment, the inversion can employ a wideband model that accounts for two different polarization mechanisms, including i) polarization on interfaces between conductive fluid and non-conductive mineral grains, and ii) polarization of an electrical double layer present on charged mineral grains. The wideband model can be used to describe predicted electromagnetic response of the rock sample at frequencies that fall within the wideband of frequencies, and inversion of the wideband electromagnetic response data is utilized to identify values for the parameters of the rock sample.

In another embodiment, at least two models are used to describe predicted electromagnetic response of the rock sample in different frequency sub-domains (e.g., low frequency and high frequency sub-domains), and a joint inversion of the wideband electromagnetic response data utilizing the at least two models can be conducted to identify values for the parameters of the rock sample. For example, the joint inversion can involve simultaneous inversion of the wideband electromagnetic response data to identify values for at least parameters of the rock sample that are common to the models.

In one embodiment, the parameters of the rock sample that are derived from the inversion can be selected from the group consisting of: water-filled porosity, water salinity, a cementation and saturation exponent, cation exchange capacity, and a grain size indicator. The grain size indicator may be a determination of the predominant grain size, or determinations of multiple grain sizes (e.g., specific sizes or a grain size distribution).

In one embodiment, the wideband electromagnetic response data is interpreted using a wideband approach in a shallow zone surrounding a borehole and the information obtained therefrom is extended from the shallow zone to the deep zone in order to interpret the low-frequency EM data more robustly and to derive additional petrophysical parameters.

Additional aspects, embodiments, and advantages of the disclosure may be understood with reference to the following detailed description taken in conjunction with the provided drawings.

BRIEF DESCRIPTION OF THE DRAWINGS

FIGS. 8a-8c are plots of three parameters inverted from high-frequency data; the three parameters include water-filled porosity $\phi_w$ (FIG. 8a), water salinity $Sal_w$ (FIG. 8b) and cementation exponent m (FIG. 8c); the plots show the inverted values for these three parameters versus the true or actual values for these three parameters for comparison purposes.

FIGS. 16c and 16d are flow charts showing inversion of wideband EM response data of a formation utilizing both low-frequency and high-frequency models for determining formation parameters.

DETAILED DESCRIPTION

Figure 1A:
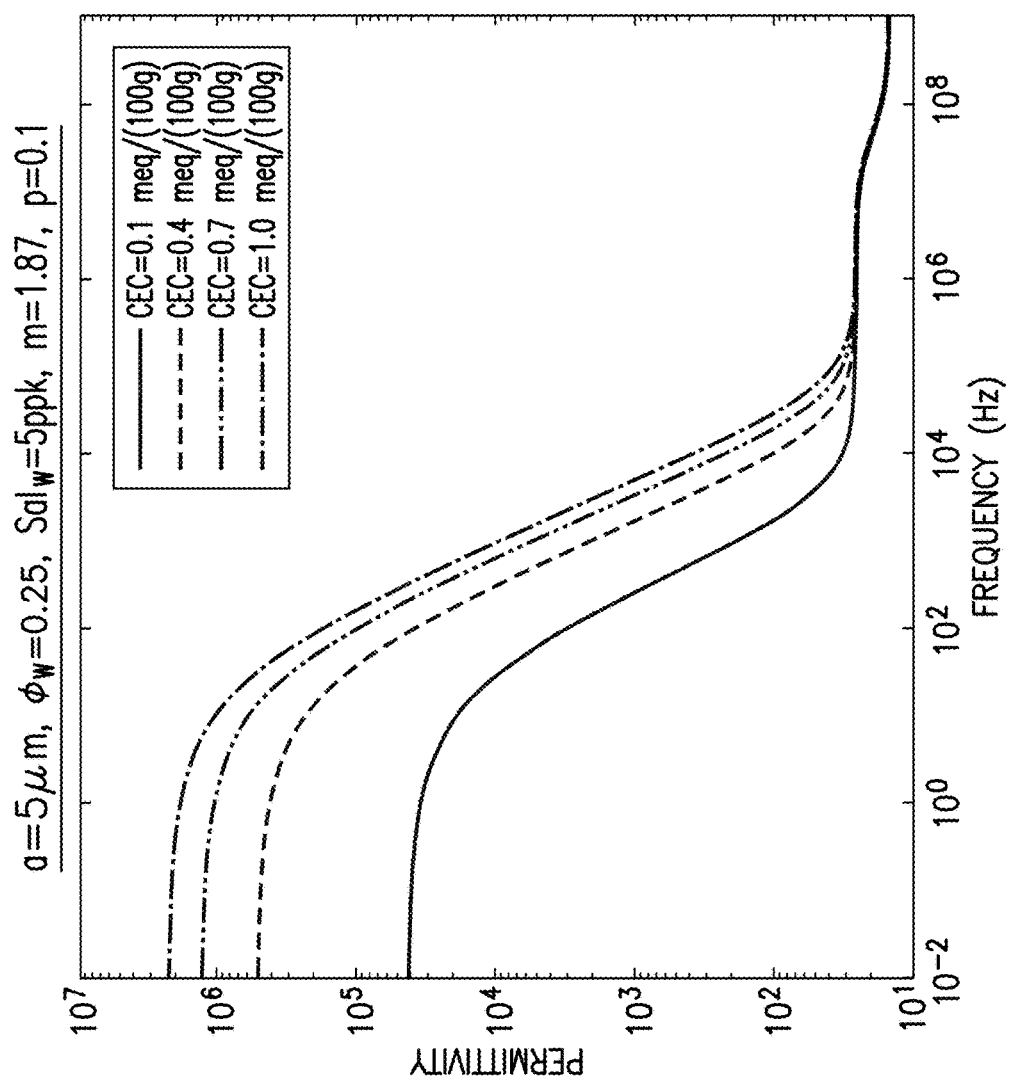
FIGS. 1a and 1b are plots of the response of a wideband grain polarization model that shows the dependence of permittivity with respect to frequency for changing cation exchange capacity or CEC (FIG. 1a) and the dependence of conductivity with respect to frequency for changing CEC (FIG. 1b).

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show details in more detail than is necessary, the description taken with the drawings making apparent to those skilled in the art how the several forms of the subject disclosure may be embodied in practice. Furthermore, like reference numbers and designations in the various drawings indicate like elements.

Various electromagnetic (EM) logging tools operate at different frequencies. Induced polarization logging tools generally operate in the range of frequencies from DC or milliHz to hundreds of KHz. It should be appreciated that the induced polarization measurements can be realized in both the time domain and the frequency domain. In the frequency domain, the induced polarization measurements constitute the measurement of the complex formation conductivity as a function of frequency and are referred to as the "Spectral Induced Polarization" or SIP measurements. In the time domain, induced polarization measurements constitute the measurement of the formation polarization magnitude decay versus time.

Lateralog tools (such as the DLL tool of SCHLUMBERGER™) generally use an electrode for injecting current into a formation and one or more electrodes for measuring current returning from the formation to the tool. Lateralog-type resistivity measurements typically operate in the range of tens to hundreds of Hertz (Hz).

Induction-type tools (such as the AIT—Array Induction Imager tool of SCHLUMBERGER™) include a transmitter coil and one or more receiver coils that are spaced from the transmitter coil. The transmitter coil is driven by an alternating current that creates a primary magnetic field around the transmitter coil(s). The primary magnetic field causes eddy currents to flow in a formation which in turn generate a secondary magnetic field which induces an alternating voltage in the receiver coils. Induction-type resistivity measurements often operate in the range of one kiloHertz (kHz) to tens or even hundreds of kHz.

Propagation-type resistivity tools (such as the arcVISION tool of SCHLUMBERGER™) generally operate in the range of hundreds of kHz to the single or even tens of megaHertz (MHz).

Dielectric logging tools (such as the Dielectric Scanner of SCHLUMBERGER™) may include an antenna array with collocated transverse and longitudinal transmitters and receivers set on an articulated pad that is in contact with the borehole wall. The dielectric logging tools generally operate in the range of tens of MHz to the gigaHertz (GHz). Propagation of electromagnetic waves is controlled by the conductivity and dielectric permittivity of the medium in which the waves are propagating thereby allowing for evaluation of the dielectric dispersion, i.e., the change in dielectric properties as a function of frequency. Analysis of dielectric dispersion allows for the separation and quantification of the different effects influencing the dielectric measurement, such as water volume, water salinity and rock texture.

Also note that there is a broad array of EM laboratory equipment that measures electromagnetic response data for rock samples of a formation in order to characterize petrophysical properties of such formation. Similar to the EM logging tools as described above, such EM laboratory equipment operates over a wide range of different frequencies.

For purposes herein, the electromagnetic response data acquired by these various EM logging tools and laboratory equipment can be measured in the frequency domain or the time domain. If needed, electromagnetic response data measured in the frequency domain can be converted to the time domain using methods well known in the art such as inverse Fourier transforms, or electromagnetic response data measured in the time domain can be converted to the frequency domain using methods well known in the art.

According to one aspect, in a low-frequency range or sub-band (which in embodiments can include one or more frequencies less than 10 KHz, the EM response data measured for the formation is sensitive to and even dominated by the induced polarization of the formation. Thus, this low-frequency range may be referred to as the "induced polarization domain." The induced polarization of the formation is a measure of the complex electrical conductivity of the formation at low frequencies. Induced polarization can be observed when a steady current through two electrodes in contact with the formation is shut off: the voltage does not return to zero instantaneously, but rather decays slowly, indicating an unusually strong polarization response in the rock. This strong polarization response often occurs due to the presence of charge-bearing or conducting minerals that give large induced dipole moment upon the application of an electric field. Induced polarization can be measured in the time domain by observing the rate of decay of voltage, or in the frequency domain by measuring phase shifts between sinusoidal currents and voltages. In one embodiment, the low frequency sub-band can include frequencies that emcompass the range from milliHz to 1 KHz (the EM response data in this frequency range is particularly useful for characterizing quartz or quartz-like rock). In another embodiment, the low frequency sub-band can include frequencies that encompass the range from one Hz to 10 KHz (the EM response data in this frequency range is particularly useful for characterizing clay-bearing rock). In yet another embodiment, the low frequency sub-band can include frequencies that encompass the range from one milliHz to 10 KHz (the EM response data in this frequency range is particularly useful for characterizing both quartz and clay-bearing rock). In these embodiments, the low frequency sub-band can include one or more frequencies that fall outside of the specified range if desired.

In contrast, in a high-frequency range or sub-band (which in embodiments includes one or more frequencies greater 10 MHz), the EM response data measured for the formation is sensitive or even dominated by the complex electrical permittivity of the formation. Thus, this high-frequency range may be referred to as the "dielectric domain". In one embodiment, the high frequency sub-band can include one or more frequencies that fall within the range from tens of MHz to tens of GHz. In another embodiment, the high frequency sub-band can include one or more frequencies at or near one GHz. In yet another embodiment, the high frequency sub-band can include one or more frequencies that fall within the range from 10 to 20 MHz. In all of these embodiments, the high frequency sub-band can include one or more frequencies that fall outside of the specified range if desired.

Thus, the EM response data measured for a formation in different frequency ranges is controlled by different phenomena. Consequently, EM measurements made by one or more tools or laboratory equipment at different frequencies can have different, and in some cases unique sensitivities to the petrophysical properties of the formation. Table 1 illustrates the EM measurement sensitivities in different frequency ranges.

TABLE 1

| Petrophysical Property | Dielectric Domain-Real Permittivity | Dielectric Domain-Imaginary Permittivity | Induced Polarization Domain-Real Conductivity | Induced Polarization Domain-Imaginary Conductivity |
|---|---|---|---|---|
| Grain Size | None | None | None | Strong |
| Grain shape | Strong | Strong | Medium | Low |
| Qv (CEC) | Medium | Medium | Medium | Strong |
| Water-filled porosity | Strong | Strong | Medium | Low |
| Salinity | Medium | Strong | Strong | Medium |

As will be described in more detail hereinafter, in embodiments, formation evaluation will be based on the inversion of the wideband EM response data of a formation obtained in both the dielectric and induced polarization domains. Analysis of the wideband EM response data provides complementary sensitivities to the petrophysical parameters of the formation and yields more robust results than previously. The wideband EM response data or "wideband data" includes data (referred to herein as "low-frequency EM response data") derived from EM measurements at frequencies that fall within the low frequency sub-band or induced polarization domain as well as data (referred to herein as "high-frequency EM response data") derived from EM measurements at frequencies that fall within the high frequency sub-band or dielectric domain. The combination of the high-frequency EM response data and the low-frequency EM response data as part of the wideband data enables new applications, including, but not limited to determining a variety of parameters that characterize petrophysical properties of the formation such as grain size a and grain shape, CEC, Qv (CEC/unit pore volume), water-filled porosity $\phi_w$, water salinity $Sal_w$, cementation exponent m, fraction of uncharged spheroids p and a parameter related to the aspect ratio of the spheroids $d_L$.

More particularly, as seen in Table 1, while high-frequency EM response data has higher sensitivity to grain shape of the formation, the low-frequency EM response data has stronger sensitivity to grain size a of the formation. Inversion of wideband data can provide information about both the grain size a and grain shape of the formation. The grain shape information allows evaluation of formation textural parameters such as the cementation exponent m. Inversion for more complex textural parameters such as grain size distribution of the formation is also possible providing sufficiently detailed low-frequency EM response data is available.

It is also seen in Table 1 that there is a strong sensitivity of Qv to the low-frequency imaginary conductivity of the formation. Given the medium sensitivity of Qv to the high-frequency dielectric permittivity, more robust values or an extended salinity range for the Qv estimate may be obtained from inversion of the wideband data. For example, in Vinegar, H. J. and Waxman, M. H. "Induced Polarization of Shaly Sands," Geophysics, Vol. 49(8), 1984, pp. 1267-1287, it was demonstrated that there is a correlation between imaginary conductivity and Qv for NaCl solutions with concentrations up to 2.0M. This salinity corresponds to 117 ppk NaCl solution concentration, which is significantly higher than the salinity cutoffs for Qv (or CEC) determination from the high-frequency data for samples with comparable porosity.

With respect to water-filled porosity $\phi_w$ of the formation, as seen in Table 1, high-frequency complex permittivity is very sensitive to the water-filled porosity $\phi_w$ of the formation and this is one of its primary petrophysical outputs. Petrophysical interpretation of the real and imaginary conductivity in the low-frequency EM response data can strongly benefit from an accurate input for the water-filled porosity $\phi_w$.

Both the imaginary part of the permittivity and the real part of the conductivity are sensitive to water salinity $Sal_w$ of the formation (which can also be referred to as "brine salinity"). However, the exact dependencies are different in different frequency domains that will make the determination of water salinity $Sal_w$ more robust. Alternatively, water salinity $Sal_w$ of the formation can be determined from the measured EM response data in a single domain (e.g., the dielectric domain or high-frequency range) and used as an input to interpret EM response data in the other domain (e.g., the induced polarization domain or low-frequency range).

Note that low-frequency EM response data of a formation (which corresponds to the induced polarization domain) can be measured by at least one EM logging tool as described above. Such EM logging tool(s) can include i) an induced polarization logging tool, whose operating frequency is generally in the range of frequencies from DC or milliHz to hundreds of KHz; ii) a Laterolog-type resistivity logging tool, whose operating frequency is generally in the range of frequencies from tens to hundreds of Hertz (Hz); and iii) an induction-type logging tool, whose operating frequency is generally in the range of frequencies from one kiloHertz (kHz) to tens or even hundreds of kHz.

Also note that high-frequency EM response data of the formation (which corresponds to the dielectric domain) can be measured by at least one EM logging tool as described above. Such EM logging tool(s) can include a dielectric logging tool, whose operating frequency is generally in the range of tens of MHz to gigaHertz (GHz).

According to one aspect, a wideband model may be provided that is applicable to formations containing grains with a moderate amount of surface charge such as quartz and kaolinite. This wideband model, which is referred to as a wideband grain polarization model, accounts for two key polarization mechanisms present in oilfield formations: the polarization on the interfaces between the conductive fluid and non-conductive mineral grains and/or non-conductive hydrocarbons, and the polarization of the electrical double layer present on charged mineral grains.

The wideband grain polarization model considers spherical charged inclusions with surface charge density, $\Gamma_0$, which can be related to the cation exchange capacity (CEC) according to:

$$\frac{\Gamma_0}{a} = \frac{\rho}{3e_0}\left(\frac{CEC}{100}\right)(1 - f_{stern}) \times \text{units} \tag{1}$$

where $0 < f_{stern} < 1$ is the factor associated with the fraction of ions in the Stern layer that reduces the mobile ions in the diffuse part of the electrical double layer, $e_0$ is the absolute value of an electron charge, $\rho$ is the density in $g/cm^2$, a is the radius of the spherical grain, and the units=$9.64 \times 10^7$ convert the CEC from meq/100 g to coulumb. It also includes non-charged spheroidal inclusions that reflect changes in texture between different rocks and is related to changes in the cementation exponents of the rock. The volume fraction of the spheroidal inclusions in the rock matrix will be designated asp and the volume fraction of the charged spherical inclusions is 1−p where 0<p<1.

For a charged spherical particle immersed in a brine, the polarization coefficient $p_{sphere}$ is given by:

$$p^{sphere} = \frac{\varepsilon_m^* - \left(\varepsilon_w + i\frac{\sigma_w^{ex}}{\omega\varepsilon_0}\right)}{\varepsilon_m^* + 2\left(\varepsilon_w + i\frac{\sigma_w^{ex}}{\omega\varepsilon_0}\right)} \tag{2}$$

where $\omega = 2\pi f$ is the radial frequency, $\varepsilon_0$ is the vacuum permittivity, $\varepsilon_w$ is the complex dielectric constant of the brine, $\varepsilon_m^*$ is the effective complex dielectric constant of a charged grain, and $\sigma_w^{ex}$ is the extra conductivity induced by the charged grain.

The complex dielectric constant of a charged grain $\varepsilon_m$ is defined as:

$$\varepsilon_m^* = \varepsilon_m + i\frac{\Gamma_0 \sigma_w}{N_0 a}\frac{1}{\omega\varepsilon_0}. \tag{3}$$

In equation (3), the first term $\varepsilon_m$ is the real dielectric constant of the grain matrix and $\sigma_w = 2D(Ze_0)^2 N_0/(k_B T)$ is the intrinsic brine conductivity with the ion concentration $N_0$. The second term of equation (3) comes from the additional conductivity due to charges carried by the spherical particle. The extra conductivity $\sigma_w^{ex}$ is defined as:

$$\sigma_w^{ex} = \frac{\Gamma_0 \sigma_w}{N_0 a} \frac{1}{y}, \quad y = \frac{\lambda^2 a^2 + 2\lambda a + 2}{\lambda a + 1}, \quad \lambda = e^{-i\pi/4}\sqrt{\frac{\omega}{D}}. \tag{4}$$

Here, the ion charge is $Ze_0$, the diffusion coefficient is D, $e_0$ is the absolute value of an electron charge, $k_B$ is the Boltzmann constant, and T is the temperature in degrees Kelvin. It is noted that:

$$\frac{\Gamma_0 \sigma_w}{N_0 a} = \frac{2D(Ze_0)^2 \Gamma_0}{ak_B T}, \tag{5}$$

which does not depend on brine conductivity explicitly. Hence, both $\varepsilon_m^*$ and $\sigma_w^{ex}$ are treated as part of grain properties in the differential effective medium inclusion process discussed hereinafter.

Polarization coefficients of an uncharged spherical grain $P_\alpha^{spheroid}$ for $\alpha = x, y, z$ directions are given by:

$$P_\alpha^{spheroid} = \frac{1}{3} \frac{\varepsilon_m - \varepsilon_w}{L_\alpha \varepsilon_m + (1 - L_\alpha) \varepsilon_w} \tag{6}$$

where $L_\alpha$ is the depolarization factor in the $\alpha$ direction, which is related to the aspect ratio of the spheroid and follows the relation $L_{x,y} = (1-L_z)/2$. It is often convenient to define $L_z = 1-d_L$ and $L_{x,y} = d_L/2$, where $d_L$ is a parameter depending only on the aspect ratio of spheroids.

To derive properties of a dense mixture, methods may be employed similar to the method presented in Sen et al., "A Self-similar Model for Sedimentary Rocks with Application to the Dielectric Constant of Fused Glass Beads," Geophysics, Vol. 46(5), 1981, pp. 781-795. In particular, using the differential effective medium approximation where a small volume of grains, $dV_m$, is added to the host in an infinitesimal step, a differential equation can be derived that represents the change of the complex dielectric constant for each infinitesimal step according to:

$$\frac{d\varepsilon}{\varepsilon} = \frac{dV_m}{V_w + V_m} + \left\{ p \left[ \frac{\varepsilon_m - \varepsilon}{(1-d_L)\varepsilon_m + d_L \varepsilon} + 2(1-f_a) \frac{\varepsilon_m - \varepsilon}{d_L \varepsilon_m - (2-d_L)\varepsilon} \right] + \right.$$
$$\left. 3(1-p) \frac{\varepsilon_c - i\sigma_w^{ex}/(\omega\varepsilon_0)) - \varepsilon}{\varepsilon_c + 2i\sigma_w^{ex}/(\omega\varepsilon_0)) - 2\varepsilon} \right\} \tag{7}$$

where $f_a$ is the alignment factor defined along the z-axis and p is the volume fraction of spheroids. As a result, fractions of non-charged spheroids aligned in each direction are given by $p_z = pf_a$ and $p_x = p_y = p(1-f_a)/2$ respectively. In addition, it is assumed that water is the initial phase of the host with the volume $V_w$. By defining the volume faction of the matrix $\tau = V_m/(V_w + V_m)$, it follows that $d\tau/(1-\tau) = dV_m/(V_w + V_m)$. Now, performing the integration of $\tau$ from $\tau = 0$ to $\tau = 1-\phi$ for rock porosity $\phi$ and the rock effective dielectric constant $\varepsilon_r$, the following mixing formula can be derived for a single grain size:

$$\phi = \prod_{j=0}^{3} \left( \frac{\varepsilon_w - p_j}{\varepsilon_r - p_j} \right)^{r_j}. \tag{8}$$

Here $p_j$ and $r_j$ are poles and residues of the rational function $f(\varepsilon) = D(\varepsilon)/\varepsilon N(\varepsilon)$ with $$N(\varepsilon) = pf_a(\varepsilon_m - \varepsilon)[d_L \varepsilon_m + (2-d_L)\varepsilon]\left[\varepsilon_m + \frac{2i\sigma_w^{ex}}{\omega\varepsilon_0} + 2\varepsilon\right] + \tag{9}$$
$$2p(1-f_a)(\varepsilon_m - \varepsilon)[(1-d_L)\varepsilon_m + d_L\varepsilon]\left[\varepsilon_m + \frac{2i\sigma_w^{ex}}{\omega\varepsilon_0} + 2\varepsilon\right] +$$
$$(1-p)\left[\varepsilon_m - \frac{i\sigma_w^{ex}}{\omega\varepsilon_0} - \varepsilon\right][(1-d_L)\varepsilon_m + d_L\varepsilon][d_L\varepsilon_m + (2-d_L)\varepsilon]$$

and $$D(\varepsilon) = [(1-d_L)\varepsilon_m + d_L\varepsilon][d_L\varepsilon_m + (2-d_L)\varepsilon][\varepsilon_m + 2i\sigma_w^{ex}/(\omega\varepsilon_0)) + 2\varepsilon]. \tag{10}$$

The cementation exponent m can be further calculated according to:

$$m = (1-p)\frac{3}{2} + p\frac{2f_a + d_L(2-3f_a)}{d_L(2-d_L)}. \tag{11}$$

The cementation exponent m is associated with a parameter in Archie's law that relates electrical conductivity, $\sigma_0$, of fully brine-saturated rock to its porosity, $\phi$, and brine conductivity, $\sigma_w$, according to $\sigma_0 = \sigma_w/\phi^m$. In addition, $F = \phi^{-m}$ is often referred to as the formation factor and is related to the electrical tortuosity defined as $\alpha = F\phi = \phi^{1-m}$. See, e.g., Brown, R. J. S., "Connection between Formation Factor for Electrical Resistivity and Fluid-Solid Coupling Factor in Biots' Equations for Acoustic Waves in Fluid-Filled Porous Media," Geophysics, Vol. 45(8), 1980, pp. 1269-1275.

Other mixing rules that relate properties of the rock (such as porosity) to the EM response data of the formation can be used if desired. For example, one such mixing rule is the Bruggeman mixing rule as described by Tsang, L., Kong, J., Shin, R., "Theory of Microwave Remote Sensing", Wiley-Interscience, 1985. Another suitable mixing rule is the Maxwell-Garnett mixing rule as described by Maxwell-Garnett, J. C., "Colors in Metal Glasses and in Metal Films," Transaction of the Royal Society, vol. CCIII, 1904, pp. 385-420. Other mixing laws known in the art can also be used.

For multiple grain sizes, equation (8) may be expanded as follows:

$$\phi = \prod_{j=0}^{4} \left( \frac{\varepsilon_w - p'_j}{\varepsilon_r - p'_j} \right)^{r'_j} \tag{12}$$

where $p'_j$ and $r'_j$ are poles and residues of the rational function $f_2(\varepsilon) = D_2(\varepsilon)/\varepsilon N_2(\varepsilon)$ with the following equation is for 2 grain sizes. For more grain sizes the formulae are similar but more complicated.

$$N_2(\varepsilon) = pf_a(\varepsilon_m\ \varepsilon)[d_L\varepsilon_m + (2\ d_L)\varepsilon]\left[\varepsilon_{m,1} + \frac{2i\sigma_{w,1}^{ex}}{\omega\varepsilon_0} + 2\varepsilon\right] \quad (13)$$

$$\left[\varepsilon_{m,2} + \frac{2i\sigma_{w,2}^{ex}}{\omega\varepsilon_0} + 2\varepsilon\right] +$$

$$2p(1\ f_a)(\varepsilon_m\ \varepsilon)[(1\ d_L)\varepsilon_m + d_L\varepsilon]\left[\varepsilon_{m,1} + \frac{2i\sigma_{w,1}^{ex}}{\omega\varepsilon_0} + 2\varepsilon\right]$$

$$\left[\varepsilon_{m,2} + \frac{2i\sigma_{w,2}^{ex}}{\omega\varepsilon_0} + 2\varepsilon\right] + 3(1\ p)s_1((1\ d_L)\varepsilon_m + d_L\varepsilon)$$

$$(d_L\varepsilon_m + (2\ d_L\varepsilon))\left[\varepsilon_{m,1}\ \frac{i\sigma_{w,1}^{ex}}{\omega\varepsilon_0}\ \varepsilon\right]\left[\varepsilon_{m,2} + \frac{2i\sigma_{w,2}^{ex}}{\omega\varepsilon_0} + 2\varepsilon\right] +$$

$$3(1\ p)(1\ s_1)((1\ d_L)\varepsilon_m + d_L\varepsilon)(d_L\varepsilon_m + (2\ d_L\varepsilon))$$

$$\left[\varepsilon_{m,1} + \frac{2i\sigma_{w,1}^{ex}}{\omega\varepsilon_0} + 2\varepsilon\right]\left[\varepsilon_{m,2} + \frac{i\sigma_{w,2}^{ex}}{\omega\varepsilon_0}\ \varepsilon\right]$$

and $$D_2(\varepsilon) = ((1\ d_L)\varepsilon_m + d_L\varepsilon) \quad (14)$$

$$(d_L\varepsilon_m + (2\ d_L)\varepsilon)\left[\left(\varepsilon_{m,1} + \frac{2i\sigma_{w,1}^{ex}}{\omega\varepsilon_0}\right) + 2\varepsilon\right]\left[\left(\varepsilon_{m,2} + \frac{2i\sigma_{w,2}^{ex}}{\omega\varepsilon_0}\right) + 2\varepsilon\right].$$

Again, p is the volume fraction of the spheroidal (quartz) grains and $f_a$ is the alignment factor defined in the z-direction. The fraction of charged spheres with radius $a_1$ is given by $s_1$, while that with radius $a_2$ is $s_2=1-s$. Hence, the volume fractions of two different sized spheres are $f_{s,1}=(1-p)s_1$ and $f_{s,2}=(1-p)(1-s_1)$, respectively.

Similar to the earlier case, $\varepsilon_{m,i}*$ are effective dielectric constants of charged spheres with two different radius, $a_1$ and $a_2$, and are defined as:

$$\varepsilon_{m,i} = \varepsilon_m + i\frac{\Gamma_i\sigma_w}{N_0a_i}\frac{1}{\omega\varepsilon_0}. \quad (15)$$

In addition, extra water conductivities $\sigma_{w,j}^{ex}$ are given by:

$$\sigma_{w,i}^{ex} = \frac{\Gamma_i\sigma_w}{N_0a_i}\frac{1}{y_i},\ y_i = \frac{\lambda^2a_i^2 + 2\lambda a_i + 2}{\lambda a_i + 1},\ \lambda = e^{i\pi/4}\sqrt{\omega/D}, \quad (16)$$

with surface charge densities, $\Gamma_1$ and $\Gamma_2$, associated with two different sizes of spheres respectively. Finally, the surface charge density $\Gamma_i/a_i$ can be related to the $CEC_i$ corresponding to two different sized spheres as:

$$\frac{\Gamma_i}{a_i} = \frac{\varrho}{3e_0}\left(\frac{CEC_i}{100}\right)(1\ f_{stem}) \times \text{units.} \quad (17)$$

According to one aspect, the addition of the hydrocarbon phase can be done by lumping it with the matrix phase into a single "non-conductive" phase with the Complex Refractive Index Method (CRIM) or any other dielectric mixing law. CRIM is defined as follows:

$$\varepsilon_{\mathit{eff}}^{1/2} = \Sigma_{n=1}^N \phi_n\varepsilon_n^{1/2}, \quad (18)$$

where $\varepsilon_{\mathit{eff}}$ is the effective permittivity of the composite $\phi_n$ and $\varepsilon_{\mathit{eff}}$ are the volumetric fractions and permittivities of the mixture constituents. Hydrocarbons can also be added by including them as a separate phase into the mixing law.

It is noted that equations such as equations (8) and (12) may be extended to model any grain size distribution such that the grain size distribution may be represented by a discrete probability density function or a continuous probability density function such as a Gaussian distribution.

It will be appreciated that models such as equations (8) and (12) have responses to changes in the input parameters. The model response can be predicted by the equations. Instead of water conductivity, salt (NaCl) water salinity in parts per thousand (ppk) may be utilized. An empirical model allowing the conversion of water temperature and salinity into the water conductivity and permittivity over the low-frequency and the high-frequency ranges is presented in Klein, L., and Swift, C., "An Improved Model for the Dielectric Constant of Sea Water at Microwave Frequencies," IEEE Transactions on Antennas and Propagation, Vol. 25(1), 1977, pp. 104-111.

Figure 1B:
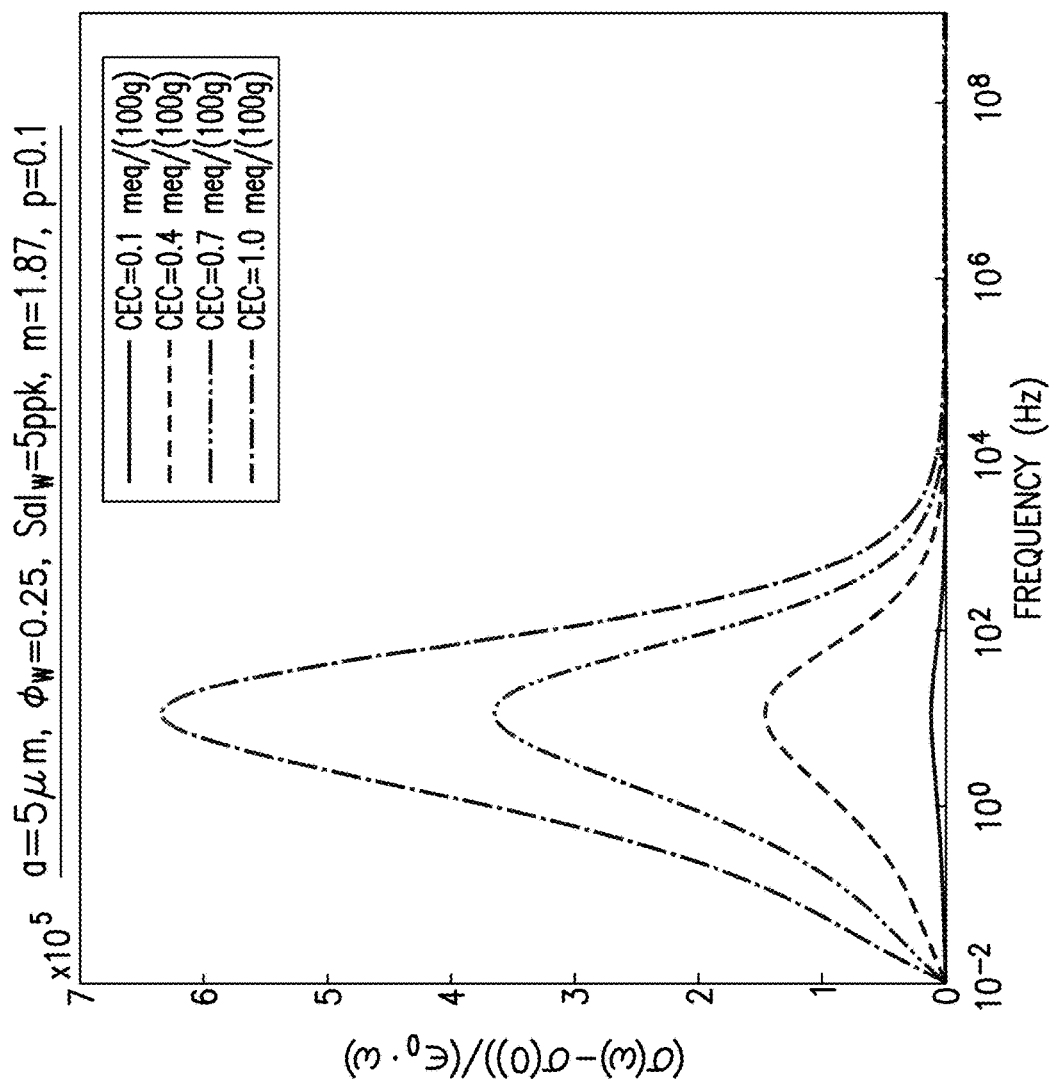

The effect of changing the CEC parameter on wideband EM response data is shown in FIGS. 1a and 1b where a strong enhancement of the low-frequency dielectric constant with increasing CEC is evident. As seen in FIG. 1b, the location of the peak in the excess conductivity $(\sigma(\omega)-\sigma(0))/(\omega\varepsilon_0)$ (at about 10 Hz) does not appear to depend significantly on the CEC.

Figure 2A:
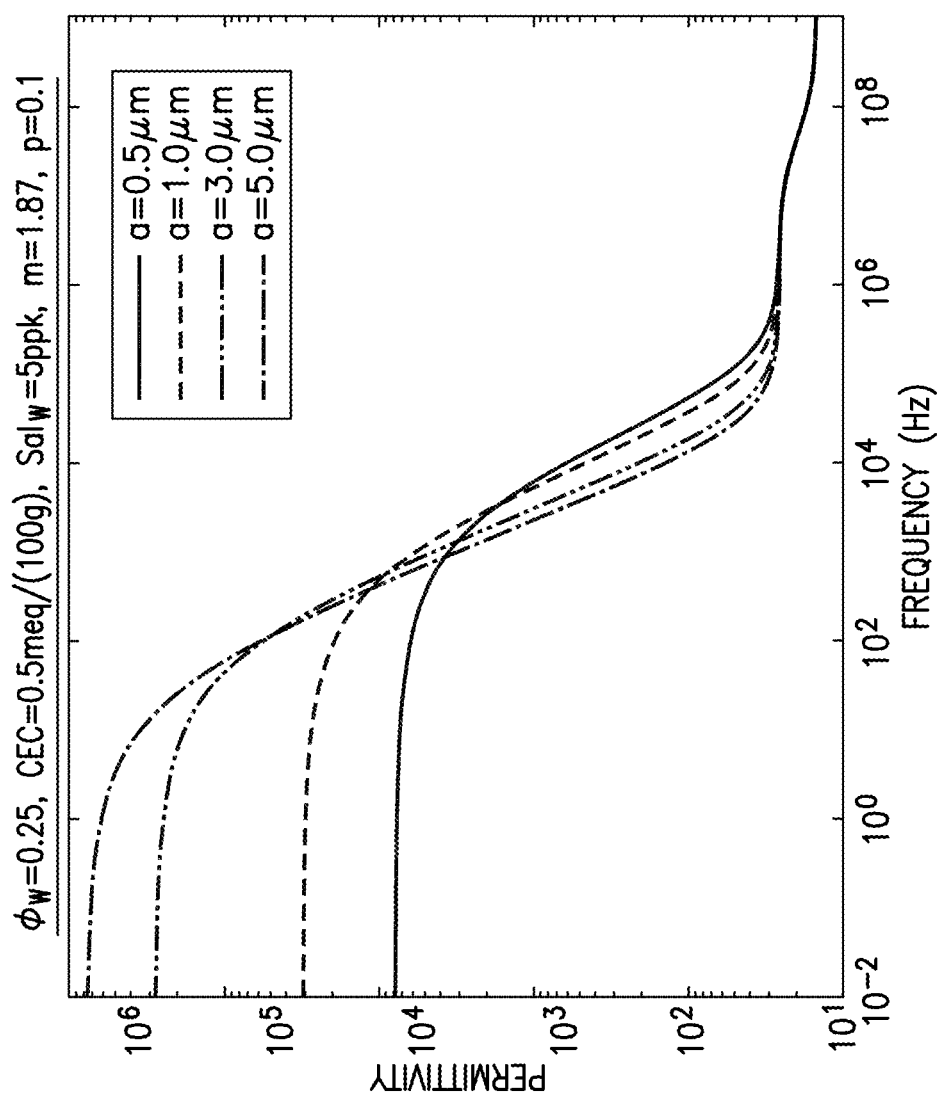
FIGS. 2a and 2b are plots of the response of the wideband grain polarization model that shows the dependence of permittivity with respect to frequency for changing charged grain size or radius a (FIG. 2a) and the dependence of conductivity with respect to frequency for changing charged grain size a (FIG. 2b).
Figure 2B:
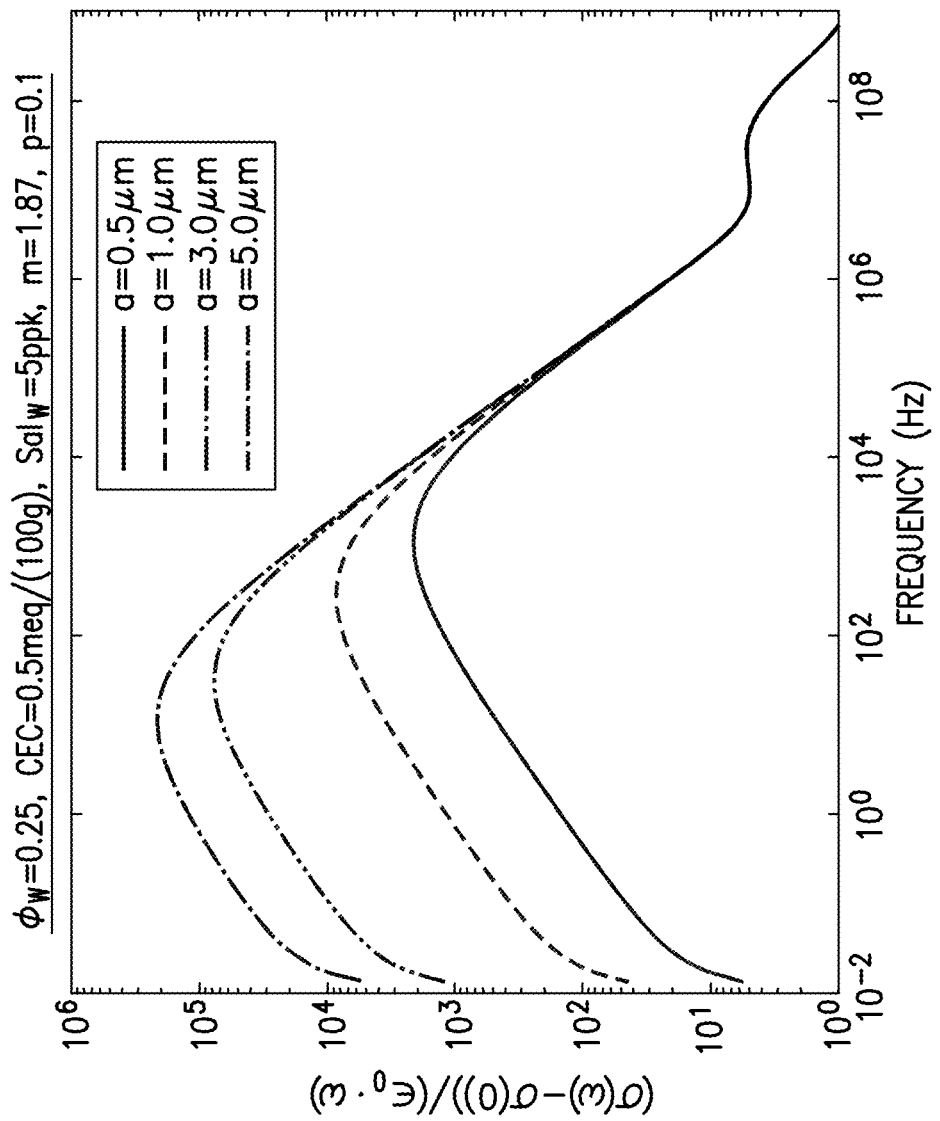

The effect of changing the grain size a on wideband EM response data is shown in FIGS. 2a and 2b. The characteristic frequency of the low-frequency relaxation scales as $\omega_c \sim D/a^2$. See, Chew, W. C., and Sen, P. N., "Dielectric Enhancement Due to Electrochemical Double Layer: Thin Double Layer Approximation," The Journal of Chemical Physics, Vol. 77.9, 1982, pp. 4683-4693. As a result, the characteristic frequency increases with decreasing grain size a, which can be clearly seen in the conductivity dispersion curves shown in FIG. 2b where the peak positions shift to higher frequencies for smaller grain sizes. The dielectric dispersion curves in FIG. 2a also show a similar trend. In addition, the low-frequency dielectric enhancement increases as the grain size a increases. In contrast, as long as the grain size a is larger than 0.1 μm, no effect of the grain size on the high-frequency response (f>10 MHz) is observed.

Figure 3A:
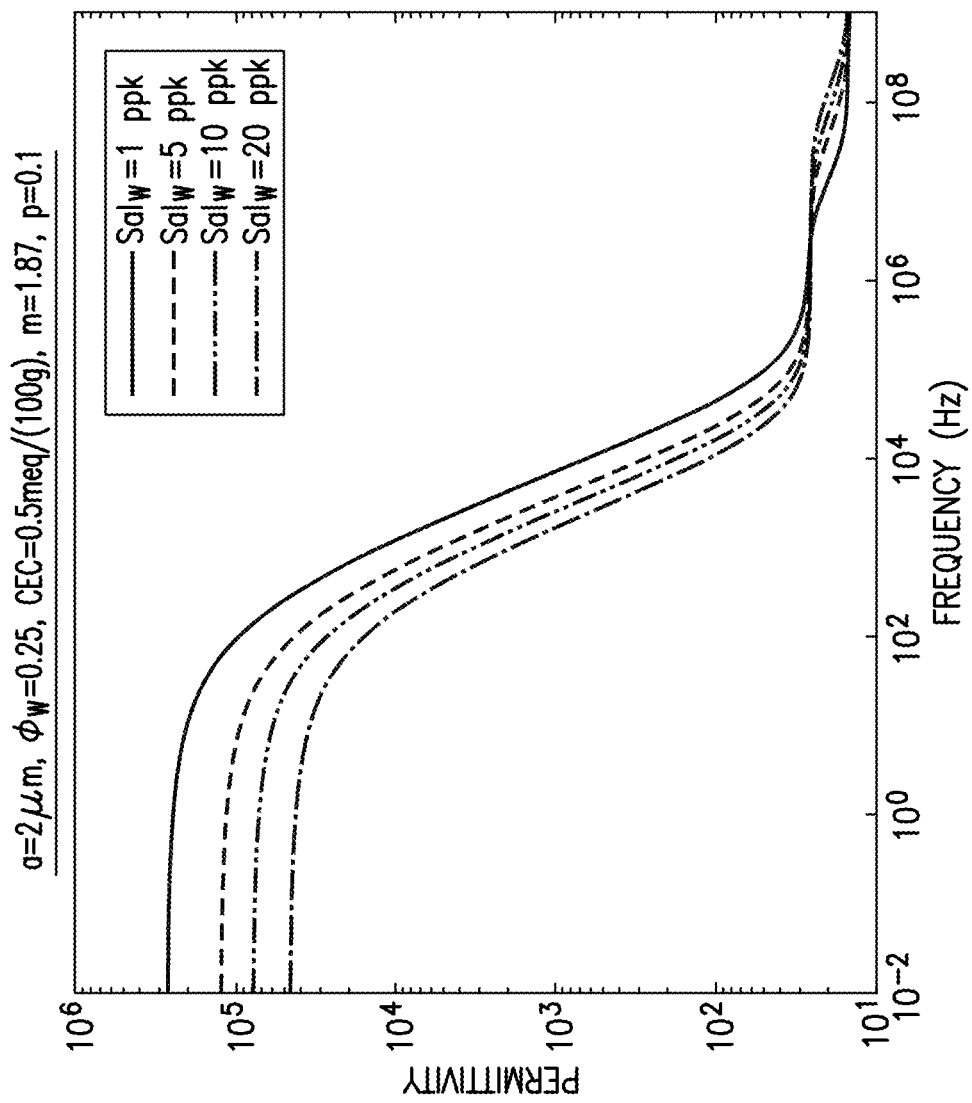
FIGS. 3a and 3b are plots of the response of the wideband grain polarization model that shows the dependence of permittivity with respect to frequency for changing water salinity $Sal_w$ (FIG. 3a) and the dependence of conductivity with respect to frequency for changing brine or water salinity $Sal_w$ (FIG. 3b).
Figure 3B:
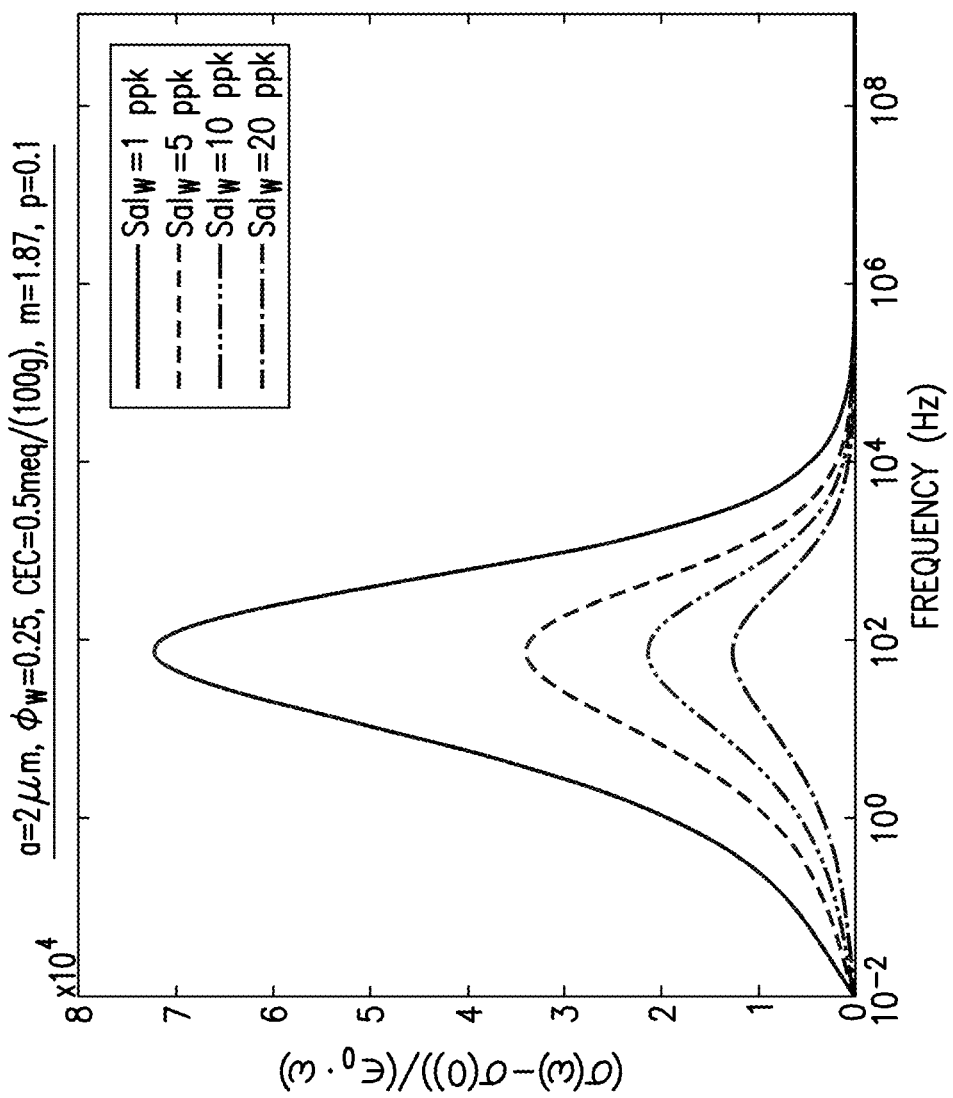

The effect of changing water salinity $Sal_w$ on wideband EM response data is shown in FIGS. 3a and 3b. Increase in water salinity $Sal_w$ leads to a moderate decrease in the low-frequency permittivity enhancement and to a decrease in the excess conductivity. The characteristic relaxation frequency in the low-frequency regime is not significantly dependent on water salinity $Sal_w$.

Figure 4A:
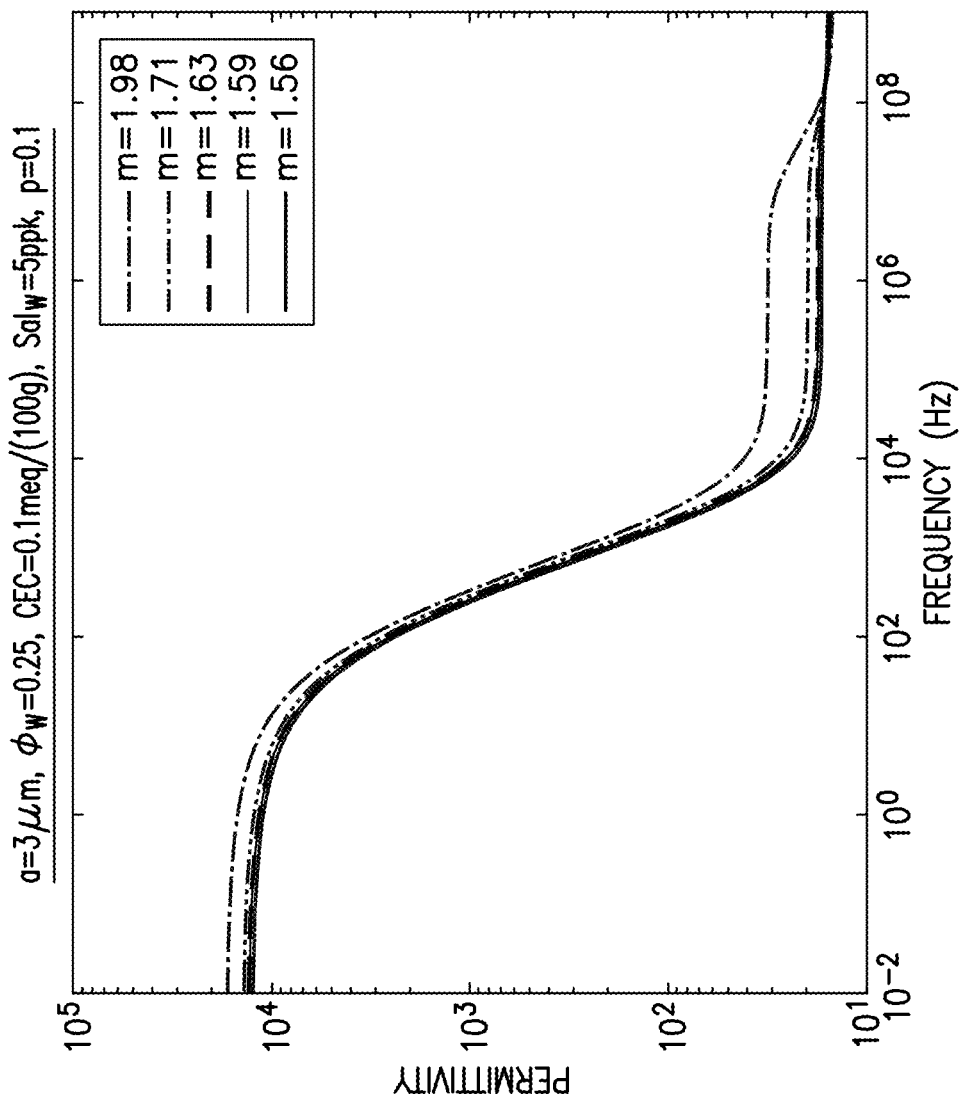
FIGS. 4a and 4b are plots of the response of the wideband grain polarization model that shows the dependence of permittivity with respect to frequency for changing cementation exponent m (FIG. 4a) and the dependence of conductivity with respect to frequency for changing cementation exponent m (FIG. 4b).
Figure 4B:
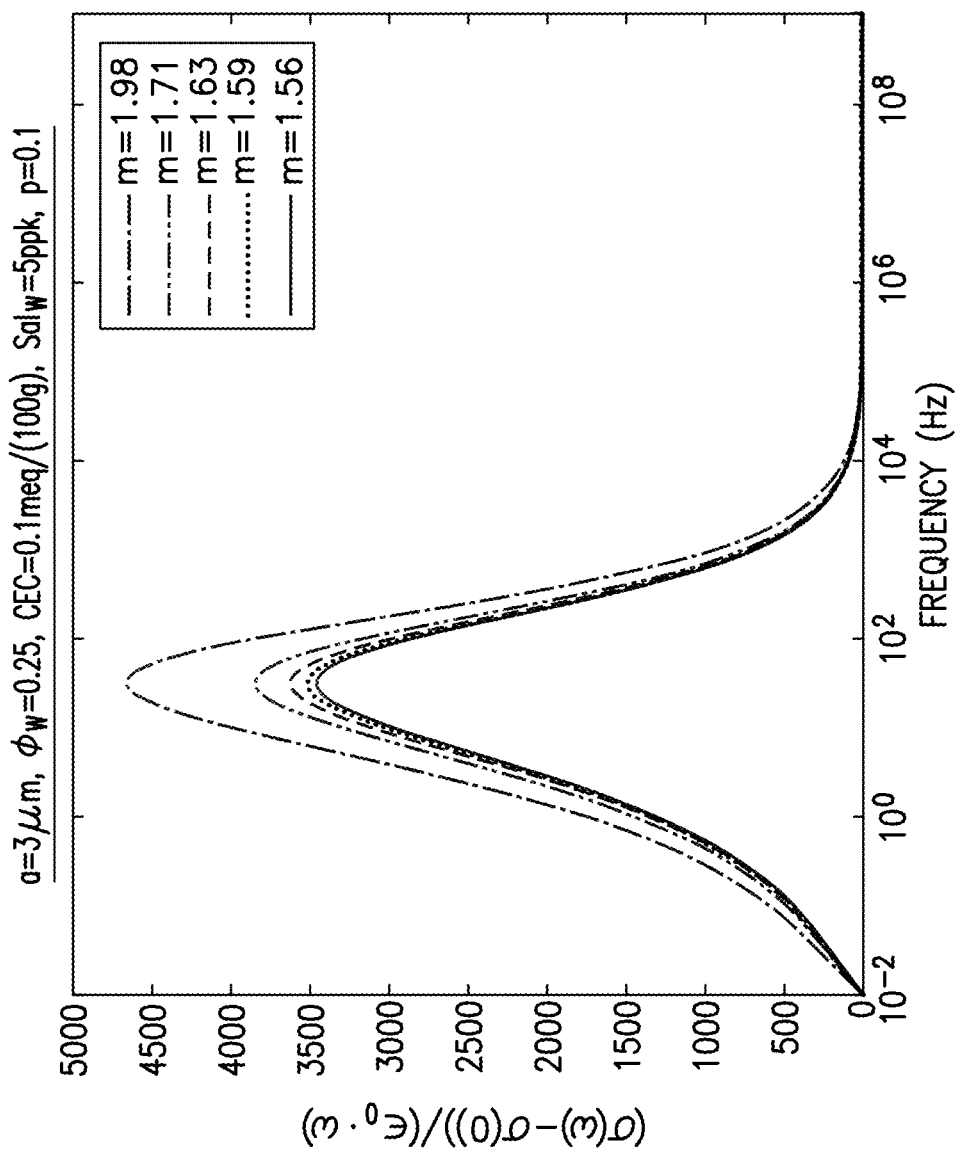

The effect of changing the cementation exponent m on wideband EM response data is shown in FIGS. 4a and 4b. The change of the cementation exponent m reflects a change in conductivity of a rock sample and hence, a change in the shape of non-charged spheriodal particles. Note that the change in the cementation exponent m (and the corresponding change in shape of non-charged spheroidal particles) does not impact the characteristic frequency of the low-frequency relaxation and has minimal effect on the low-frequency permittivity enhancement, which is dominated in this range by the electrical double layer response.

Figure 5A:
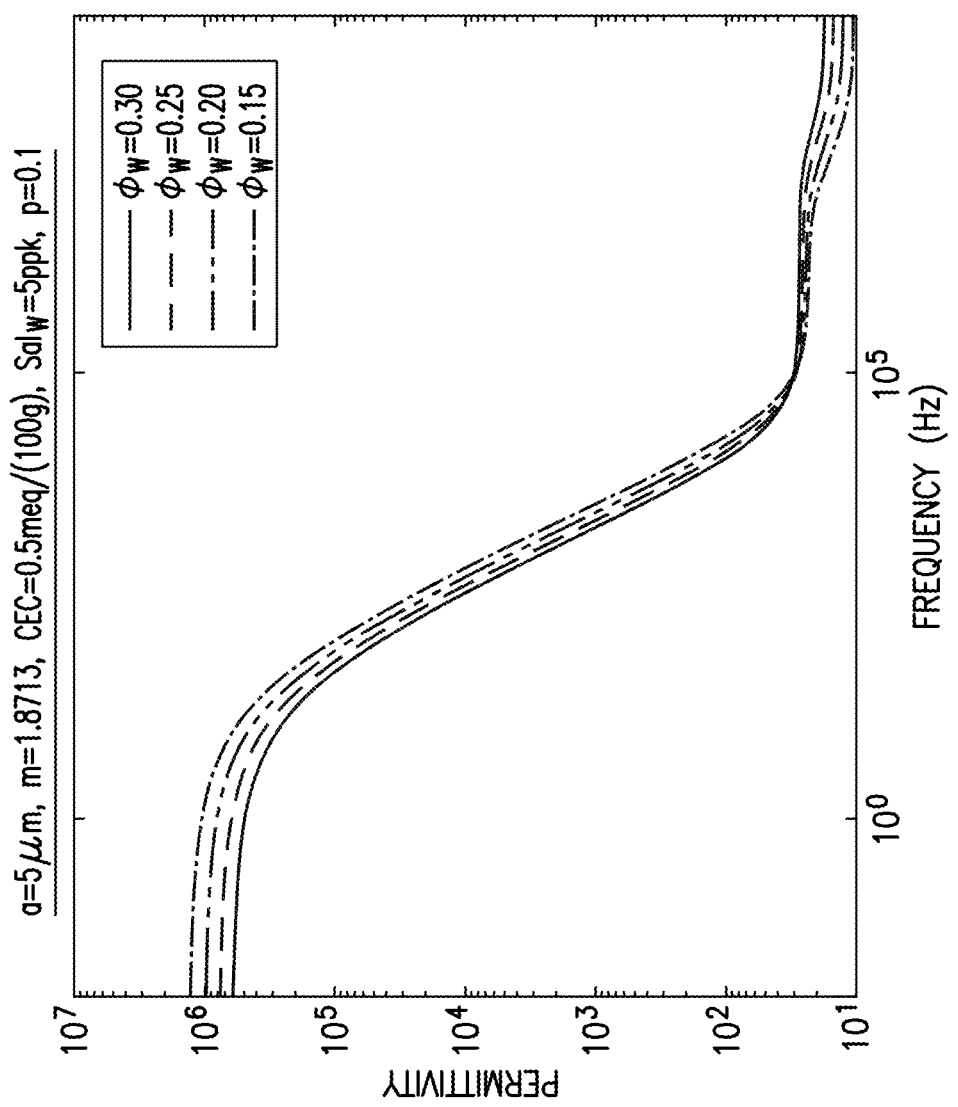
FIGS. 5a and 5b are plots of the response of the wideband grain polarization model that shows the dependence of permittivity with respect to frequency for changing water-filled porosity $\phi_w$ (FIG. 5a) and the dependence of conductivity with respect to frequency for changing water-filled porosity $\phi_w$ (FIG. 5b).
Figure 5B:
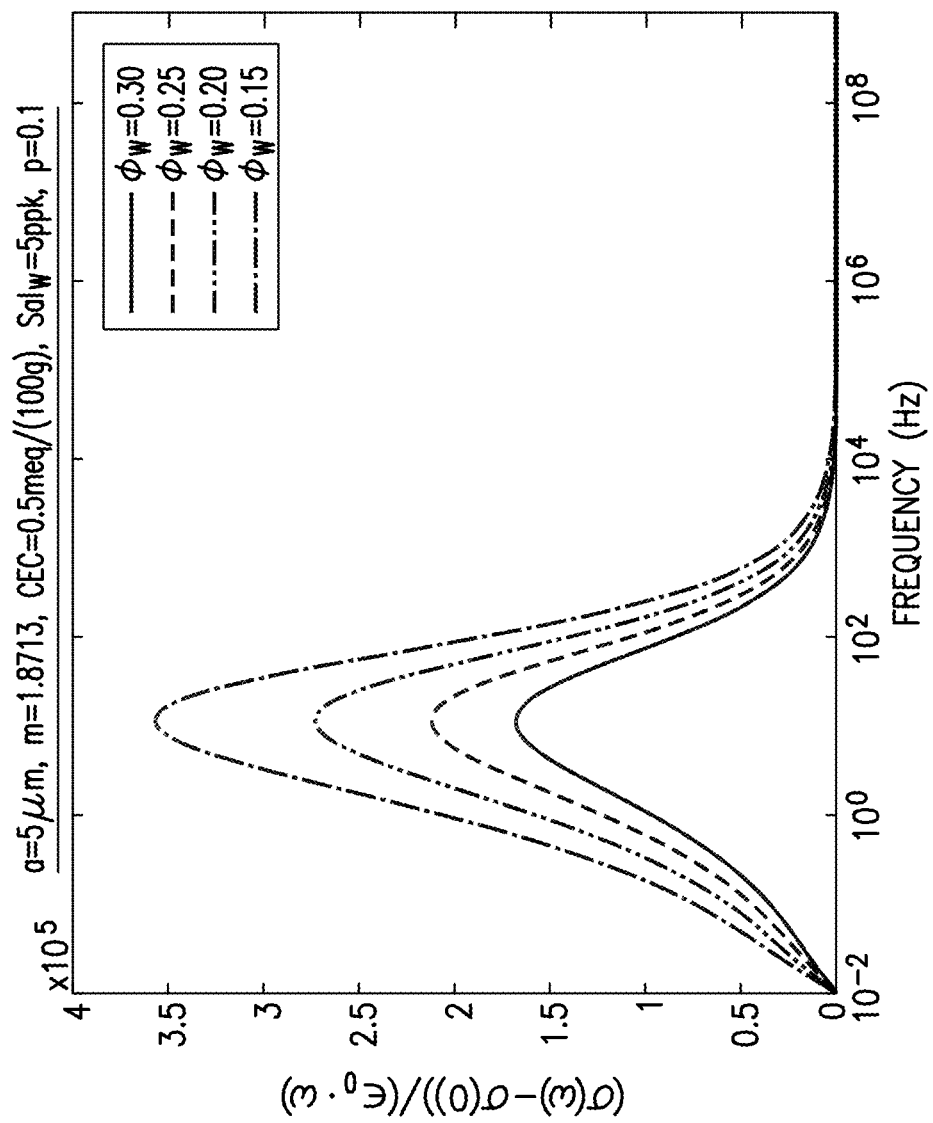

The effect of variation in water-filled porosity $\phi_w$ on wideband EM response data is shown in FIGS. 5a and 5b. The main effects of increasing water-filled porosity $\phi_w$ is the increase in the real part of the permittivity in the high-frequency range. Increase in water-filled porosity $\phi_w$ also leads to a decrease of the permittivity in the low-frequency range. Increase in water-filled porosity $\phi_w$ also reduces the peak amplitude of the conductivity peak. It should be noted that effects of increasing water-filled porosity $\phi_w$ and water salinity $Sal_w$ are similar and can compensate each other at the low-frequency range. As a result, inversion for both salinity and porosity from solely low frequency signals will not be stable as demonstrated hereinafter.

Figure 6:
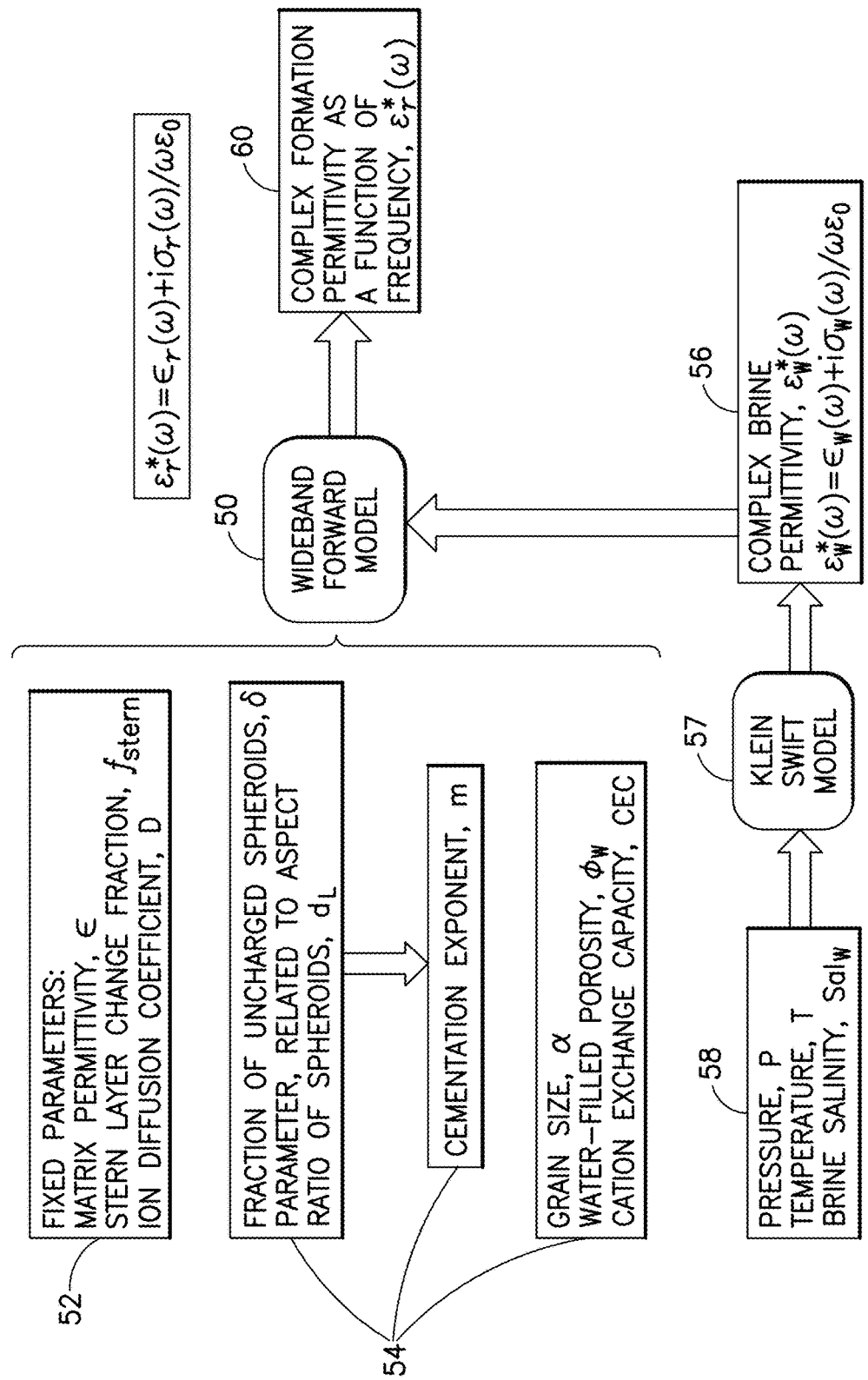
FIG. 6 is a diagram showing the input parameters and the outputs of a wideband forward model.

In one aspect, a wide-band inversion on synthetic data was conducted as described hereinafter. The synthetic data was simulated by varying the following model parameters: water-filled porosity ($\phi_w$), cation exchange capacity (CEC), fraction of the spheroidal inclusions (p), a parameter related to the aspect ratio of spheroids ($d_L$), the grain size (a), and the water salinity ($Sal_w$). The cementation exponent, m, can be calculated from these model parameters. The wideband inversion used the wideband model that was previously presented. As shown in FIG. 6, the input parameters into the wideband model 50 include fixed parameters 52 such as the matrix permittivity ($\varepsilon_m$), the Stern layer charge fraction $f_{stern}$, and the ion diffusion coefficient D, as well as the previously mentioned varying parameters 54, and the frequency dependent complex brine permittivity ($\varepsilon^*_w(\omega)$) 56. The complex brine permittivity is obtained from a Klein-Swift or other water model 57 which utilizes known variable inputs 58 such as pressure P, temperature T, and brine salinity $Sal_w$. The complex brine permittivity is calculated according to $\varepsilon_w^*(\omega)=\varepsilon_w(\omega)+i\sigma_w(\omega)/\omega\varepsilon_0$. The output 60 of the forward model 50 is the complex formation permittivity as a function of frequency, $\varepsilon_r^*(\omega)=\varepsilon_r(\omega)+i\sigma_r(\omega)/\omega\varepsilon_0$.

Laboratory or downhole measurements provide wideband complex formation permittivity as a function of frequency. The target of petrophysical evaluation is to obtain input model parameters from the measured formation response. In one aspect, direct analytical solution to derive input parameter is difficult for the wideband model as described above. Thus, according to one embodiment, an inversion approach can be adopted where unknown model parameters are derived by iteratively changing input model parameters to minimize discrepancy or difference between the measured formation response and the predicted formation response. In each iteration, the predicted formation response is determined by applying the input model parameters to the wideband model. The difference between the measured and predicted formation response can be described by a cost function C that can be defined as $$C=(\Sigma_{j=1}^{N}[(W_j(\varepsilon_{model,j}\varepsilon_{r,j})/\Delta\varepsilon_{r,j})^2+(W_j(\sigma_{model,j}\sigma_{r,j})/\Delta\sigma_{r,j})^2])^{0.5} \quad (19)$$

where N is the number of frequency points measured over the wideband frequency range, $\varepsilon_{r,j}$ the measured real part of the formation permittivity at the j-th frequency, $\varepsilon_{model,j}$ is the predicted with the forward model real part of the formation permittivity at the j-th frequency, $\Delta\varepsilon_{r,j}$ is the measurement uncertainty in the measured real part of the formation permittivity at the j-th frequency, $\sigma_{r,j}$ is the measured real part of the formation conductivity at the j-th frequency, $\sigma_{model,j}$ is the predicted with the forward model real part of the formation conductivity at the j-th frequency, $\Delta\sigma_{r,j}$ is the measurement uncertainty in the measured real part of the formation conductivity at the j-th frequency. In addition, weight parameters $0<W_j<1$ can be introduced to give different weight on measurements at different frequencies, which are employed to obtain optimum inversion results.

At low frequencies, it is often easier to measure or compute the impedance phase angle θ instead of the real permittivity. In that case, the cost function can be written as $$C=(W\Sigma_{j=1}^{N_{lf}}[((\theta_{model,j}\theta_{r,j})/\Delta\theta_{r,j})^2+((\sigma_{model,j}\sigma_{r,j})/\Delta\sigma_{r,j})^2]+\Sigma_{j=1}^{N_{hf}}[((\varepsilon_{model,j}\varepsilon_{r,j})/\Delta\varepsilon_{r,j})^2+((\sigma_{model,j}\sigma_{r,j})/\Delta\sigma_{r,j})^2])^{0.5} \quad (20)$$

where $\theta_{model,j}$ and are the predicted and measured impedance phase angles, respectively, $N_{lf}$ is the number of low-frequency data points, $N_{hf}$ is the number of high-frequency data points, and W is the weight factor for the low-frequency data. In this equation for the cost function, the first summation is over the low frequency data points, and the second summation is over the high frequency data points. It is noted that if two different models are being used for the high and low frequency ranges as described below and illustrated in FIGS. 16(c) and 16(d), then these two cost functions can still be used, but the predicted values for the permittivity, conductivity and phase shift will come from the different models depending on the frequency range.

Figure 7:
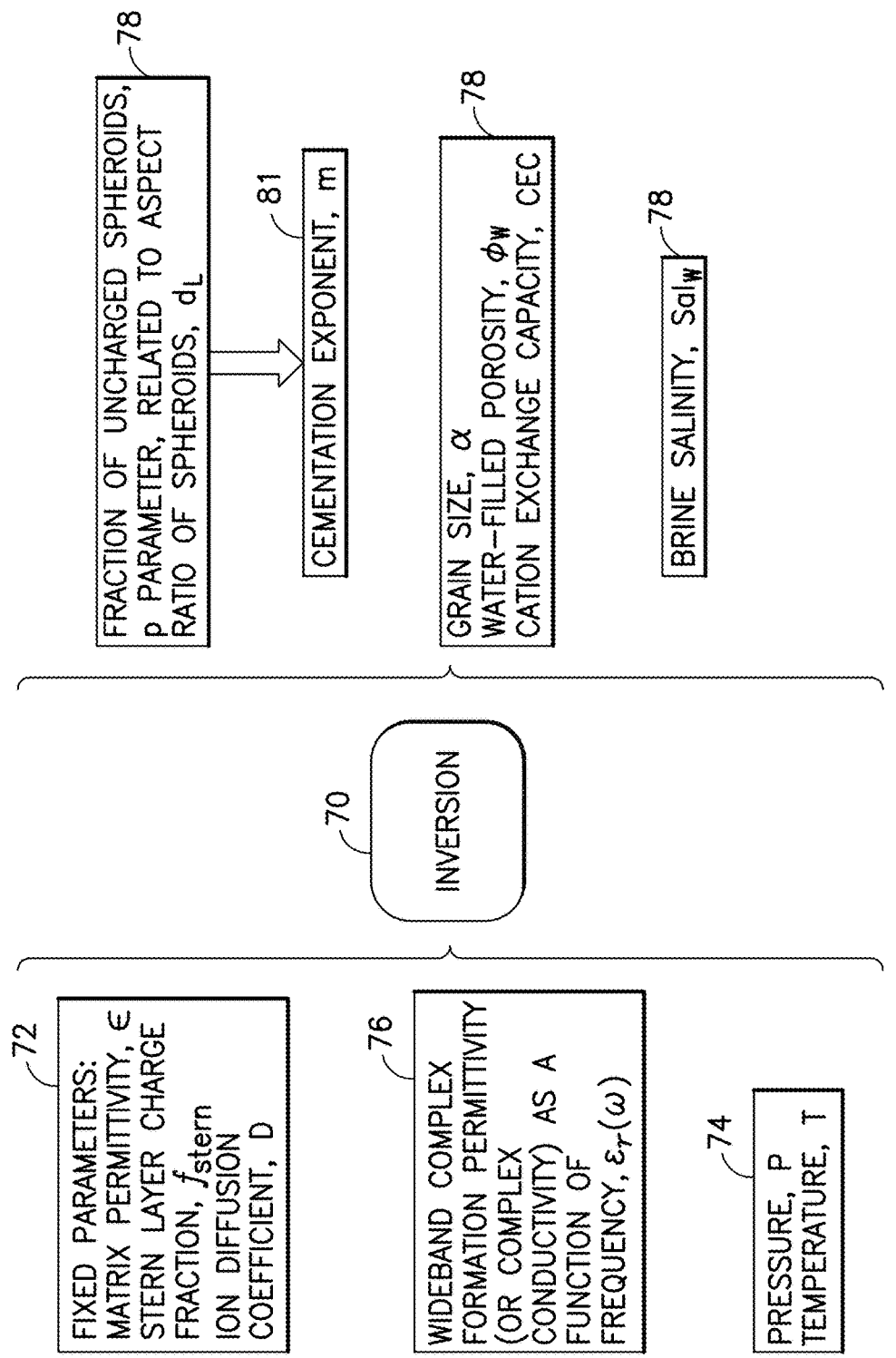
FIG. 7 is a diagram showing the input and output parameters and workflow of a wideband EM inversion.

The goal of the wideband inversion procedure is to minimize the value of the cost function by adjusting input model parameters. The inputs and produced outputs of the wideband data inversion 70 are shown in FIG. 7, including fixed parameters inputs 72 such as matrix permittivity (typically determined using a borehole neutron tool or other borehole tool), Stern layer charge fraction, ion diffusion coefficient, measured parameter inputs 74 such as pressure and temperature, and calculated inputs 76 such as the wideband complex formation permittivity or conductivity as a function of frequency. Outputs 78 of the wideband inversion procedure may include the parameters such as grain size a, water-filled porosity $\phi_w$, CEC, water salinity $Sal_w$, the fraction of uncharged spheroids p, and a parameter related to the aspect ratio of spheroids $d_L$. Other parameters such as the cementation exponent m can be calculated at 80 from the outputs obtained as a result of the wideband inversion procedure. Various algorithms known in the art can be utilized to achieve cost function minimization. See, e.g., Ben-Israel, A. "A Newton-Raphson Method for the Solution of Systems of Equations," Journal of Mathematical Analysis and Applications, Vol. 15(2), 1966, pp. 243-252; and Moré', J. J., "The Levenberg-Marquardt Algorithm: Implementation and Theory", Numerical Analysis, Springer Berlin Heidelberg, 1978, pp. 105-116. Other cost functions or weighting schemes in respect to measurement uncertainty can be employed to obtain optimum inversion results.

To demonstrate robustness, an inversion was performed on synthetic data with noise. Two datasets were generated having the same noise levels at the high frequency range but different noise levels at the low frequency range. The noise level was defined as a percentage of the signal amplitude.

The synthetic high-frequency signals contain the permittivity and conductivity data at four frequencies spanning the range from 20 MHz to 1 GHz, which are analogous to the data provided by existing dielectric dispersion logging tools. The noise level added to the permittivity data starting from the lowest frequency to the highest frequency in the high-frequency range was 5%, 2.5%, 1.5%, and 1.5% correspondingly. The noise level added to the conductivity data starting from the lowest frequency to the highest frequency was 1.5%, 1.5%, 1.5%, and 1.5% correspondingly.

The synthetic low-frequency signals contain the twelve logarithmically spaced conductivity and phase data points between 1 mHz and 12.6 KHz. In the first data set 1% of noise was added to each conductivity data point and 1.5% of noise to each phase data point. The second generated dataset had a higher noise level with 2% of noise added to each conductivity data point and 2.5% of noise to each phase data point.

Figure 8A:
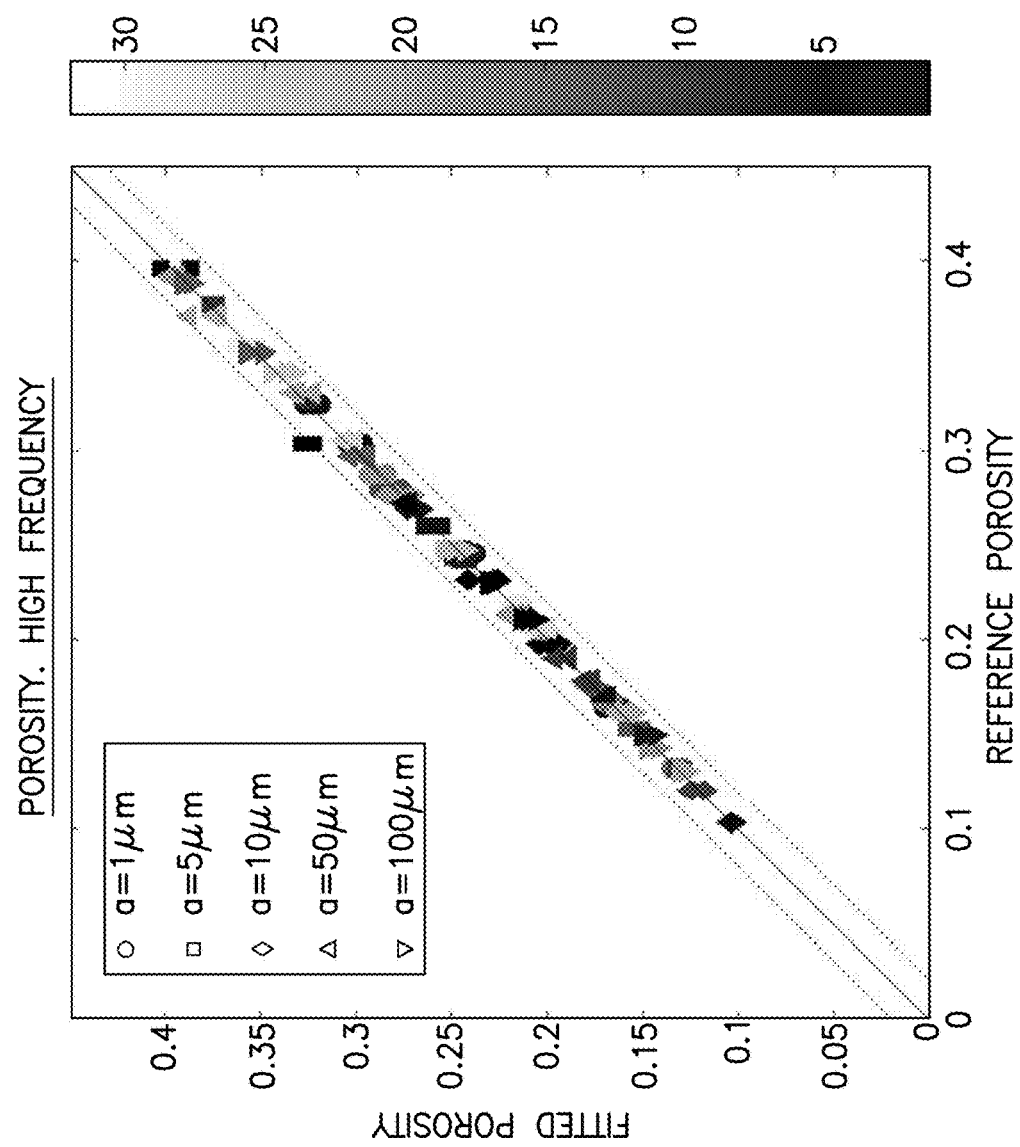
Figure 8B:
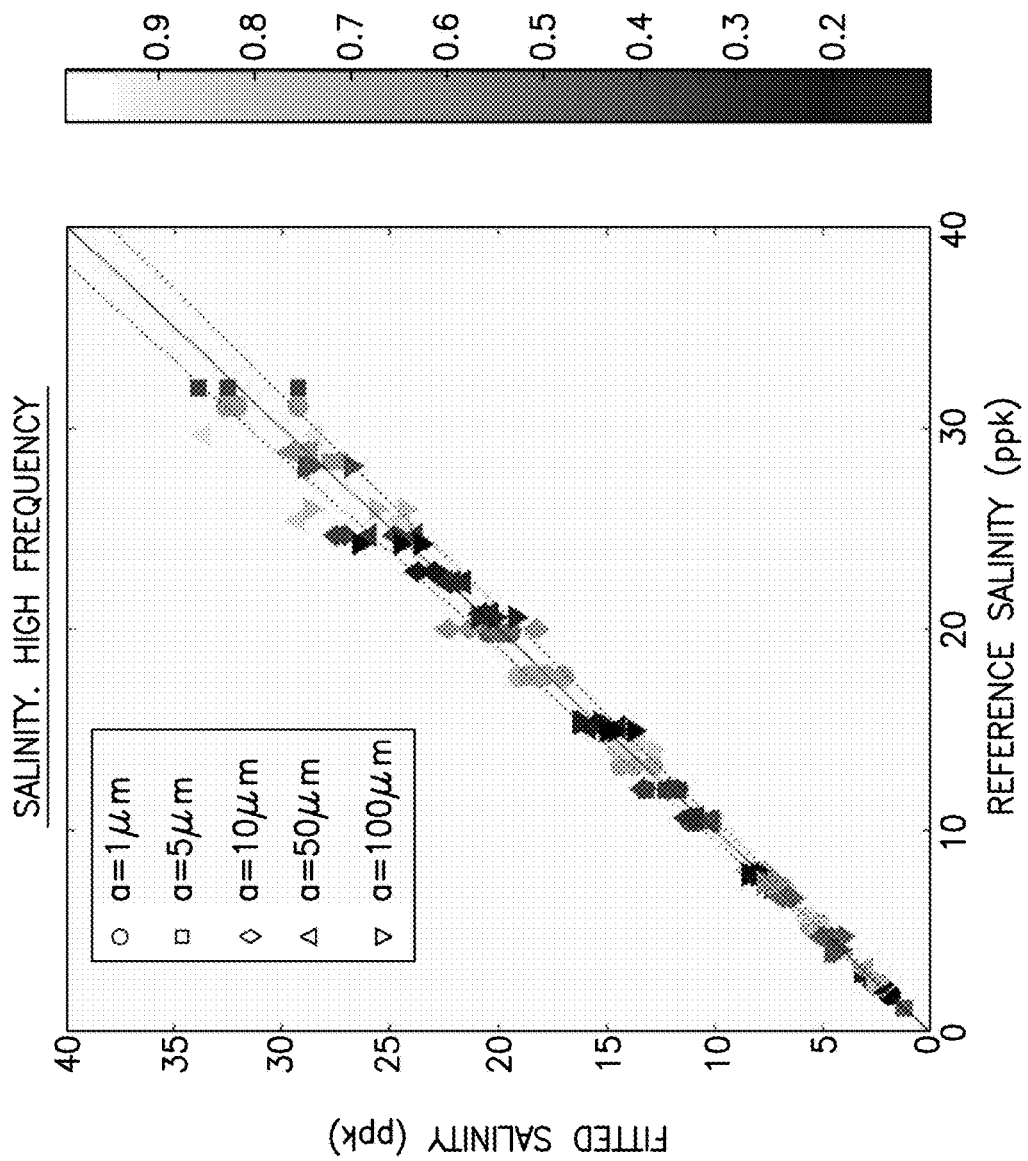

Individual inversions for the low-frequency data and for the high-frequency data were conducted. Each individual frequency range has sensitivity to a limited number of parameters and all six model parameters cannot be simultaneously evaluated from either the high- or low-frequency data alone. The high-frequency data was inverted for the following variables: water-filled porosity ($\phi_w$), water salinity (Sal$_w$), the parameter related to the aspect ratio of spheroids (d$_L$), and fraction of spheroidal inclusions (p). The cementation exponent (m) is then computed from equation (11) with the inverted values of d$_L$ and p. The inversion results for the first set of data are shown in FIGS. 8a-8c with FIG. 8a showing a comparison of calculated (via inversion) water-filled porosity $\phi_w$ versus actual or true water-filled porosity $\phi_w$, FIG. 8b showing a comparison of calculated (via inversion) water salinity Sal$_w$ versus actual water salinity Sal$_w$, and FIG. 8c showing a comparison of the calculated (via inversion) cementation exponent m versus the actual cementation component m, all for various grain sizes. The inversion results for the second set of high frequency data are similar to the first set of data and are not shown here. Scatter in the inverted parameters compared to the true values increases with increasing noise in the data. It is apparent that the grain size parameter cannot be obtained from the high-frequency data as the dependence on grain size drops out at high frequencies in the model.

Figure 9A:
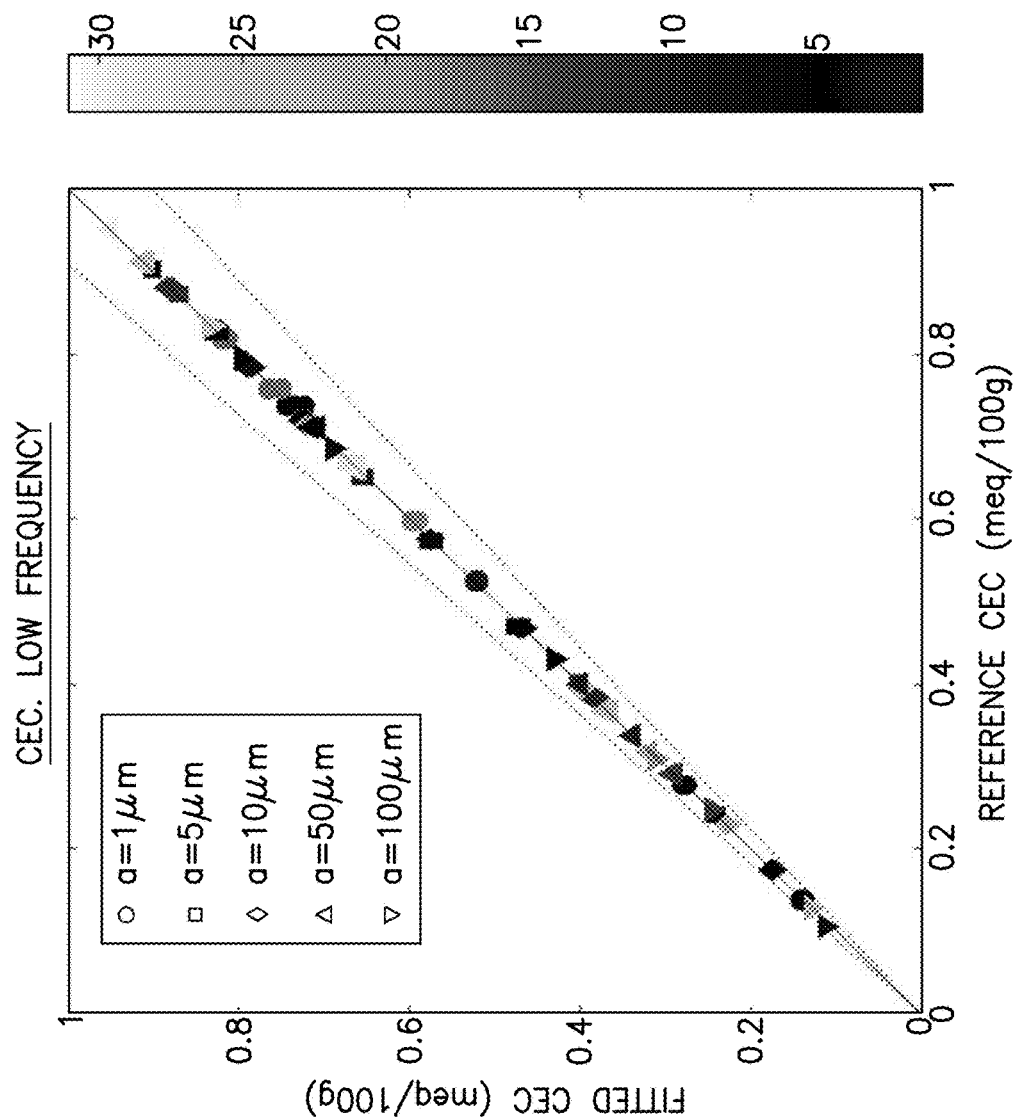
FIGS. 9a-9c are plots showing three parameters inverted from low-frequency data; the three parameters include CEC (FIG. 9a), cementation exponent m (FIG. 9b) and charged grain size a (FIG. 9c); the plots show the inverted values for these three parameters versus the true or actual values for these three parameters for comparison purposes.
Figure 9B:
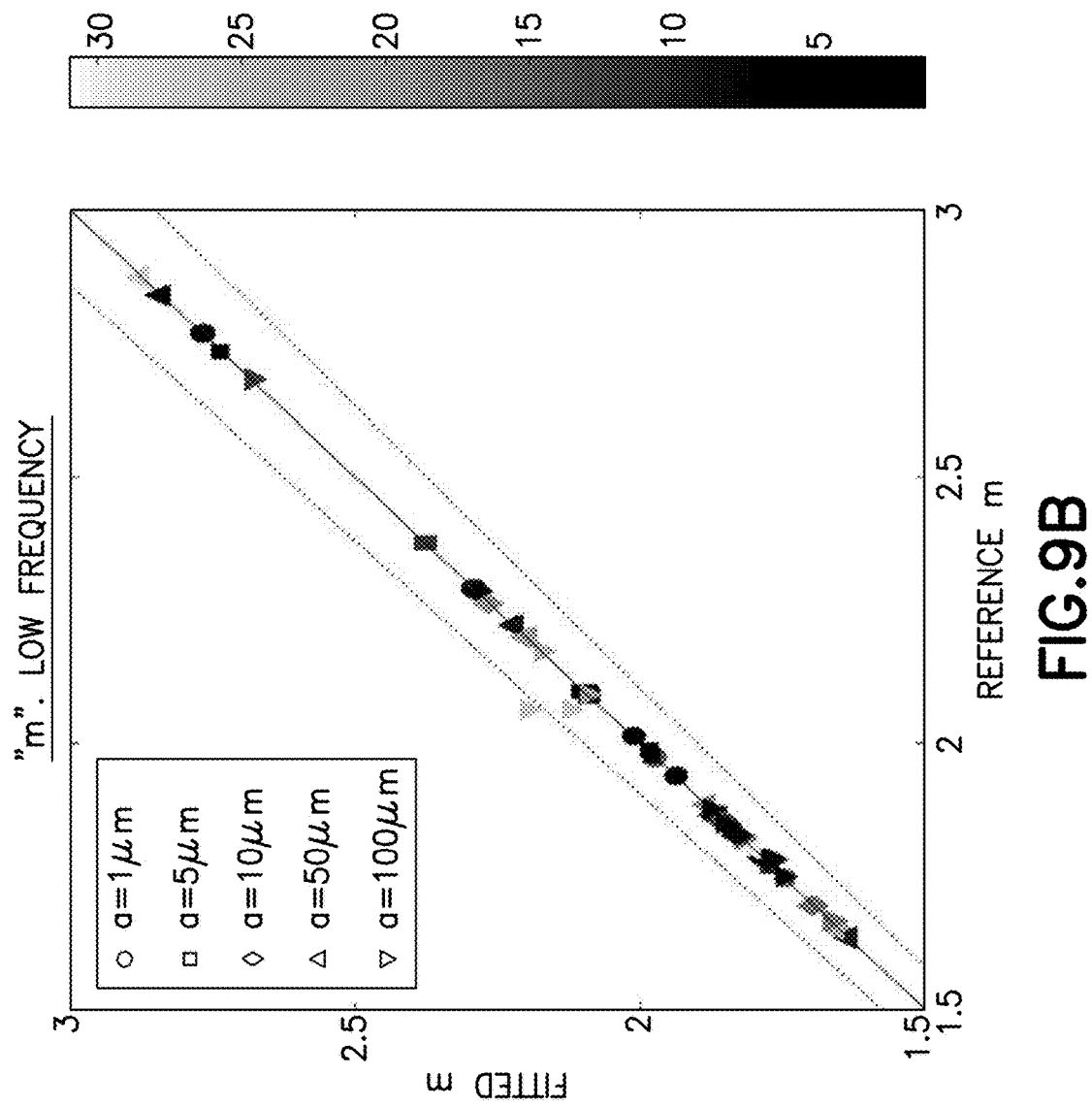
Figure 9C:
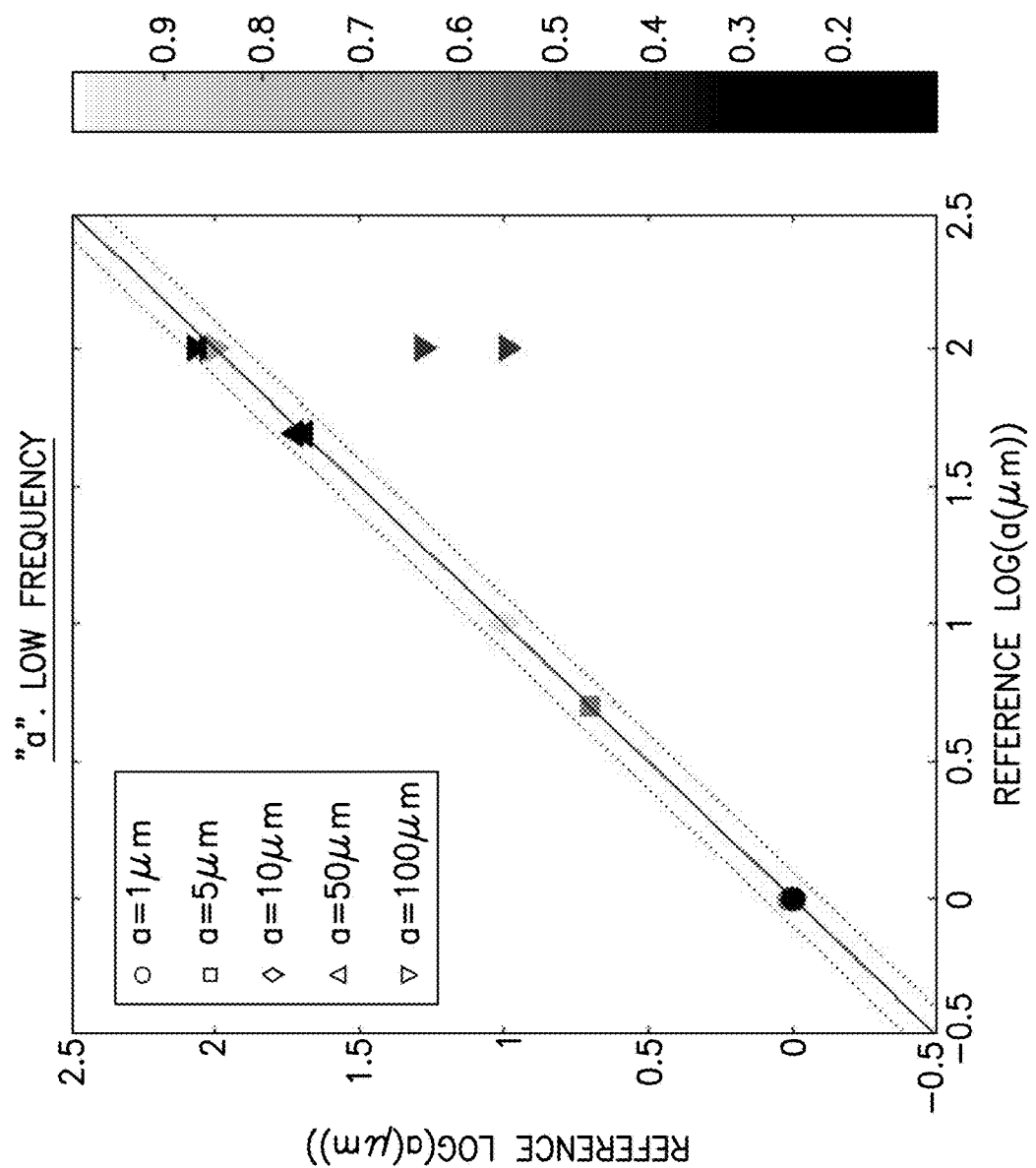

In a similar manner, low-frequency data was inverted for the following unknowns: CEC, the parameter related to the aspect ratio of spheroids (d$_L$), and grain size a. Water salinity (Sal$_w$), water-filled porosity ($\phi_w$), fraction of spheroids (p), matrix permittivity and temperature are provided as inputs. Again, the cementation exponent (m) is then computed from equation (11) with the inverted d$_L$ and the volume fraction of spheroids. The inversion results for the lower noise dataset is shown in FIGS. 9a-9c with FIG. 9a showing a comparison of the inversion results for CEC versus the true CEC, FIG. 9b showing a comparison of the inversion results for the cementation exponent m versus the true cementation exponent m, and FIG. 9c showing a comparison of the inversion results for a function of the grain size versus a function of the true grain size, all for various grain sizes. As seen from FIGS. 9a-9c, the inversion was capable of reconstructing three unknowns with good accuracy.

Figure 10A:
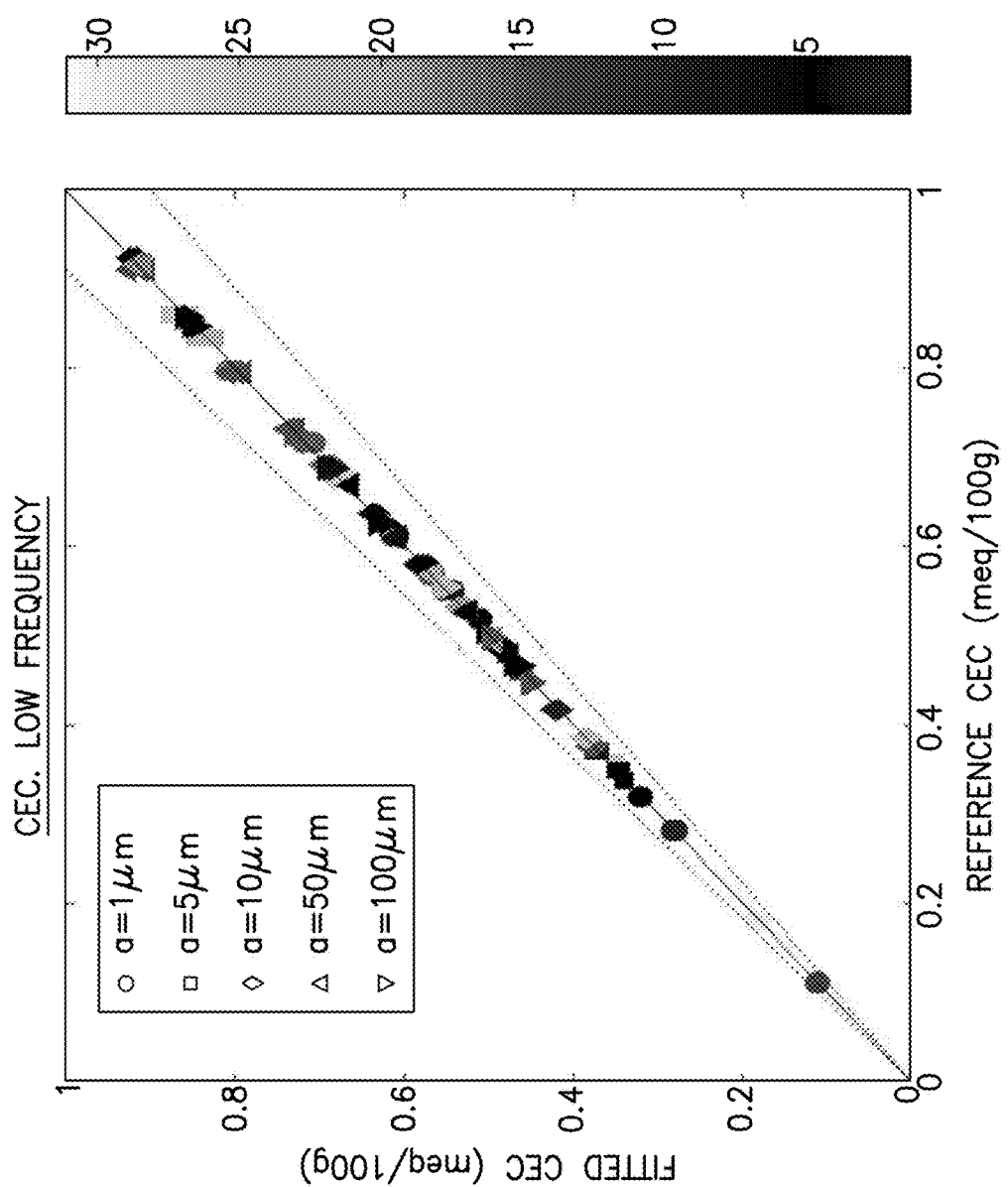
FIGS. 10a-10c are plots showing three parameters inverted from low-frequency data with a higher noise level than for FIGS. 9a-9c; the three parameters include CEC (FIG. 10a), cementation exponent m (FIG. 10b), and charged grain size a (FIG. 10c); the plots show the inverted values for these three parameters versus the true or actual values for these three parameters for comparison purposes.
Figure 10B:
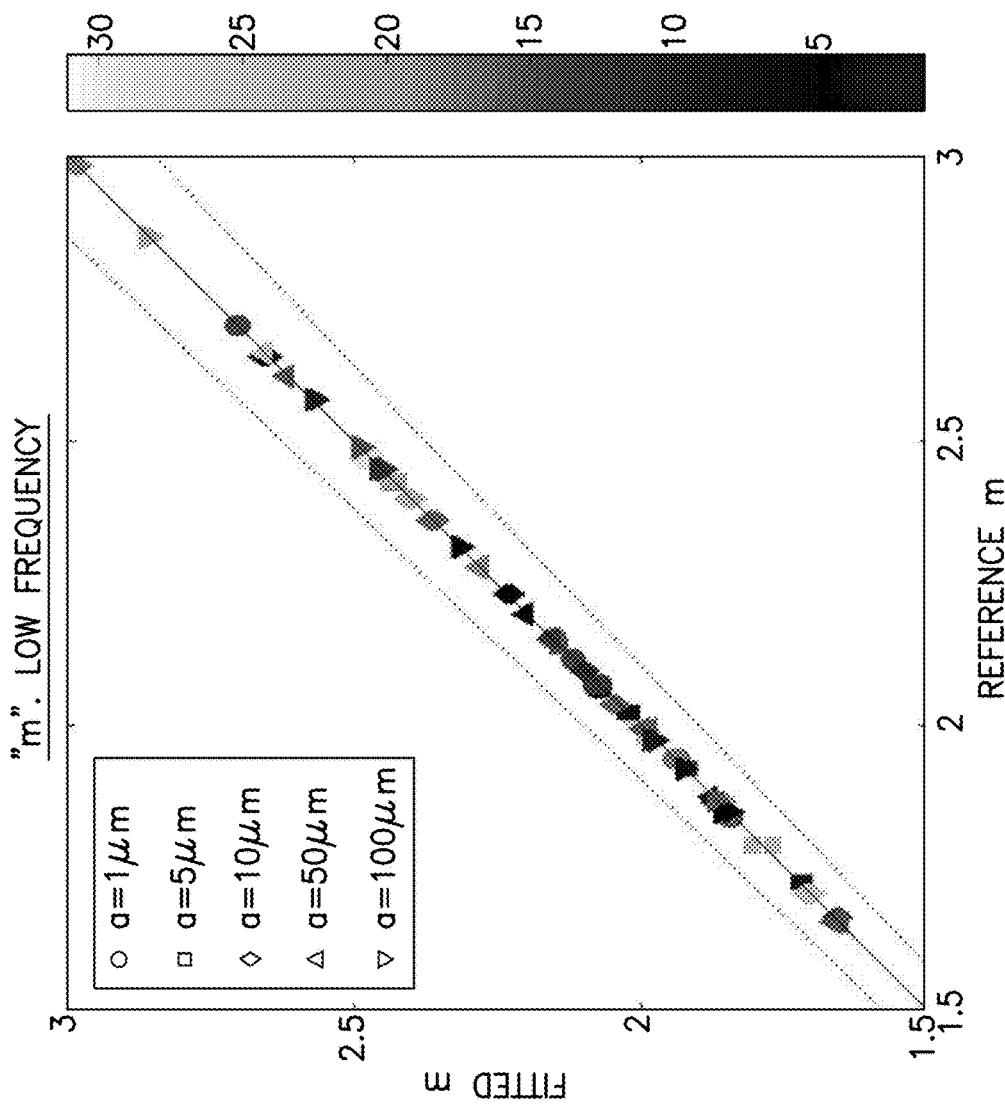
Figure 10C:
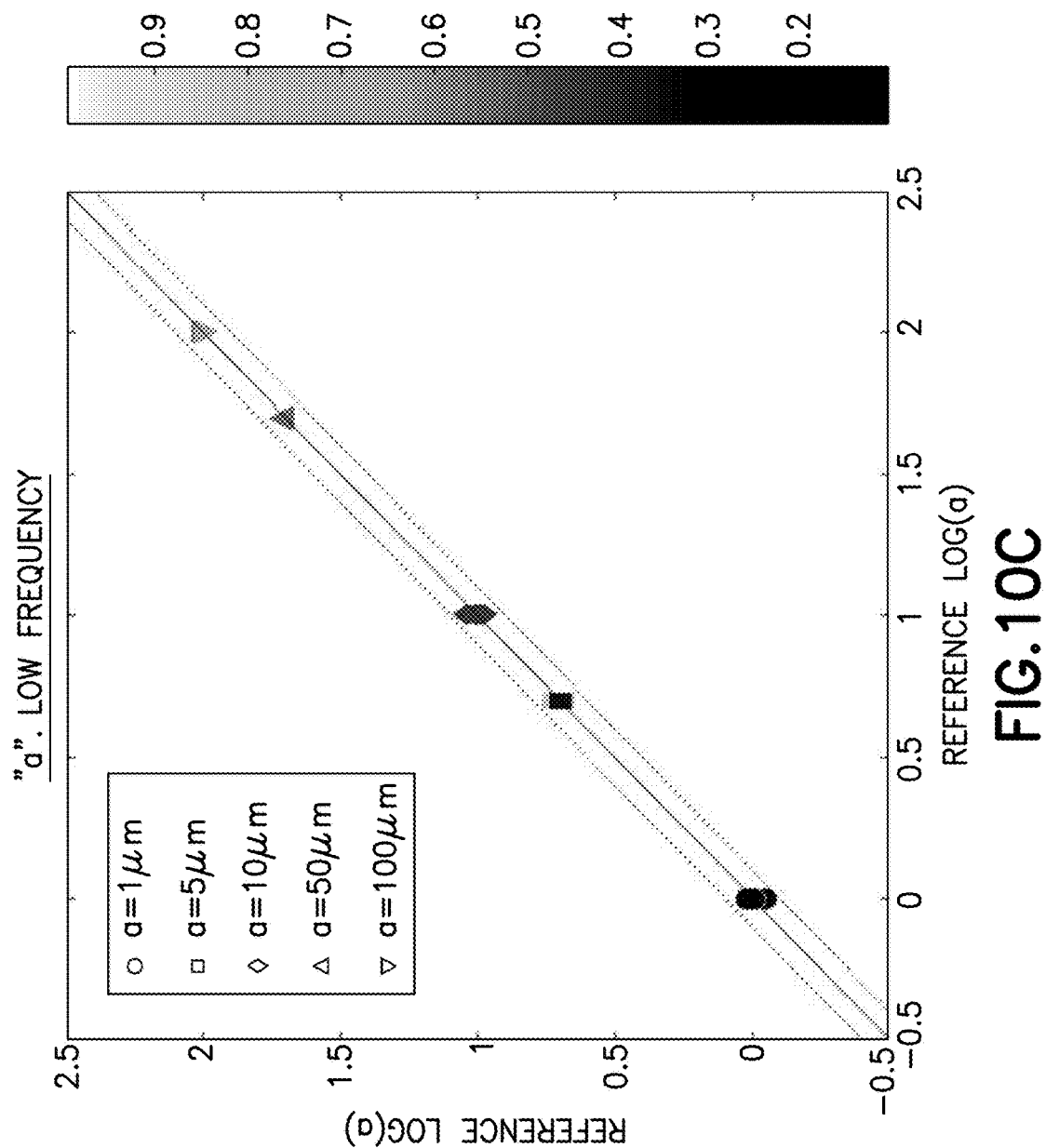
Figure 11A:
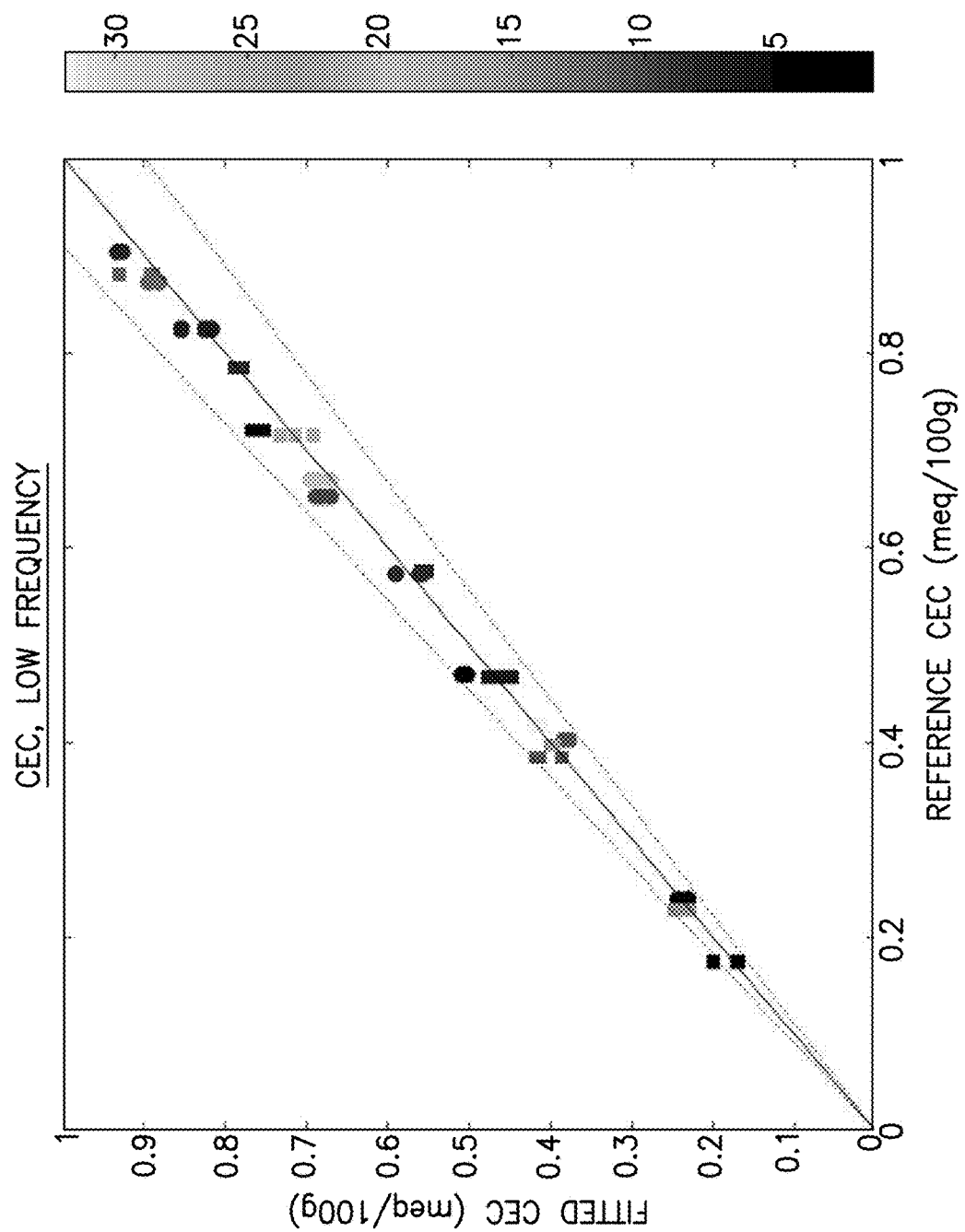
FIGS. 11a-11e are plots showing five parameters inverted from low-frequency data; the five parameters include CEC (FIG. 11a), cementation exponent m (FIG. 11b), water-filled porosity $\phi_w$ (FIG. 11c), charged grain size a (FIG. 11d), and water salinity $Sal_w$ (FIG. 11e); the plots show the inverted values for these five parameters versus the true or actual values for these five parameters for comparison purposes.
Figure 11B:
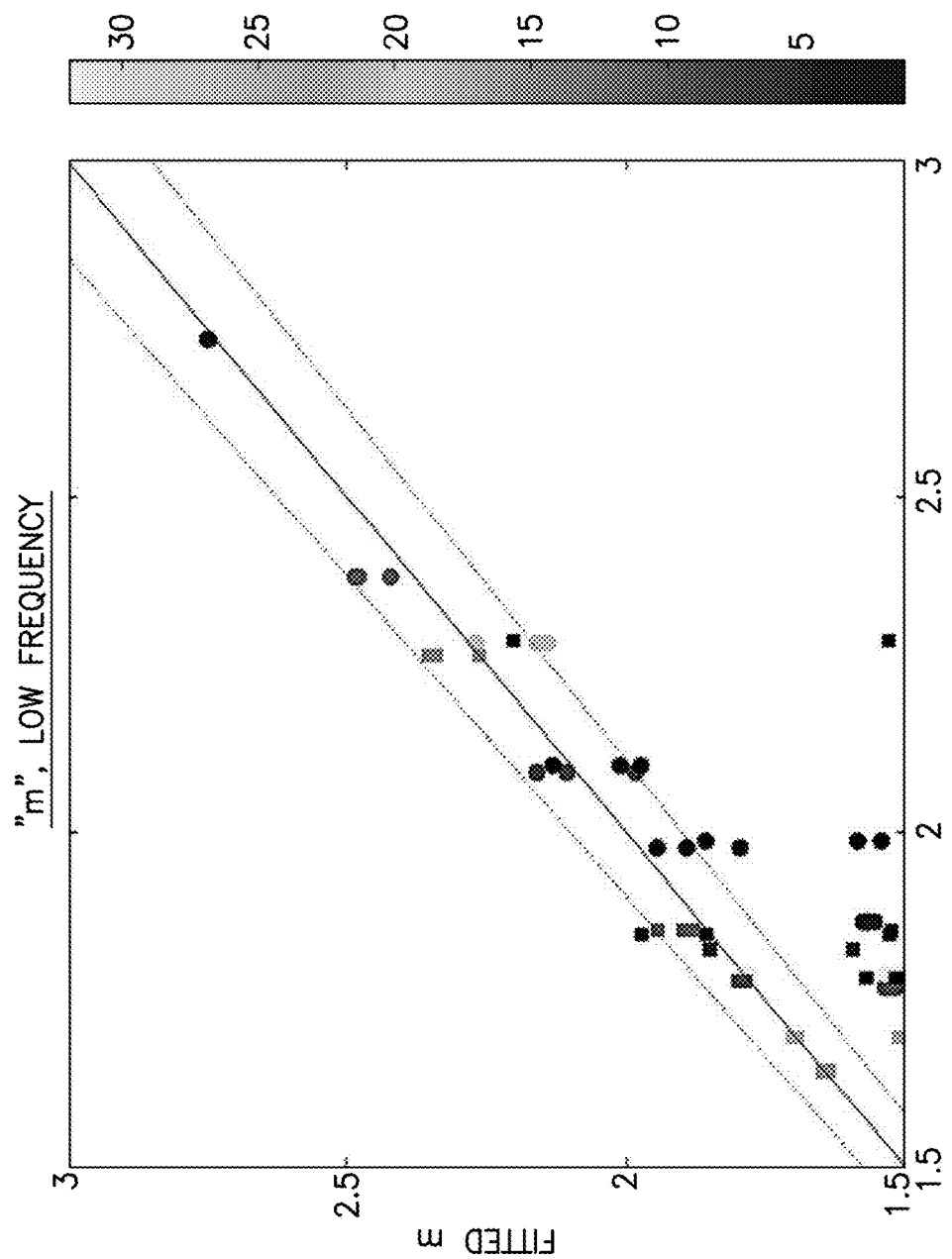
Figure 11C:
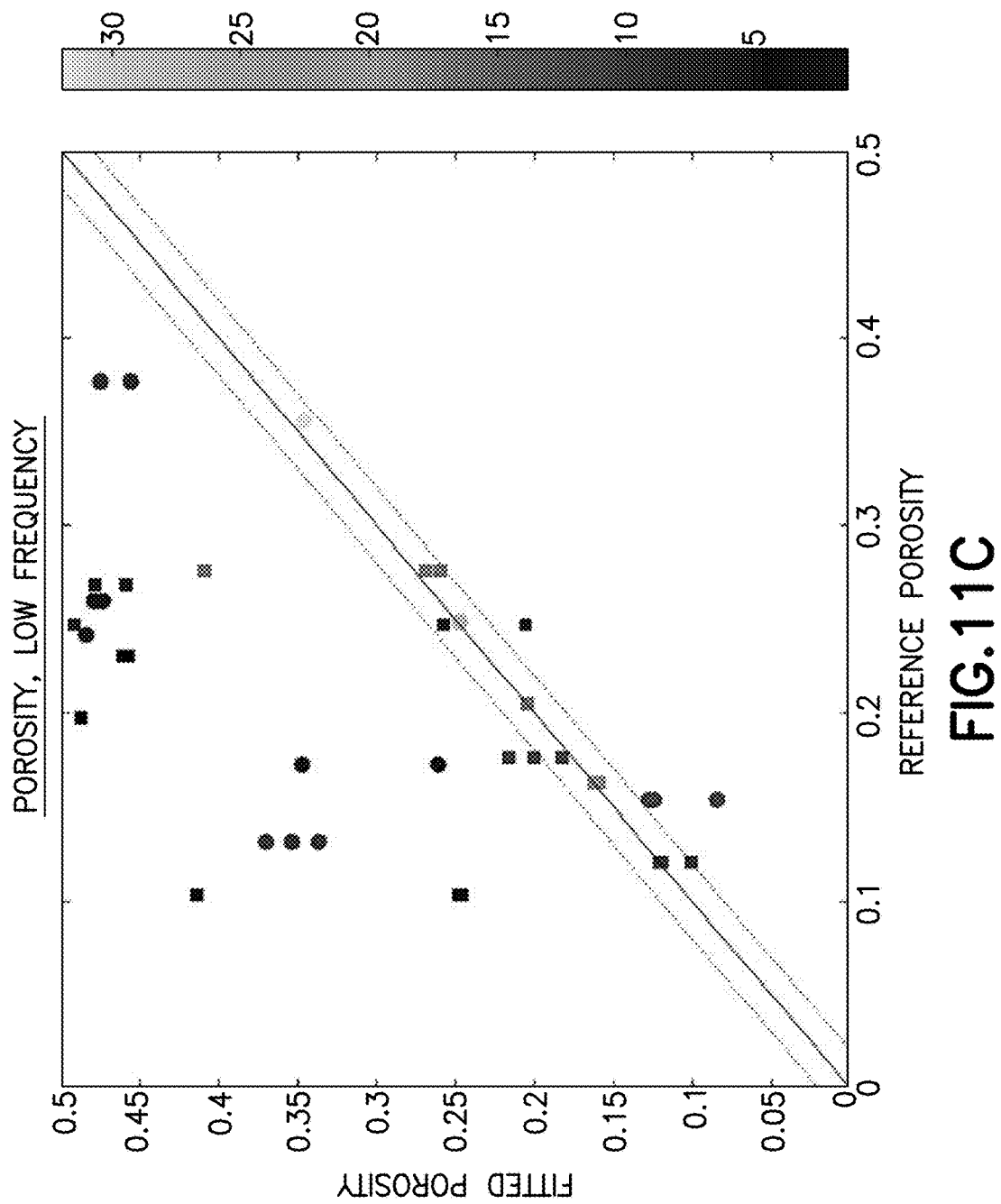
Figure 11D:
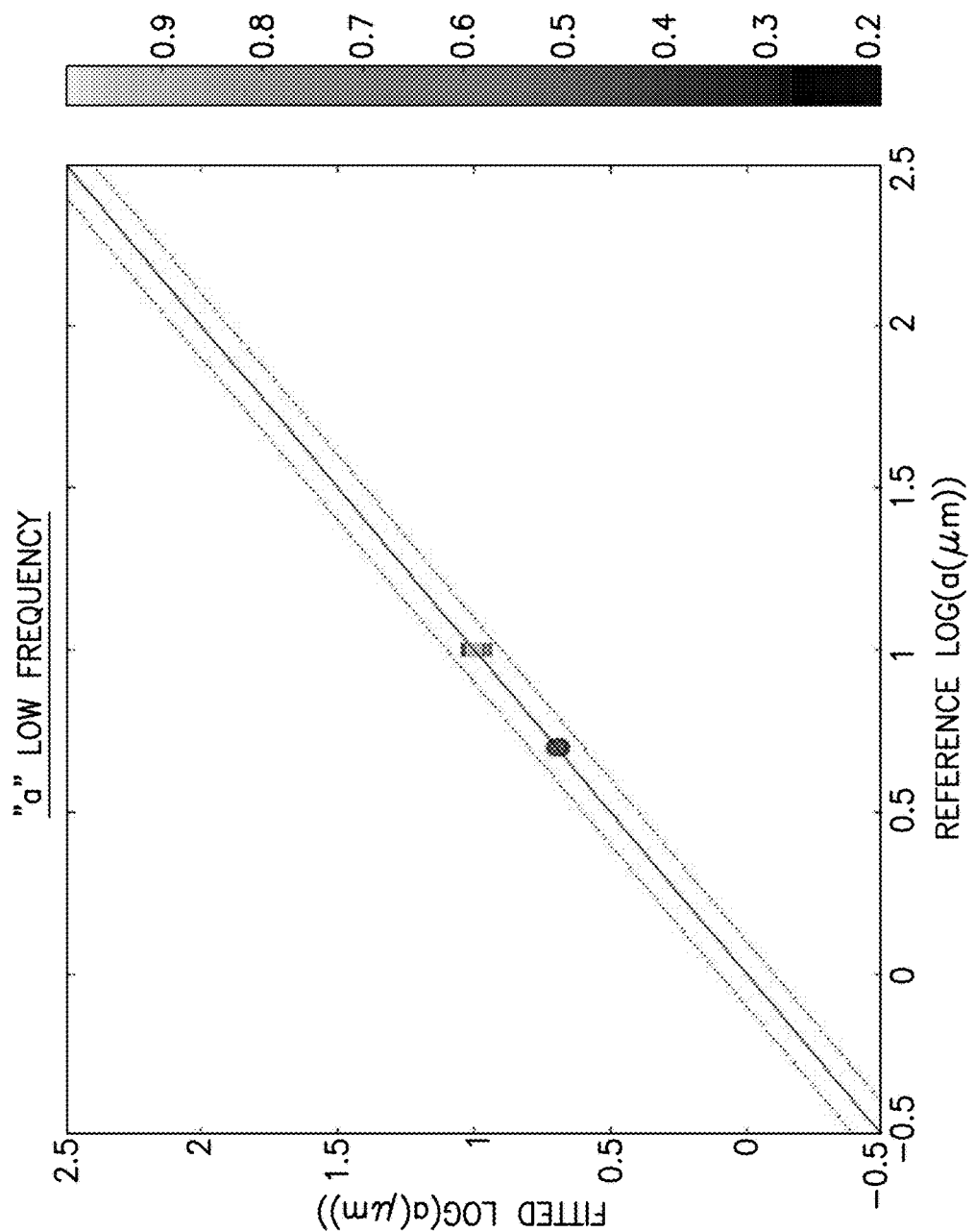
Figure 11E:
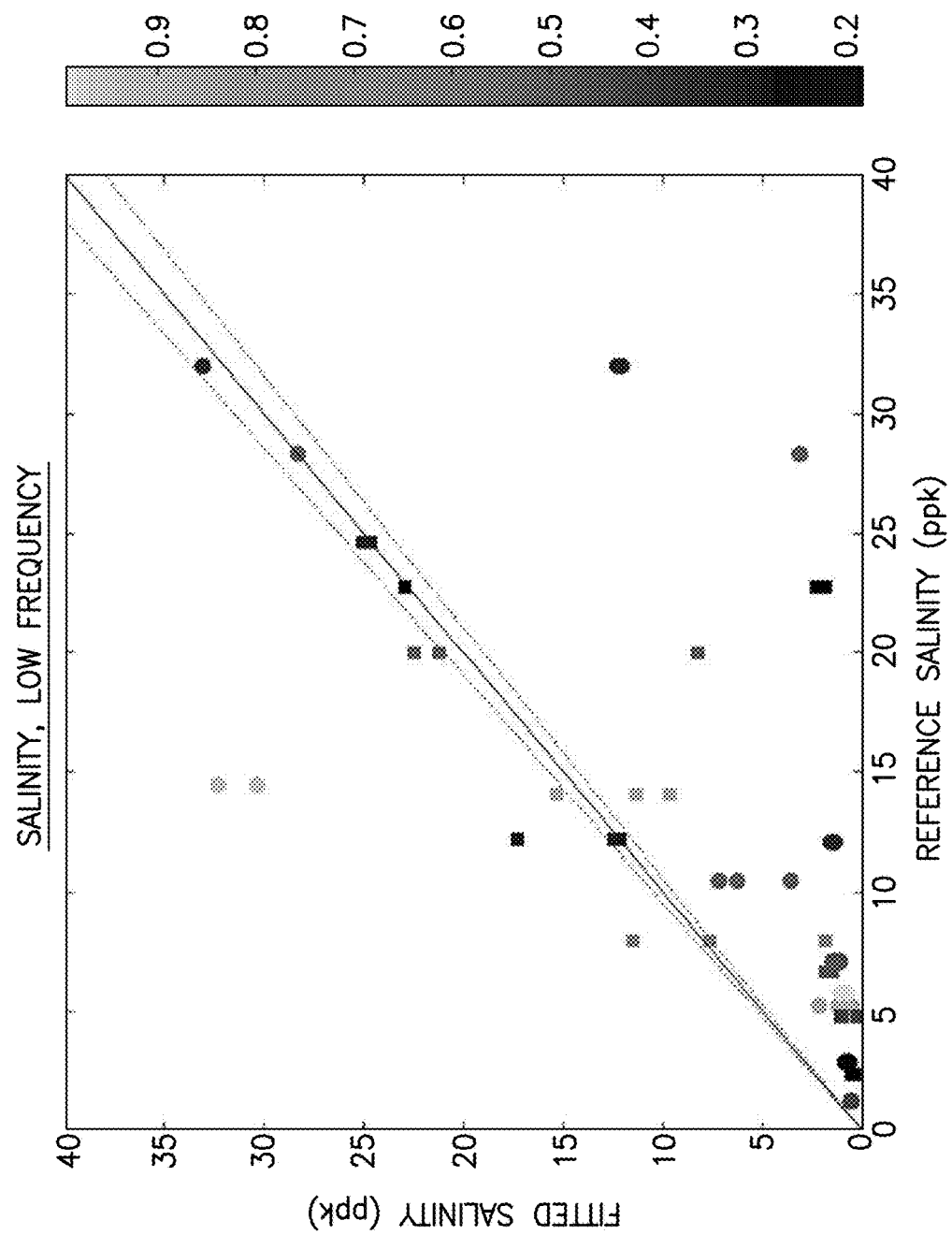
Figure 12A:
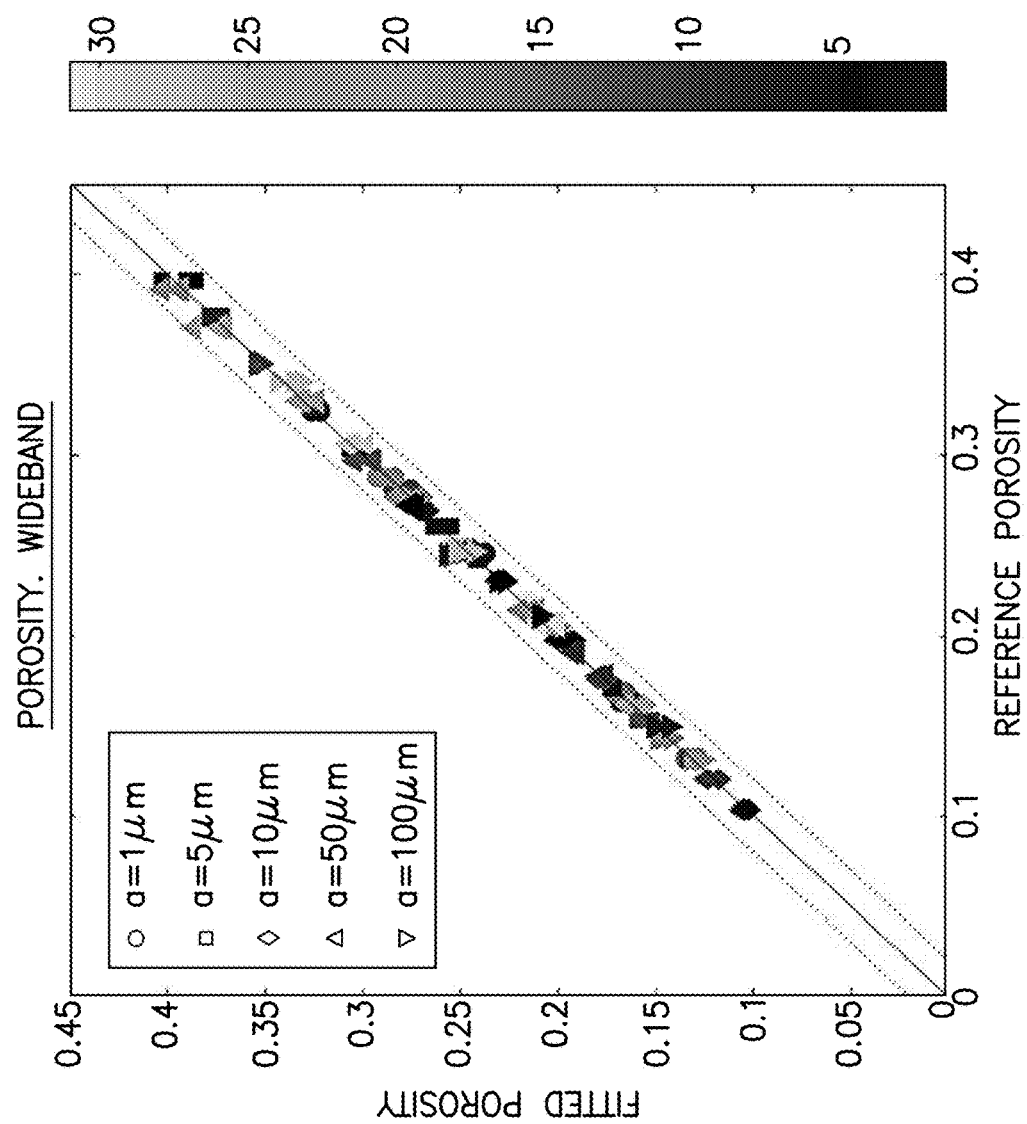
FIGS. 12a-12e are plots showing five parameters inverted from wideband data; the five parameters include water-filled porosity $\phi_w$ (FIG. 12a), water salinity $Sal_w$ (FIG. 12b), cementation exponent m (FIG. 12c), CEC (FIG. 12d), and charged grain radius a (FIG. 12e); the plots show the inverted values for these five parameters versus the true or actual values for these five parameters for comparison purposes.
Figure 12B:
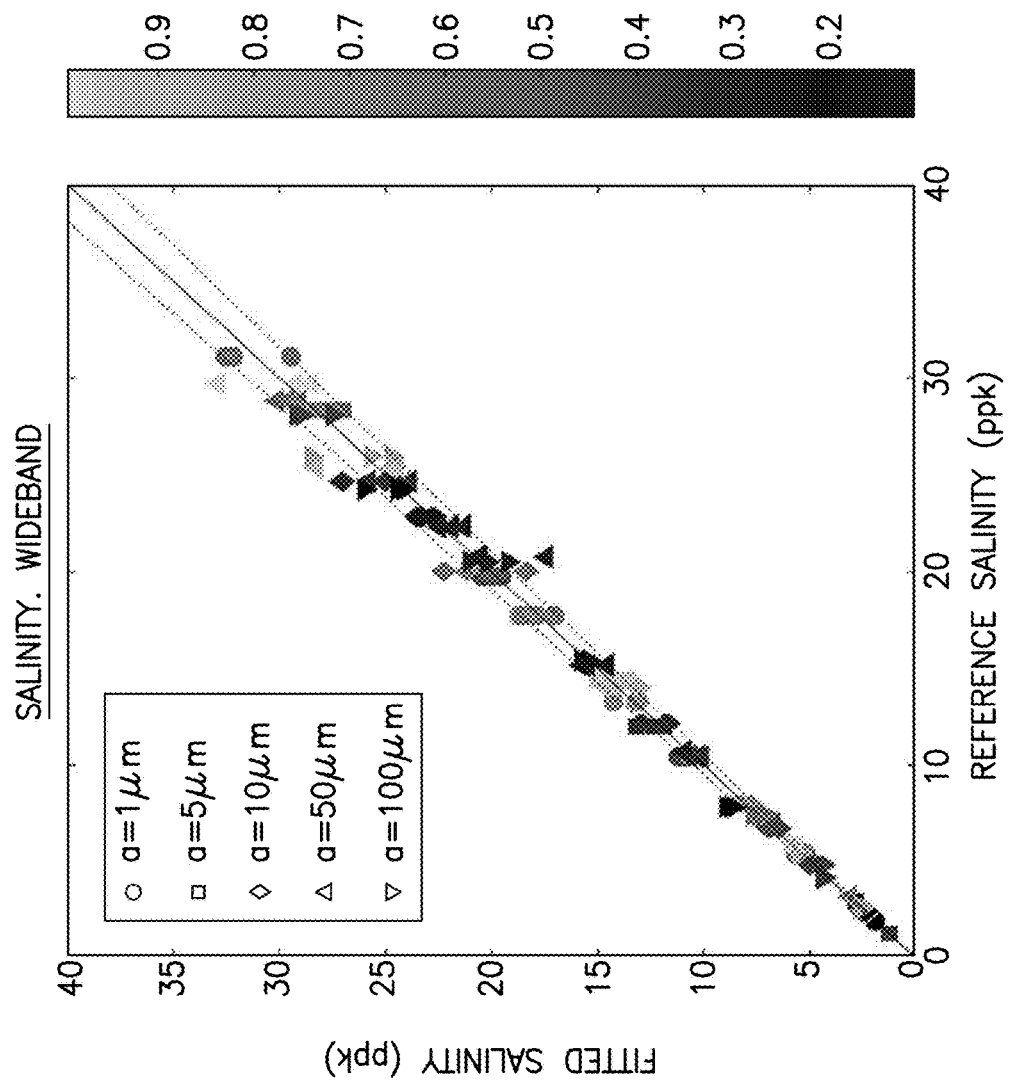
Figure 12C:
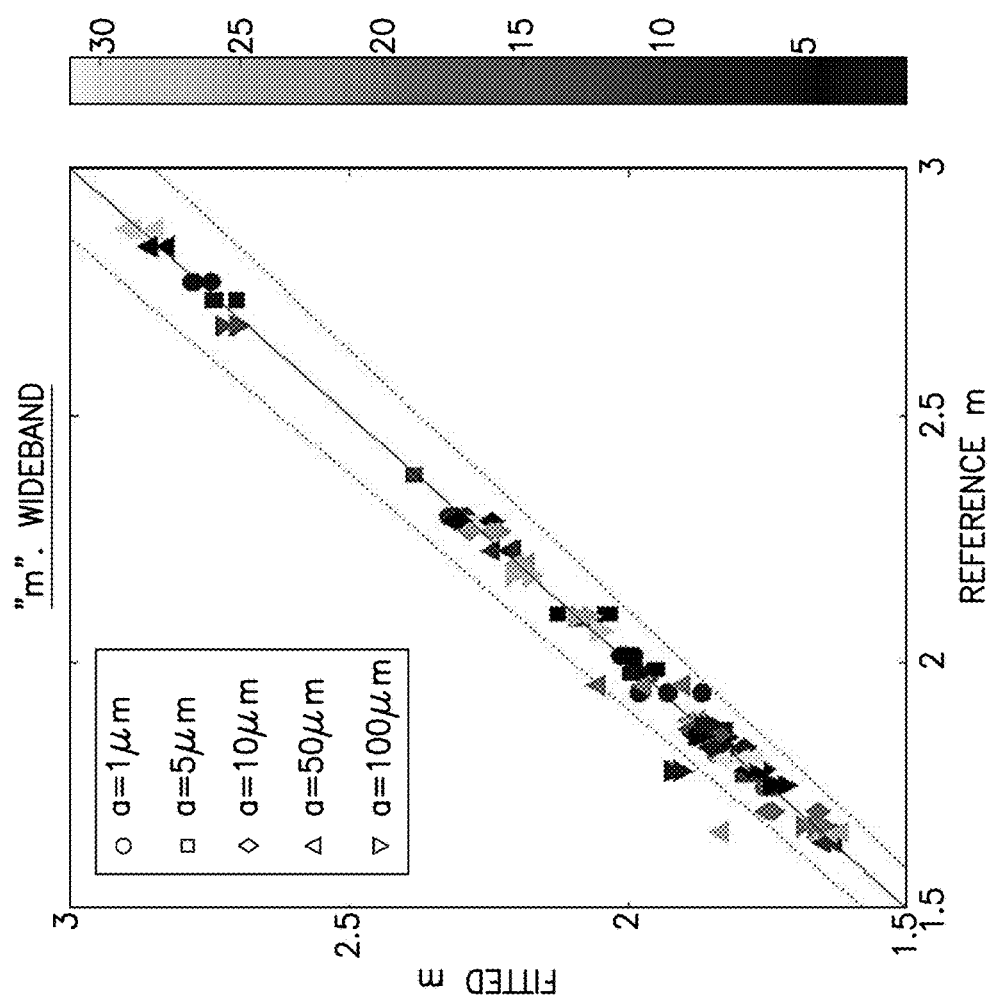
Figure 12D:
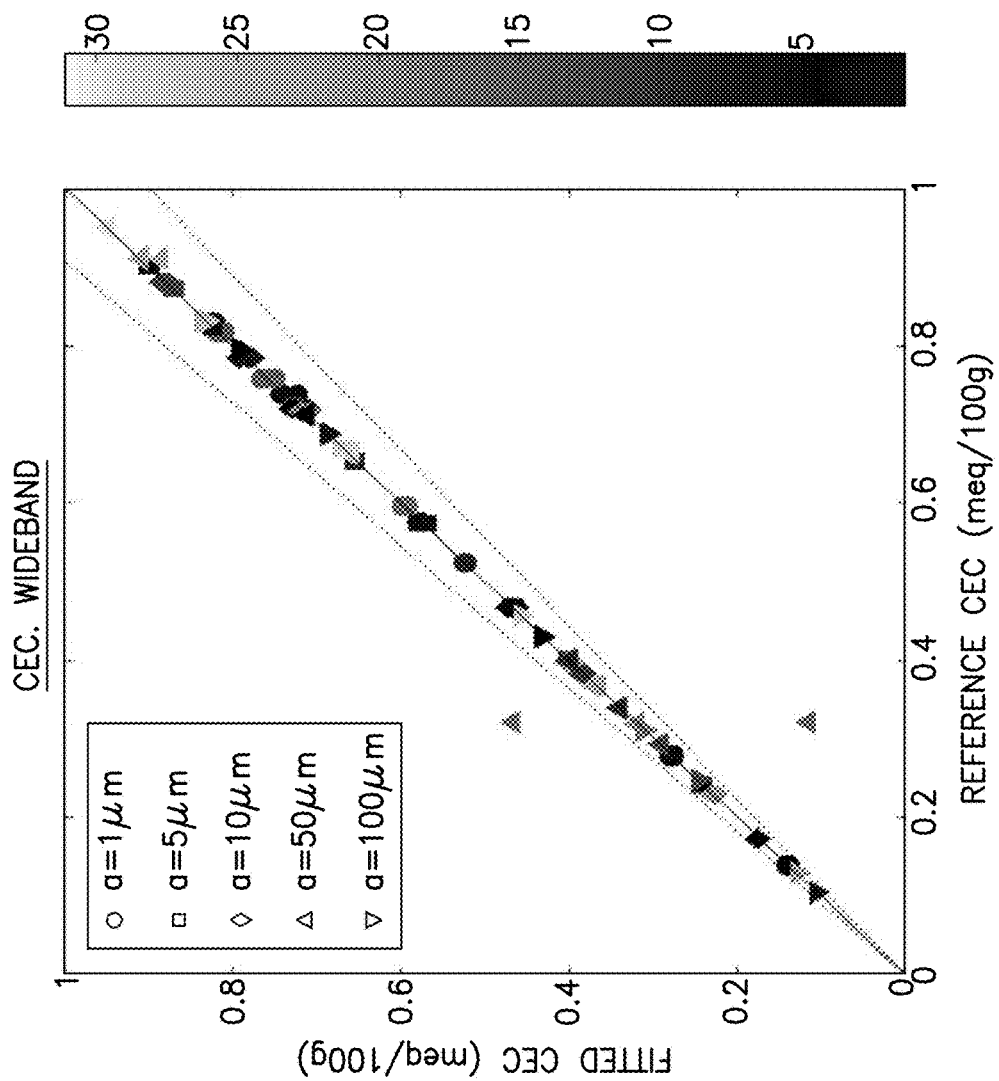
Figure 12E:
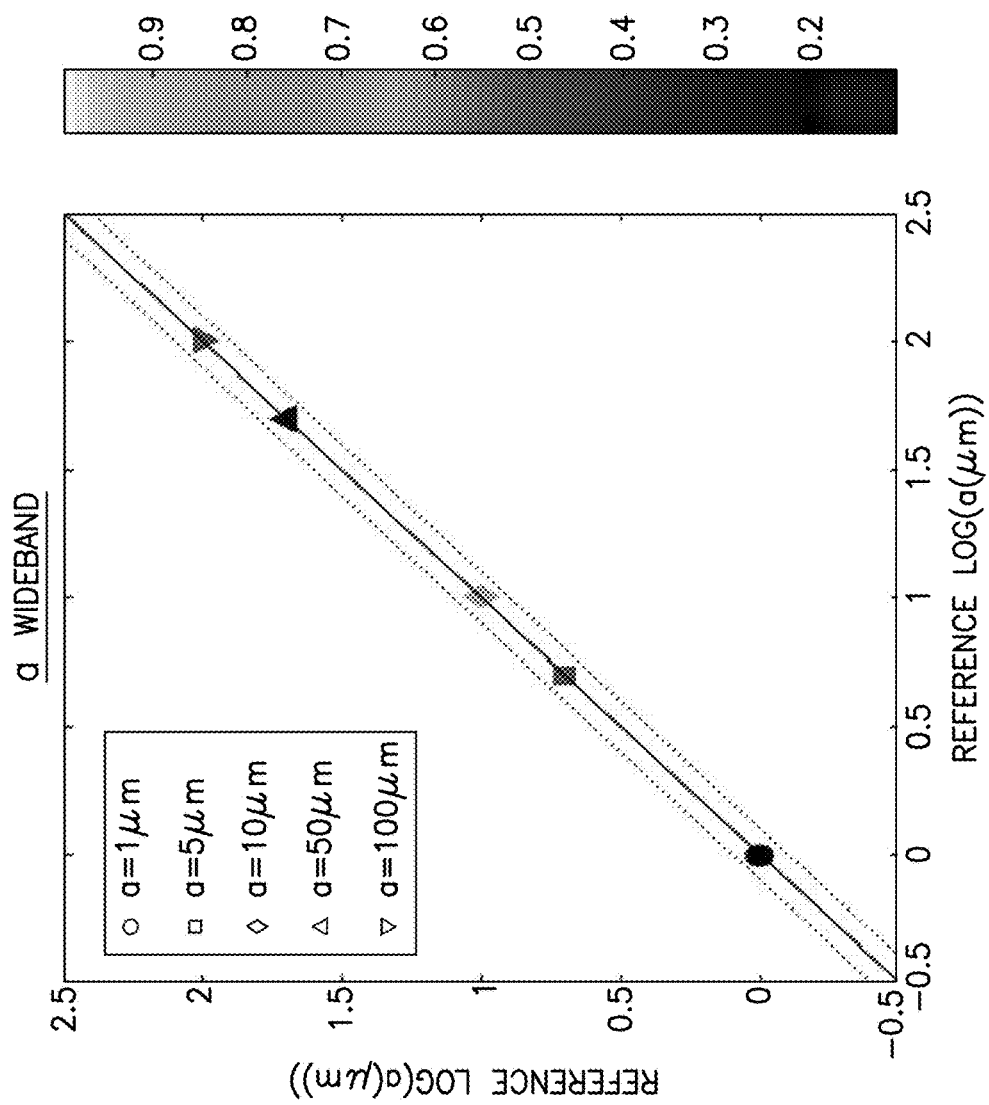
Figure 13A:
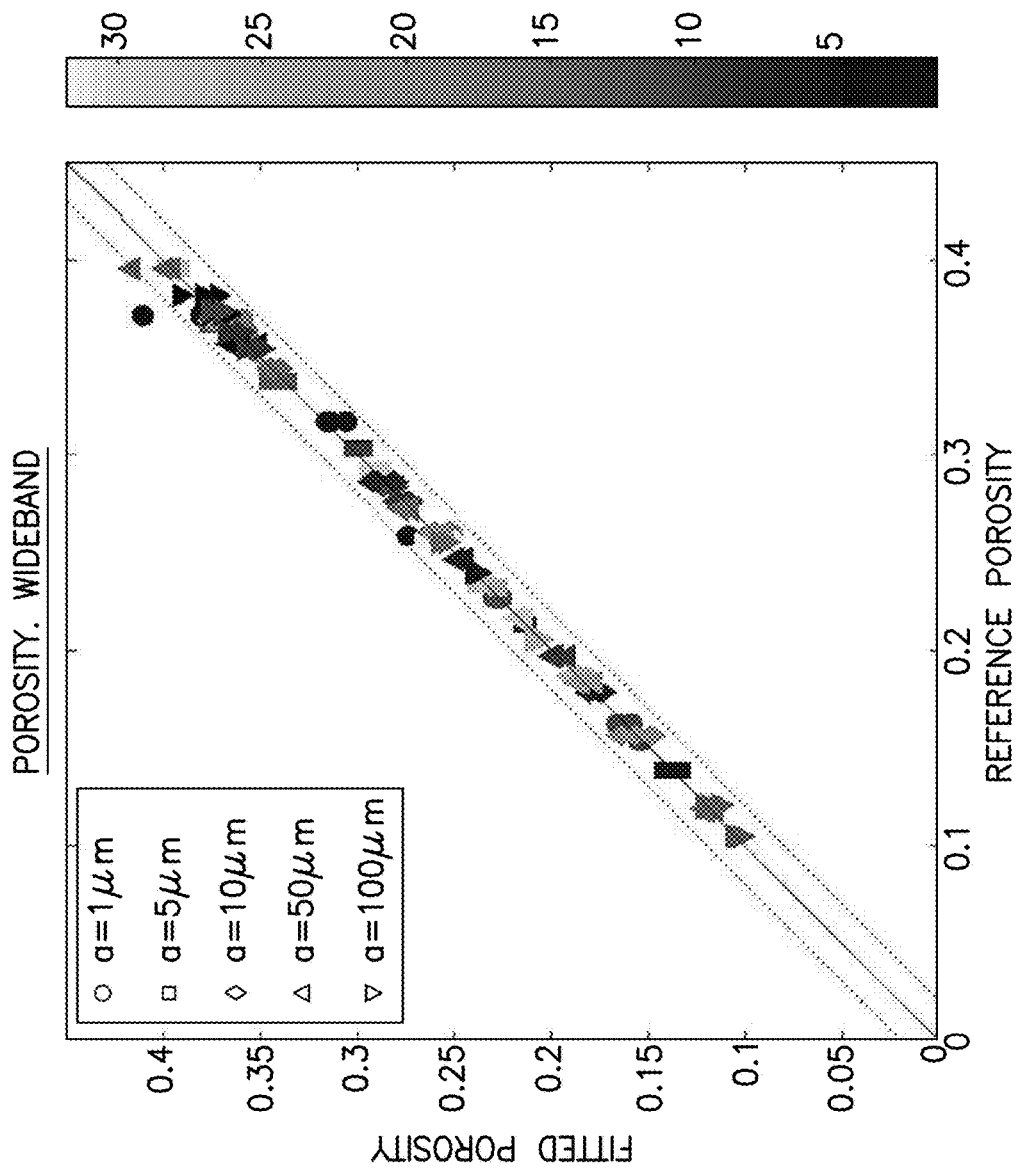
FIGS. 13a-13e are plots showing five parameters inverted from wideband data with a higher noise level than for FIGS. 12a-12e; the five parameters include water-filled porosity $\phi_w$ (FIG. 13a), water salinity $Sal_w$ (FIG. 13b), cementation exponent m (FIG. 13c), CEC (FIG. 13d), and charged grain size a (FIG. 13e); the plots show the inverted values for these five parameters versus the true or actual values for these five parameters for comparison purposes.
Figure 13B:
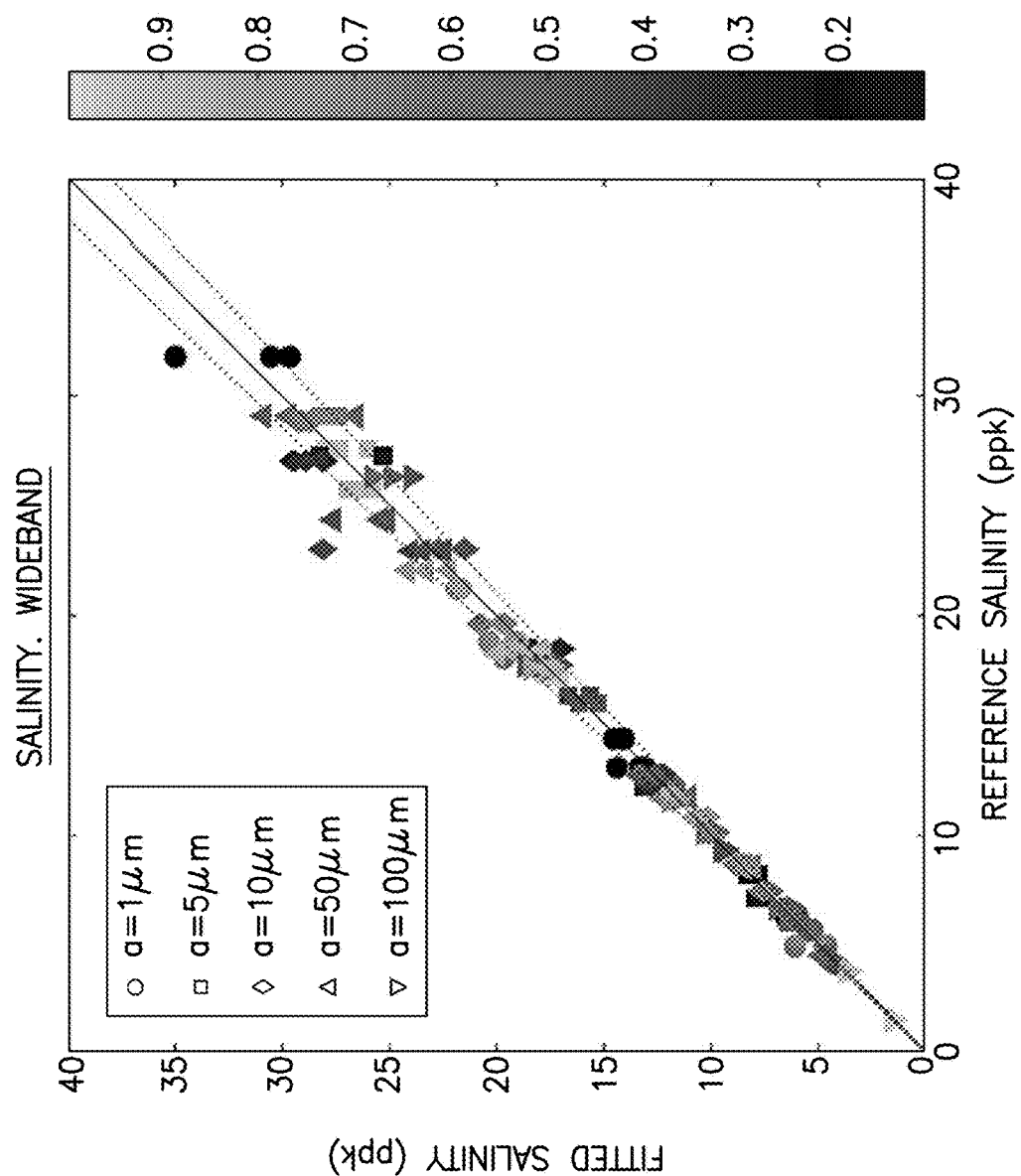
Figure 13C:
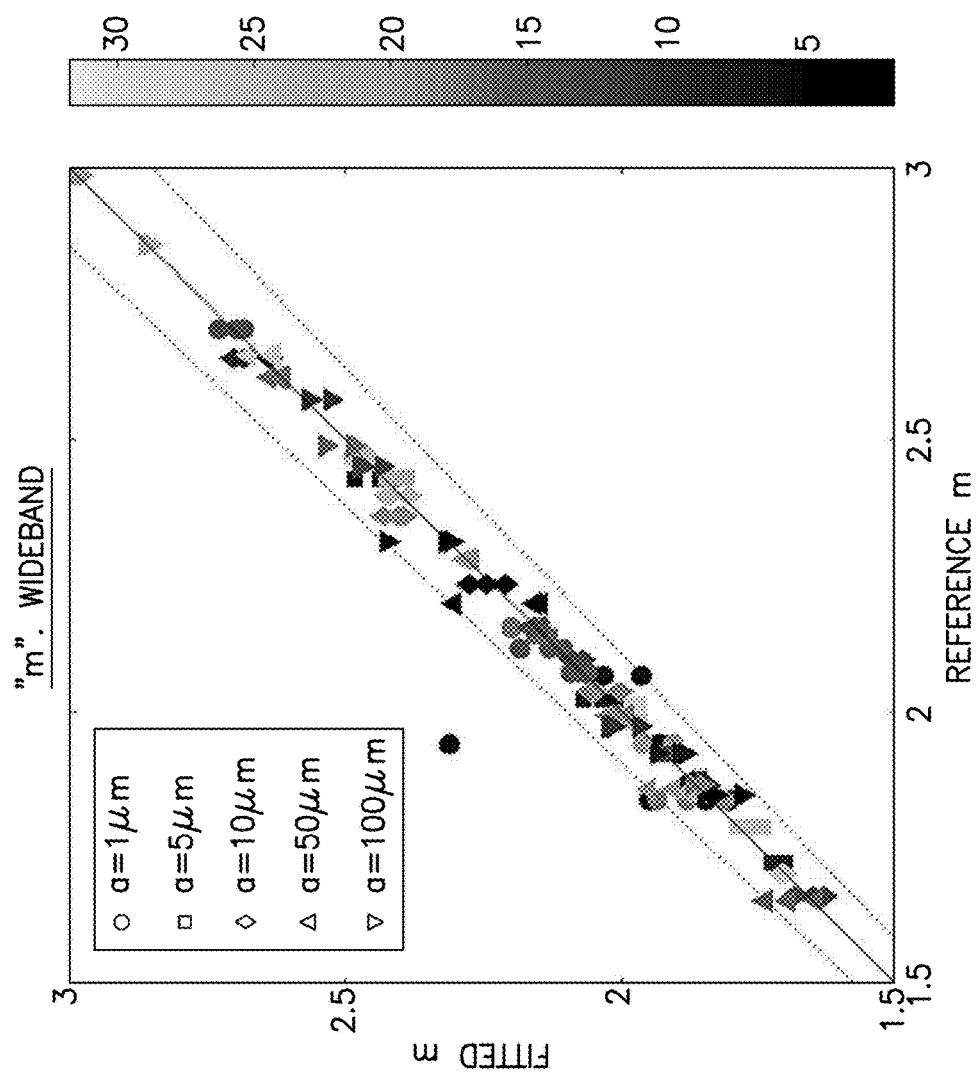
Figure 13D:
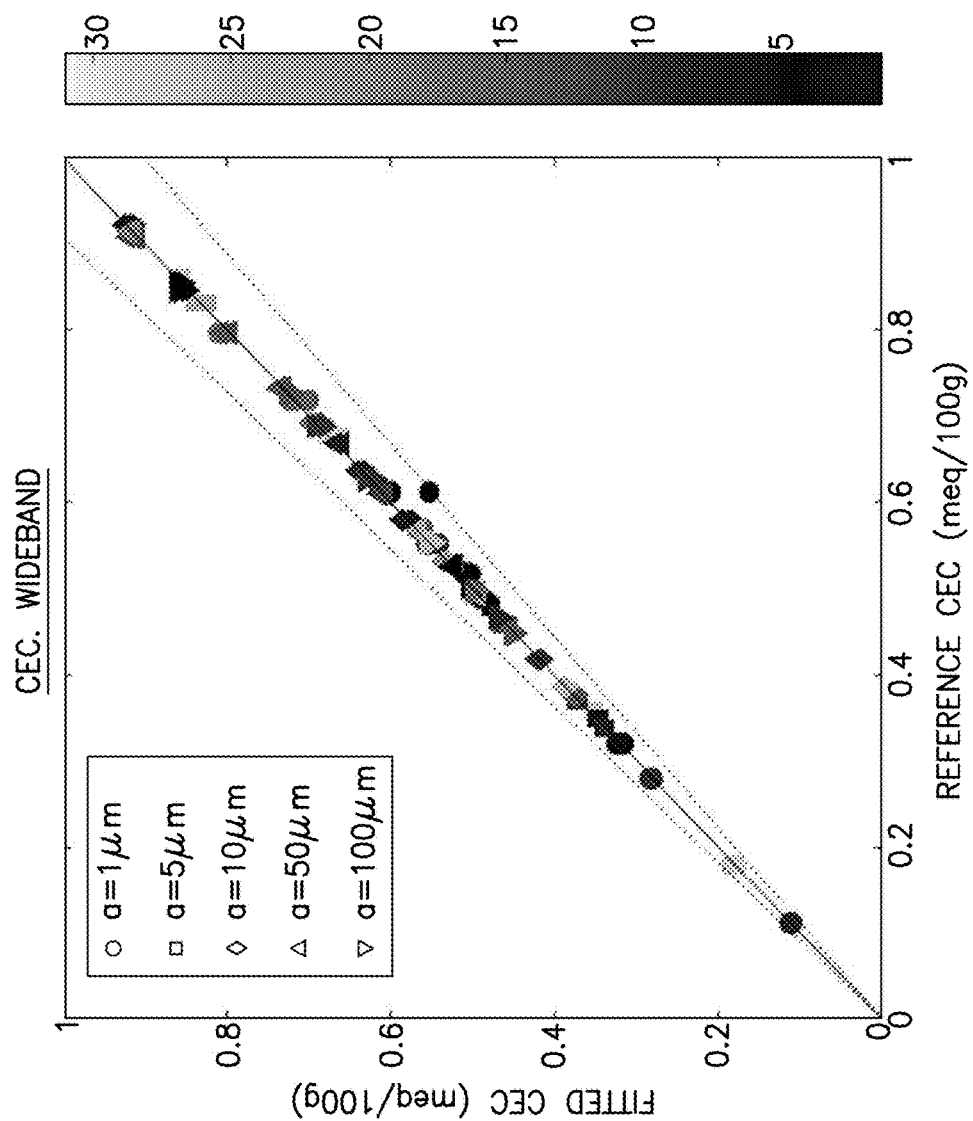
Figure 13E:
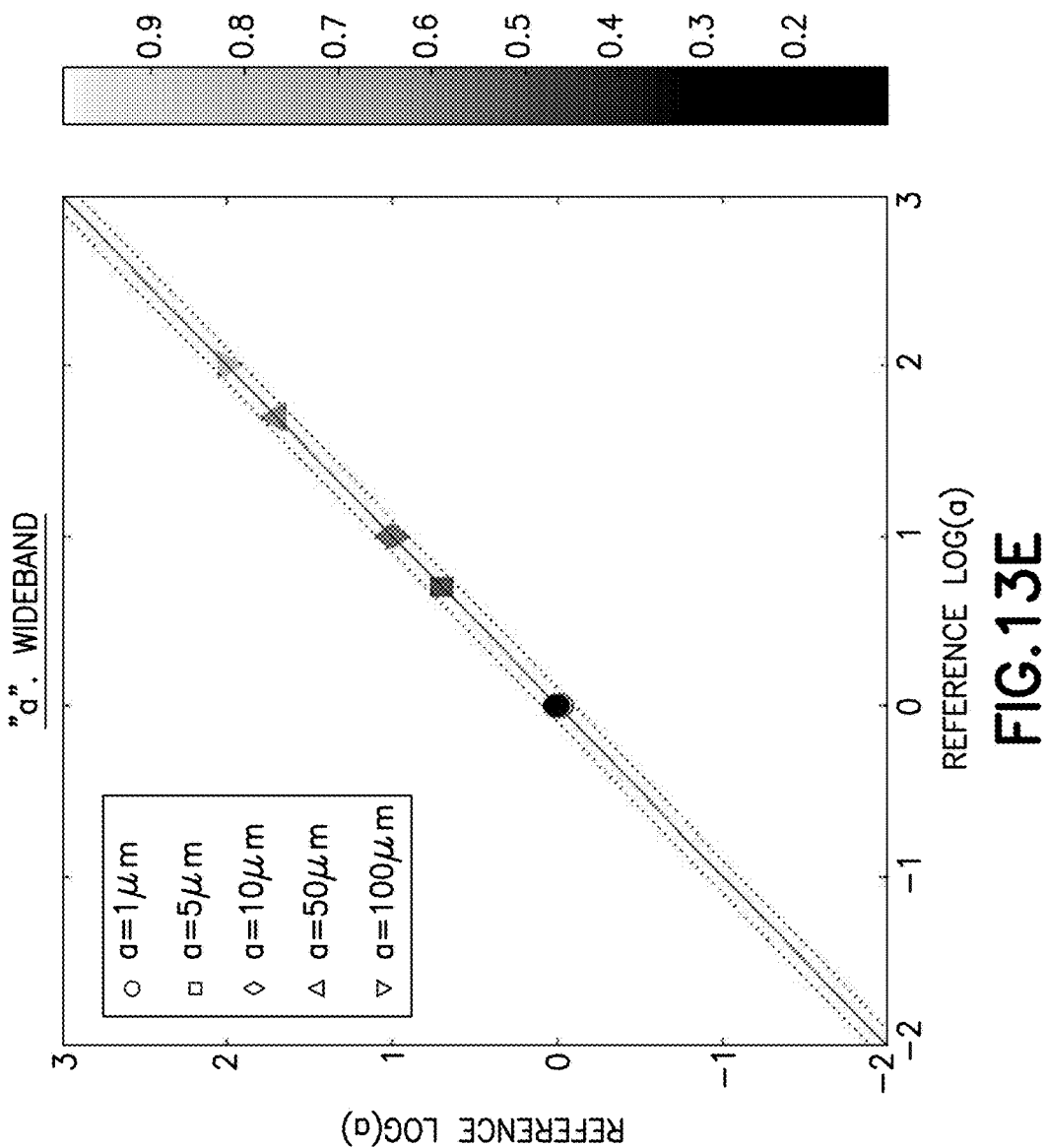

Inversion results for the higher noise level low-frequency dataset are shown in FIGS. 10a-10c. Again, the inversion was capable of reconstructing three unknowns with good accuracy, but with slightly higher scatter of the results as compared to FIGS. 9a-9c.

The results of inversion of the low-frequency data for five model parameters (CEC, cementation exponent (m), water-filled porosity ($\phi_w$), grain size (a) and water salinity (Sal$_w$)) with the fraction of spheroids (p) is shown in FIGS. 11a-11e. The inversion is using the same set of data with noise with 1% noise in conductivity and 1.5% in phase. The inversion results show that it is not possible to reliably reconstruct all five parameters just from the low-frequency data as it is hard for the inversion algorithm to find a global minimum and some of the inverted results are not reflecting the global minimum results. Even when the inversion is able to find the global minimum, the results often differ from the reference points.

On the other hand, as set forth below, the wideband inversion simultaneously including both the high- and the low-frequency data is capable of recovering all petrophysical parameters of the model not requiring any of them as input. In particular wideband datasets were investigated. Both datasets had the same noise level for high-frequency data. However, one dataset had a lower noise level for low-frequency data and the other dataset contain low-frequency data with a higher noise level.

Results of the wideband inversion using the lower noise level LF dataset are shown in FIGS. 12a-12e. Here inverted parameters include water-filled porosity ($\phi_w$), cation exchange capacity (CEC), grain size (a), water salinity (Sal$_w$), the parameter related to the aspect ratio of spheroids (d$_L$), and the volume fraction of spheroidal inclusions (p). It is evident that all parameters are correctly inverted for with the wideband approach. In addition, the accuracy of the inverted results for some parameters, such as the cementation exponent, is improved compared to the stand-alone high frequency data only inversion as may be seen by comparing FIG. 12c with FIG. 8c.

Results of the wideband inversion using the higher level of noise LF dataset are shown in FIGS. 13a-13e. Here, model petrophysical parameters are recovered with higher scatter (relative to FIGS. 12a-12e) which is as expected due to the higher noise level in the low-frequency data.

It will be appreciated that the above demonstrates that the wideband approach: (1) allows for an inversion for an extended set of petrophysical parameters, (2) eliminates uncertainty associated with having to input these parameters in the stand-alone data inversion for the high- or low-frequency range, and (3) improves inversion results for some of the parameters. The wideband approach makes it possible to invert for an extended set of petrophysical parameters that cannot all be inverted for at only low or only high frequencies.

In one aspect, the wideband interpretation approach is particularly useful at a shallow depth of investigation where the depth of investigation of an induced polarization logging tool can coincide with the depth of investigation of a high-frequency dielectric logging tool. The extension of the interpretation framework to a deep depth of investigation reading undisturbed formation is discussed herein after the following discussion of inversion of experimental data.

The wideband inversion approach was conducted on experimental data. High-frequency data and low-frequency data were obtained on a sandstone utilizing co-axial transmission line measurements (for example, as described in Seleznev, N., Shah, J., Vissaprahgada, B. and Volkmann, J., "Dielectric Measurements On Artificial Compacted Clay-Quartz Mixtures," presented at International Symposium of the Society of Core Analysts, Aberdeen, Scotland, UK, Aug. 27-30, 2012) and a four-terminal measurement (for example, as described in Titov, K., Tarasov, A., Ilyin, Y., Seleznev, N. and Boyd, A., "Relationships between induced polarization relaxation time and hydraulic properties of sandstone," Geophysical Journal International, Vol. 180(3), 2010, pp. 1095-1106). The petrophysical parameters of two samples of the sandstone rock are set forth in Table 2, as is the predominant grain size (major diameter of the best fitted ellipse) which was derived from thin section images.

TABLE 2

| | Water-filled Porosity ($\phi_w$), V/V | Water salinity (Sal$_w$), ppk | Grain size (a), μm | Cementation Exponent (m) |
|---|---|---|---|---|
| Sample 1 | 0.233 | 5 | 282 | 1.85 |
| Sample 2 | 0.239 | 0.2 | 282 | 1.85 |

Figure 14A:
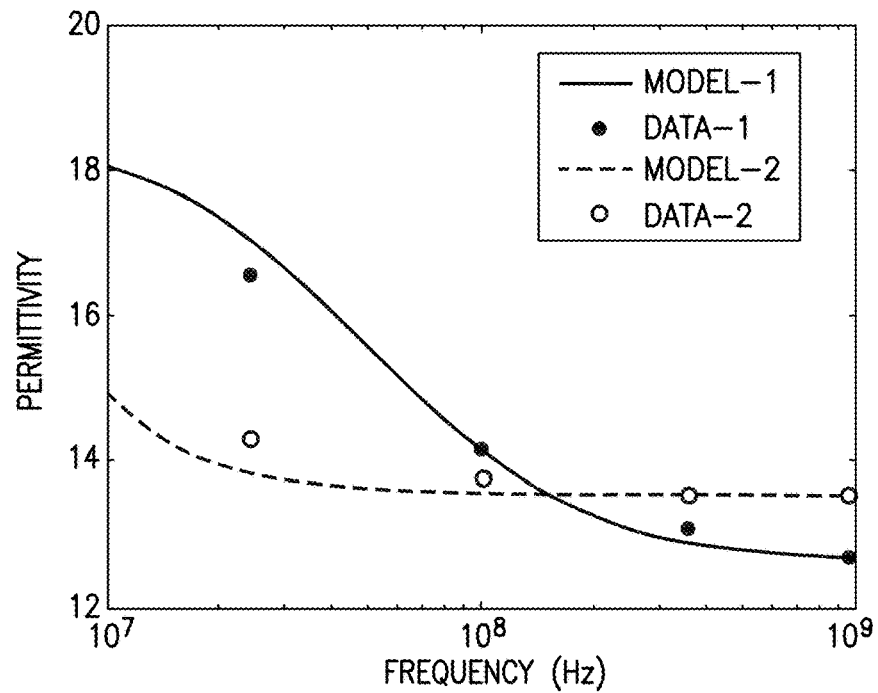
FIGS. 14a and 14b are plots showing the fit of the wideband model to the measured high frequency permittivity data (FIG. 14a) and to measured high frequency conductivity data (FIG. 14b) for two different rock samples; the high frequency permittivity data produced by the wideband model for the first rock sample is labeled "Model-1" in FIG. 14a and the measured high frequency permittivity data for the first rock sample is labeled "data-1" in FIG. 14a; the high frequency permittivity data produced by the wideband model for the second rock sample is labeled "Model-2" in FIG. 14a and the measured high frequency permittivity data for the second rock sample is labeled "data-2" in FIG. 14a; the high frequency conductivity data produced by the wideband model for the first rock sample is labeled "Model-1" in FIG. 14b and the measured high frequency conductivity data for the first rock sample is labeled "data-1" in FIG. 14b; the high frequency conductivity data produced by the wideband model for the second rock sample is labeled "Model-2" in FIG. 14b and the measured high frequency conductivity data for the second rock sample is labeled "data-2" in FIG. 14b.
Figure 14B:
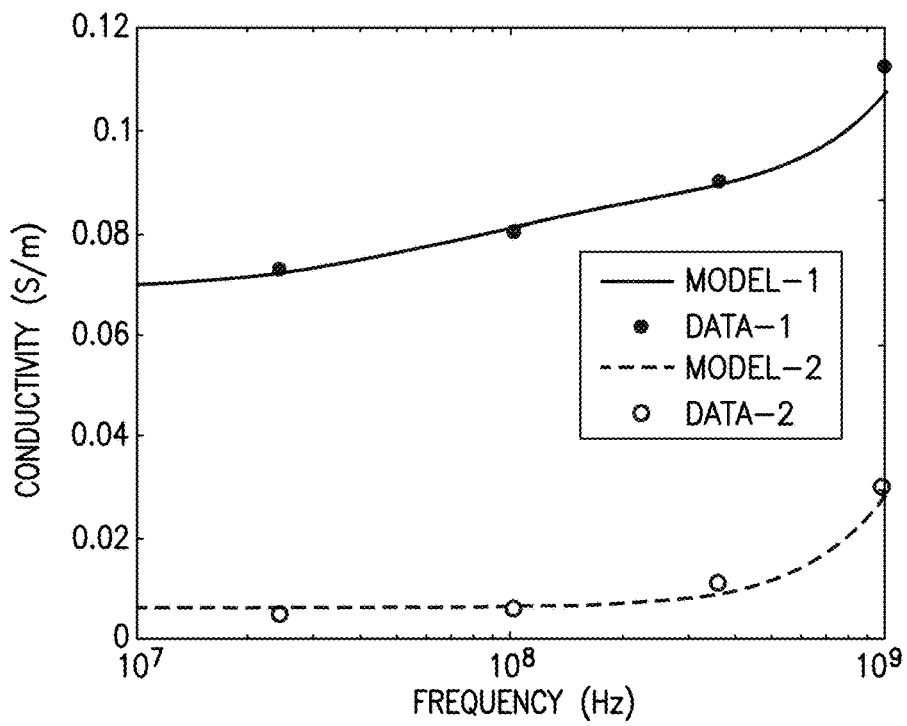
Figure 15A:
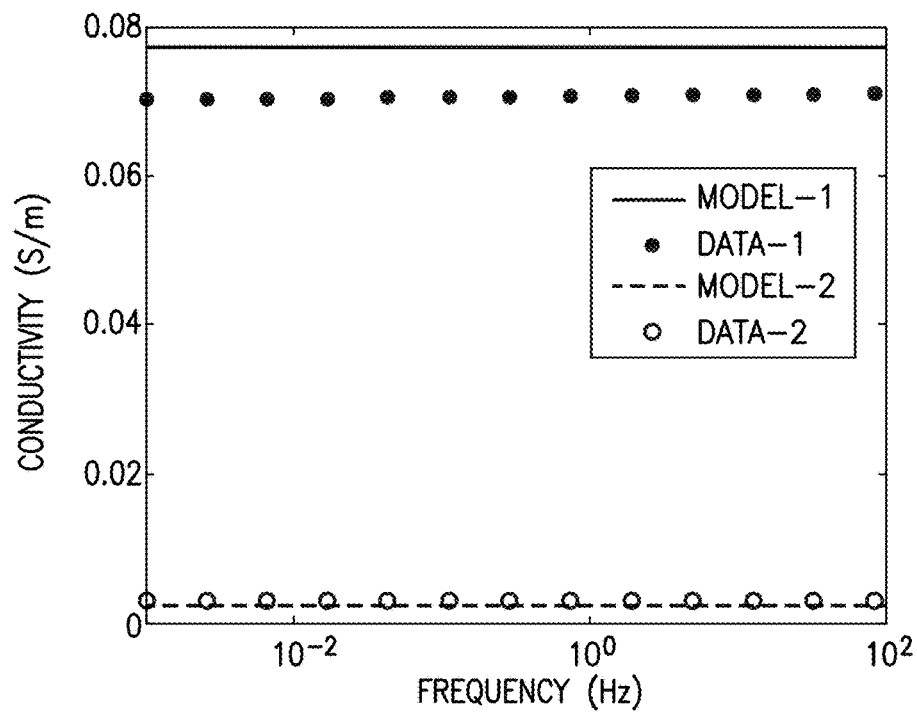
FIGS. 15a and 15b are plots showing the fit of the wideband model to the measured low frequency conductivity data (FIG. 15a) and to low frequency phase data (FIG. 15b); the low frequency conductivity data produced by the wideband model for the first rock sample is labeled "Model-1" in FIG. 15a and the measured low frequency conductivity data for the first rock sample is labeled "data-1" in FIG. 15a; the low frequency conductivity data produced by the wideband model for the second rock sample is labeled "Model-2" in FIG. 15a and the measured low frequency conductivity data for the second rock sample is labeled "data-2" in FIG. 15a; the low frequency phase data produced by the wideband model for the first rock sample is labeled "Model-1" in FIG. 15b and the measured low frequency phase data for the first rock sample is labeled "data-1" in FIG. 15b; the low frequency phase data produced by the wideband model for the second rock sample is labeled "Model-2" in FIG. 15b and the measured low frequency phase data for the second rock sample is labeled "data-2" in FIG. 15b.
Figure 15B:
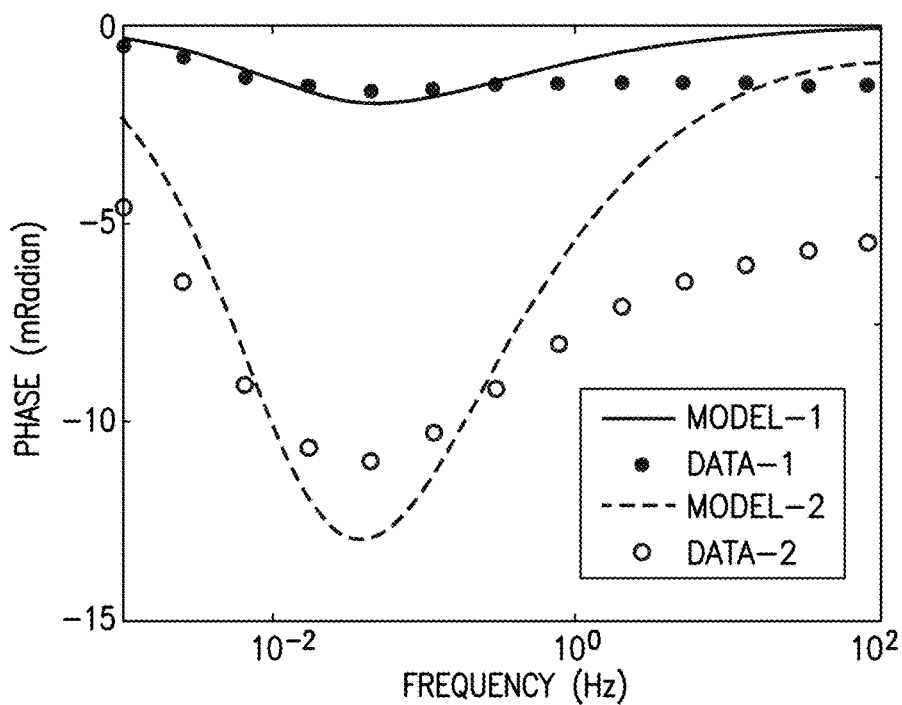

Experimental data was obtained in both high- and low-frequency ranges (e.g., wideband frequency range). The experimental data in both regions were simultaneously inverted utilizing the wideband model. The fits of the model predictions of the permittivity and conductivity to the experimental data are shown in FIGS. 14a and 14b for the high-frequency range and the fit of the model predictions of the conductivity and phase for the low frequency range are shown in FIGS. 15a and 15b. In both the high-frequency and low-frequency ranges, a reasonable fit is obtained between the data and model prediction. Modelled phase response correctly captures the phase peak that is related to the dominant grain size. The modelled width of the phase peak is smaller compared to the observed response due to rock samples having a distribution of grain sizes rather than a single grain size assumed in the model. In the model, the diffusion coefficient of sodium in bulk water was set equal to $D_{Na+}=1.33\times10^9$ m$^2$ s$^1$ at 25° C., and a value for $f_{stern}=0.8$ was utilized.

Petrophysical parameters determined from full wideband inversion are shown in Table 3.

TABLE 3

| | Water-filled Porosity ($\phi_w$), V/V | Water Salinity (Sal$_w$), ppk | Grain size (a), μm | CEC (quartz), meq/100 gr | Cementation Exponent (m) |
|---|---|---|---|---|---|
| Sample 1 | 0.230 | 5.38 | 291 | 0.4 | 1.86 |
| Sample 2 | 0.236 | 0.30 | 350 | 0.05 | 2.57 |

Inverted water-filled porosity ($\phi_w$) and water salinity (Sal$_w$) compare well with the measured values given in Table 2. The inverted grain size (a) is very close to the value derived from the thin section, especially given that the diffusion coefficient of sodium in bulk water is directly used without fine tuning. The inverted CEC values for quartz grains are in reasonable ranges. The cementation exponent (m) for the sample saturated with low salinity brine is overestimated due to low sensitivity to the cementation exponent (m) at low water salinities. The cementation exponent (m) for the sample saturated with higher salinity brine compares well with the intrinsic value.

Figure 16A:
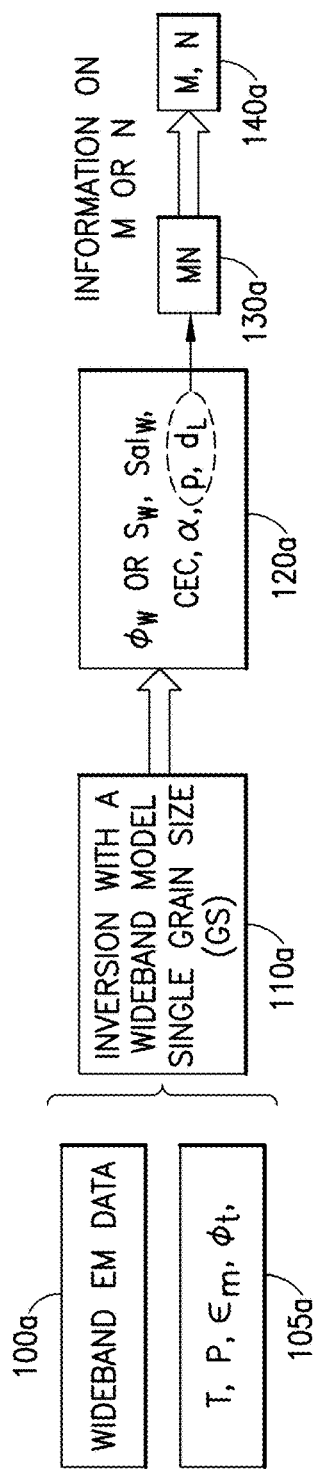
FIGS. 16a and 16b are flow charts showing inversion of wideband EM data utilizing a wideband model for determining formation parameters.

The flow chart for the inversion conducted in order to obtain the values in Table 3 is shown in FIG. 16a. In particular, at 100a, at least one logging tool (or a plurality of logging tools) can be run in a borehole to investigate the formation and obtain wideband EM response data. The wideband EM response data is gathered for processing. At 105a, other parameter values for the formation such as temperature, pressure, total porosity and matrix permittivity (typically obtained from other tools) are gathered. At 110a, the wideband EM response data and other parameter values can be stored and loaded from computer memory (which can be volatile or non-volatile memory) and supplied to a processor which conducts a multi-parameter inversion based on the wideband model having a single grain size a (such as equation (8)) in order to minimize a cost function such as equation (18). The results of the inversion are output at 120a and include the water saturation or water-filled porosity ($\phi_w$), the water salinity (Sal$_w$), CEC, grain size (a), parameter p, and parameter $d_L$. Parameters p and $d_L$ may then be used at 130a to obtain the apparent cementation factor m$_n$, which in turn may be used to obtain the cementation exponent m and the water saturation exponent n (of the Archie's equation) at 140a.

In another embodiment, the wideband model utilizes two or more grain sizes instead of a predominant grain size. A distribution of grain sizes can be defined directly via several bins spanning the range of grain sizes encountered in oilfield formations. Alternatively, the grain size distribution can be represented by a continuous probability density function defined by several parameters. Among different possible distributions, a Gaussian distribution can be used and is defined by:

$$f(x \mid v, \beta^2) = \frac{1}{\sqrt{2\beta^2\pi}} e^{-\frac{(x-v)^2}{2\beta^2}}. \quad (21)$$

where v is the mean of the distribution and β is a standard deviation. If grain size distribution is assumed to be Gaussian, the mean and standard deviation of Gaussian distribution will be inverted for with the wideband EM response data instead of the predominant grain size as is the case for a single grain size model. A flow chart for this embodiment is shown in FIG. 16b.

Figure 16B:
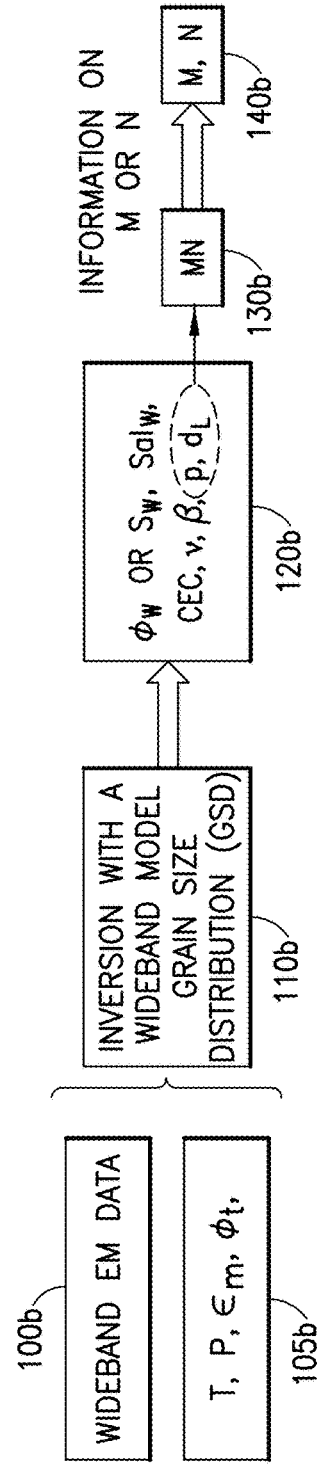

More particularly, as seen in FIG. 16b, at 100b, at least one logging tool (or a plurality of logging tools) can be run in a borehole to investigate the formation and obtain wideband EM response data. The wideband EM response data is gathered for processing. At 105b, other parameter values of the formation such as temperature, pressure, total porosity and matrix permittivity (typically obtained from other tools) are gathered. At 110b, the wideband EM response data and other parameter values can be stored and loaded from computer memory (which can be volatile or non-volatile memory) and supplied to a processor which conducts a multi-parameter inversion based on the wideband model having a grain size distribution (such as equation (12) or another equation that accounts for other specifically identified grain sizes or grain sizes distributed according to a Gaussian or other distribution) in order to minimize a cost function such as equation (18). The results of the inversion are output at 120b and include the water saturation or water-filled porosity ($\phi_w$), the water salinity (Sal$_w$), CEC, grain size (a), parameter p, and parameter $d_L$. Parameters p and $d_L$ may then be used at 130b to obtain the apparent cementation factor m$_n$, which in turn may be used to obtain the cementation exponent m and the water saturation exponent n (of the Archie's equation) at 140b.

According to another embodiment, the inversion of the wideband data is done with two different models: one describing the response of the formation to EM measurements in the high frequency range (referred to herein as a "high frequency model") and another one describing the response of the formation to EM measurements in the low frequency range (referred to herein as a "low frequency model"). In the high frequency range, the dielectric response does not depend on the particle size, so the high frequency model does not need to include the grain size as a parameter. In addition, the amount of charge on quartz is very small and does not affect the dielectric response in the high frequency range. Instead, the high frequency model can focus more directly on properties that are relevant to the high frequency range, such as the water-filled porosity, water salinity, or the shape of platy clay grains. One example of a suitable high frequency model is the CRIM model, which is commonly used to determine the water-filled porosity and water salinity from the EM response data in the high frequency range. This model can be used to determine $\in_{model,j}$ and $\sigma_{model,j}$ for the high frequency range in the cost function, while the wideband model given above can be used as the low frequency model to calculate water-filled porosity and water salinity and $\theta_{model,j}$ for the low frequency range in the cost function. When there is also a significant amount of clay grains in the rock, the model described in Freed, D. et al., "A Physics-Based Model for the Dielectric Response of Shaly Sands," Trans. Of SPWLA Annual Logging Symposium, Jun. 25-29, 2016, which is hereby incorporated by reference herein in its entirety, can be used as the high frequency model. In this model charged spheroids are used to capture the effect of platy clay grains and non-charged spheres are used to represent the effect of quartz grains. The equation for the complex rock permittivity is similar to the one for the wideband model given above, but the values of the $p_j$ and $r_j$ are different. This model depends on the aspect ratio of the platy grains, the charge on the platy grains, the water salinity, and the water-filled porosity, but not on the grain size. In this case, a similar model can be used for the low frequency model, where now the model includes both charged spherical particles for the quartz and charged spheroidal particles, with the appropriate low-frequency response, for the clay grains.

Alternatively, in the low frequency model, the charge can be placed on the spheroidal particles and the spherical particles will be non-charged. The model can account for Maxwell-Garnett interfacial polarization related to rock texture and electrochemical polarization effects with the textural and electrochemical polarization effects coming from the spheroidal charged particles mixed with non-charged spherical particles and dispersed in a host of brine. Different combinations of the aforementioned low and high frequency models or any other low and high frequency or wideband models can be used in the wideband inversion approach. In general, using two separate models for the low and high frequency ranges of the EM response data can capture the most dominating effects in different frequency ranges for a set of common and complementary petrophysical parameters.

A flow chart for the embodiment using different models for the high- and low-frequency ranges is shown in FIG. 16(c). In this case, at 100c, at least one logging tool (or a plurality of logging tools) can be run in a borehole to investigate the formation and obtain wideband EM response data. The at least one logging tool can be conveyed through the borehole by a conveyance mechanism. The conveyance mechanism can be a wireline cable (wireline tool), drill pipe (logging while drilling tool), a tractor device, a tool string that extends through a drill bit (thru-bit logging tool) or other suitable conveyance mechanism. The wideband EM response data is gathered for processing. At 105c, other parameter values of the formation such as temperature, pressure, total porosity, matrix permittivity, and clay volume ($V_{cl}$) (all typically obtained from other tools) are gathered. At 110c, the wideband EM response data and other parameter values can be stored and loaded from computer memory (which can be volatile or non-volatile memory) and supplied to a processor which conducts a multi-parameter simultaneous inversion by inverting for a set of common parameters in the high- and low-frequency models which are output at 120c. For example, these parameters can include water-filled porosity ($\phi_w$) water salinity ($Sal_w$), cementation exponent m (or the exponent MN in case of hydrocarbon-bearing formation), and cation exchange capacity. The MN exponent is defined via Archie's law according to $$\sigma_r = {}^m S_w {}^n \sigma_w = (S_w)^{MN} \sigma_w \qquad (22)$$

where $\sigma_r$ is the rock conductivity, $\phi$ is the rock total porosity, $S_w$ is the water saturation, and $\sigma_w$ is the water conductivity. At 125c, the predominant formation grain size is determined from the low-frequency model.

In another embodiment shown in FIG. 16d, different models for the high- and low-frequency ranges as in FIG. 16c are utilized, but the low-frequency model includes grain size distribution. In this case, at 100d, at least one logging tool (or a plurality of logging tools) can be run in a borehole to investigate the formation and obtain wideband EM response data. The at least one logging tool can be conveyed through the borehole by a conveyance mechanism. The conveyance mechanism can be a wireline cable (wireline tool), drill pipe (logging while drilling tool), a tractor device, a tool string that extends through a drill bit (thru-bit logging tool) or other suitable conveyance mechanism. The wideband EM response data is gathered for processing. At 105d, other parameter values of the formation such as temperature, pressure, total porosity, matrix permittivity, and $V_{cl}$ (all typically obtained from other tools) are gathered. At 110d, the wideband EM response data and other parameter values can be stored and loaded from computer memory (which can be volatile or non-volatile memory) and supplied to a processor which conducts a multi-parameter simultaneous inversion by inverting for a set of common parameters in the high- and low-frequency models which are output at 120d. For example, these parameters can include water-filled porosity ($\phi_w$), water salinity ($Sal_w$), cementation exponent m (or the exponent MN in case of hydrocarbon-bearing formation), and cation exchange capacity. In addition, at 125d, the low-frequency model inversion produces several parameters related to grain size distribution. For example, in case of Gaussian distribution these parameters are the mean of the distribution ν and the standard deviation β.

As previously mentioned, the wideband inversion approach is particularly useful at a shallow depth of investigation where the depth of investigation of an induced polarization logging tool can coincide with the depth of investigation of a high-frequency dielectric logging tool. However, according to one aspect, the interpretation framework may be extended to a deep depth of investigation. More particularly, Table 4 compares capabilities of the high-frequency dielectric dispersion and the low-frequency induced polarization EM logging measurements.

TABLE 4

| Type of Application | Dielectric Dispersion | Induced Polarization |
|---|---|---|
| Shallow Measurements | Yes | Yes |
| Deep Measurements | No | Yes |
| WBM Logging | Yes | Yes |
| OBM Logging | Challenging | Yes |

As the penetration is not limited by the skin depth at low frequency, it is possible to extend low-frequency measurements away from the borehole. This is a significant advantage as it allows probing the virgin formation zone. At the same time the low-frequency EM measurement can also be conducted at the same radial depth of investigation (DOI) as the dielectric measurements to facilitate joint interpretation of these sensors.

Figure 17:
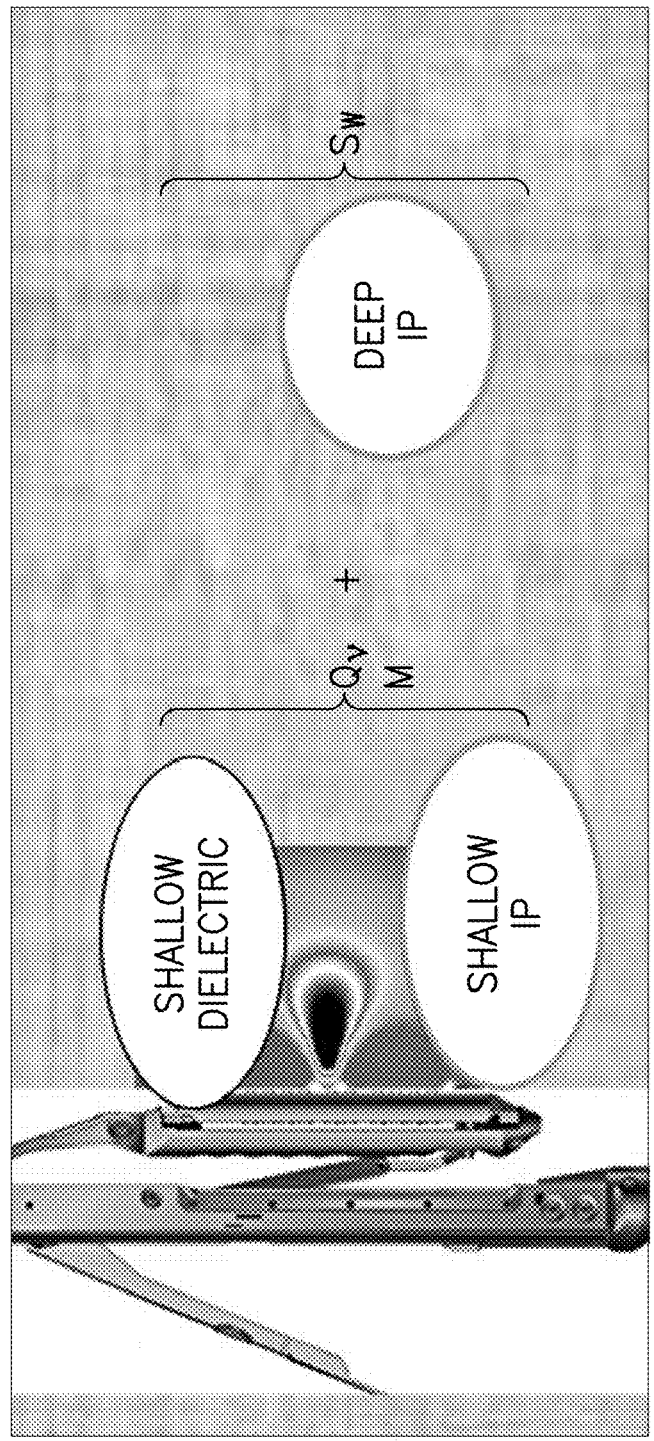
FIG. 17 is a diagram showing the workflow for interpreting induced polarization data and borehole dielectric data at multiple radial depths of investigation.

In one aspect, and as suggested by FIG. 17, an interpretation of a wideband formation EM response data may be carried out at a shallow DOI where both the dielectric and induced polarization logging data can be obtained from consonant formation volumes. This interpretation yields full and robust set of petrophysical parameters as the wideband EM formation response data can be analyzed. Some of these petrophysical quantities, for example, cementation exponent m and Qv (or CEC) will not change away from the borehole if the formation layers do not have significant dip. Thus, these parameters may be used as inputs for interpreting the induced polarization logging data measured at the deep radial DOI in the uninvaded zone. The cementation exponent, m, and/or Qv (or CEC) derived from the wideband response in the shallow zone will enable more accurate determination of the water saturation in the uninvaded zone from the induced polarization data.

Figure 18:
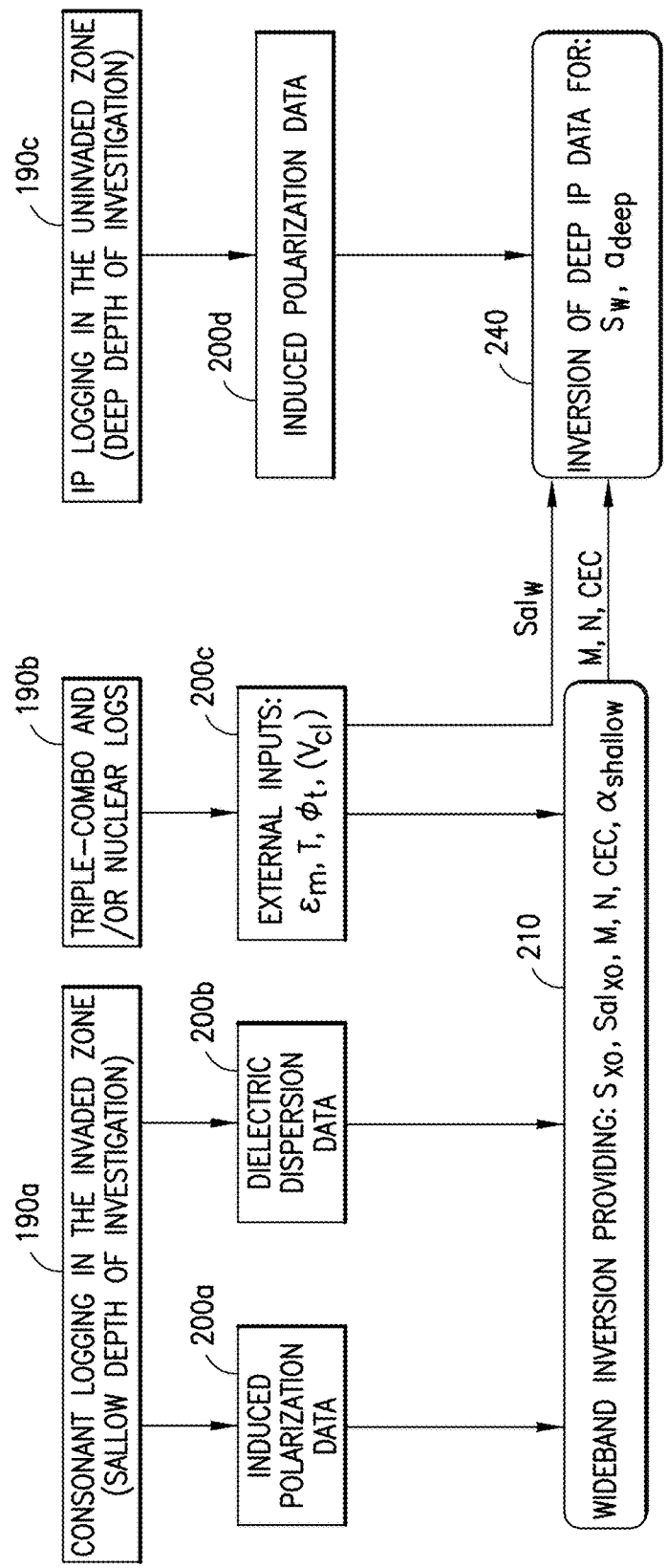
FIG. 18 is a flow chart showing multi-radial depth joint inversion of induced polarization and dielectric data.

One embodiment of using parameter determinations for the shallow DOI from the wideband analysis for a determination of parameters for the deeper zone of investigation is seen in the flow chart of FIG. 18. As seen in FIG. 18, at 190a at least one EM logging tool (or a plurality of EM Logging tools) is(are) run in a borehole to investigate the formation near the borehole (shallow depth of investigation). Induced polarization data is obtained at 200a and dielectric dispersion data is obtained at 200b. The at least one EM logging tool can be conveyed through the borehole by a conveyance mechanism. The conveyance mechanism can be a wireline cable (wireline tool), drill pipe (logging while drilling tool), a tractor device, a tool string that extends through a drill bit (thru-bit logging tool) or other suitable conveyance mechanism. In addition, at 190b a tool such as the SCHLUMBERGER™"Triple Combo" (a tool including a natural gamma ray sonde, an accelerator porosity sonde, a lithodensity tool, a caliper, a dual induction tool, and a temperature/pressure/acceleration tool) and/or nuclear tools is run in the borehole. Such tool(s) can be conveyed through the borehole by a conveyance mechanism. The conveyance mechanism can be a wireline cable (wireline tool), drill pipe (logging while drilling tool), a tractor device, a tool string that extends through a drill bit (thru-bit logging tool) or other suitable conveyance mechanism. The information obtained by such tool(s) is used to obtain (at least) dielectric permittivity of matrix ($\varepsilon_m$), formation temperature (T), formation total porosity ($\phi_t$), and the volume of clay ($V_{cl}$) at 200c. At 210, the low- and high-frequency logging data can be stored and loaded from computer memory (which can be volatile or non-volatile memory) and supplied to a processor which performs a joint inversion of the low- and high-frequency logging data using one of the wideband inversion methods previously discussed herein. This joint inversion generates determinations of the formation water saturation in the invaded zone ($S_{xo}$), the water salinity in the invaded zone ($Sal_{xo}$), cation exchange capacity (CEC) in the shallow zone, a predominant grain size (a) in the shallow zone, and the exponent MN. From the exponent MN, the cementation exponent (m), and the saturation exponent (n) are computed using external information on m or n as is known in the art.

Having found various parameters regarding the shallow zone using the wideband inversion, a subset of those parameters from the shallow zone may be used for the interpretation of the low-frequency EM data in the deep zone. In particular, and in one embodiment, the subset comprises m, n, CEC and $a_{shallow}$. Thus, as shown in FIG. 18, the lower frequency EM tool used for logging at 190a may also be used at 190c for obtaining a deep depth of investigation into the borehole. The lower frequency EM tool can be conveyed through the borehole by a conveyance mechanism. The conveyance mechanism can be a wireline cable (wireline tool), drill pipe (logging while drilling tool), a tractor device, a tool string that extends through a drill bit (thru-bit logging tool) or other suitable conveyance mechanism. At 200d, induced polarization information relating to the deep zone is obtained. Then, using the deep zone induced polarization information, the subset of parameters (m, n, CEC) obtained from the joint inversion at 210, and, optionally, additional (external input) information such as deep zone water salinity $Sal_w$ obtained from the Triple Combo tool or other tools, or otherwise known information can be stored and loaded from computer memory (which can be volatile or non-volatile memory) and supplied to a processor which conducts an inversion at 240 to obtain determinations of formation parameters such as water saturation Sw and deep grain size $a_{deep}$ in the deeper zone.

External parameters used as inputs to the wideband interpretation in the shallow zone are also used as inputs in the deep zone interpretation. The low-frequency EM response data in the deep zone is inverted to produce undisturbed formation water saturation using all of the above external inputs and an assumption on the formation water salinity. In another embodiment the volume of clay, $V_{cl}$ can also be inverted for at the wideband inversion step.

In another embodiment the wideband inversion is used to solve for parameters describing grain size distribution of the formation (instead of a single predominant grain a). For example, parameters that define grain size distribution can be, but not limited to, the mean of the distribution, $\nu$, and standard deviation, $\beta$, such as in the Gaussian distribution. In this embodiment, interpretation of the EM response data in the deep zone uses the parameters defining grain size distribution as inputs instead of predominant grain size, a.

In another embodiment the formation water salinity in the deep zone, $Sal_w$, is provided as an external input and the deep low-frequency data is inverted for the uninvaded zone formation water saturation, $S_w$, and undisturbed formation predominant grain size, $a_{deep}$. Alternatively, the deep low-frequency data is inverted for the uninvaded zone formation water saturation, $S_w$, and undisturbed formation grain size distribution parameters, such as $\mu$ and $\alpha$ or any other set of parameters describing grain size distribution.

In one aspect, some of the methods and processes described above, such as (by way of example and not by way of limitation) multiparameter searches are performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Thus, by way of example only, and not by way of limitation, while various embodiments of a wideband EM model were presented, it will be appreciated that other wideband models could be utilized. Also, while various embodiments describe different cost functions and inversion techniques, it will be appreciated that other cost functions and/or inversion techniques may be utilized. Further, embodiments discussed or showed investigation of a formation through the use of logging tools, it will be appreciated that investigation of a rock sample (e.g., core) using the wideband models may be accomplished in a lab. Accordingly, all such modifications are intended to be included within the scope of this disclosure as defined in the following claims. In the claims, means-plus-function clauses are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of investigating a rock sample, comprising:
using electromagnetic equipment to perform electromagnetic measurements of the rock sample at frequencies that fall within a wideband of frequencies, wherein the wideband of frequencies includes a low frequency sub-band including at least one frequency less than 10 KHz that is sensitive to conductivity of the rock sample and a high frequency sub-band including at least one frequency greater than 10 MHz that is sensitive to the permittivity of the rock sample;
using a data processor to obtain wideband electromagnetic response data derived from the electromagnetic measurements of the rock sample and to perform an inversion of said wideband electromagnetic response data in order to determine values for a plurality of parameters of the rock sample, wherein the inversion employs a wideband model that accounts for two different polarization mechanisms, including i) polarization on interfaces between conductive fluid and non-conductive mineral grains and/or non-conductive hydrocarbons, and ii) polarization of an electrical double layer present on charged mineral grains.

2. The method of claim 1, wherein:
the wideband model is based on the complex dielectric constant of a charged grain $\varepsilon_m^*$ given as:

$$\varepsilon_m^* = \varepsilon_m + i\frac{\Gamma_0 \sigma_w}{N_0 a}\frac{1}{\omega\varepsilon_0},$$

where $\varepsilon_m$ is the real part of the dielectric constant of the grain matrix;
$\Gamma_0$ is a surface charge density;
$\sigma_w = 2D(Ze_0)^2 N_0/(k_B T)$ is intrinsic brine conductivity with ion concentration $N_0$, ion charge Z, diffusion coefficient D, an electron charge with an absolute value $e_0$, Boltzmann constant kB, and temperature in degrees Kelvin T;
a is grain radius; and
$\varepsilon_0$ is the vacuum permittivity.

3. The method of claim 1, wherein:
the wideband model is based on a mixing model for rock porosity $\phi$ for at least one grain size given as:

$$\phi = \prod_{j=0}^{n}\left(\frac{\varepsilon_w - p_j}{\varepsilon_r - p_j}\right)^{r_j}$$

where $\varepsilon_w^*$ is frequency dependent complex brine permittivity;
$\varepsilon_r^*$ is frequency dependent complex rock permittivity;
$p_j$ and $r_j$ are poles and residues of a rational function; and
n is an integer of 3 or more.

4. The method of claim 1, wherein:
the wideband model is based on a mixing model including charged spheroidal grains and non-charged spherical grains, and/or the wideband model is based on a mixing model which includes a hydrocarbon phase by lumping it with the matrix phase into a single "non-conductive" phase using a mixing law or by including it as a separate phase in the formation model.

5. The method of claim 1, wherein:
the inversion employs a wideband model that permits a distribution of grain sizes of the rock sample, or the inversion employs a wideband model that permits a single grain size of the rock sample.

6. The method of claim 1, wherein:
the plurality of parameters includes cation exchange capacity and a grain size indicator.

7. The method of claim 1, wherein:
said plurality of parameters of the rock sample are selected from the group consisting of: cation exchange capacity, a grain size indicator, water salinity, water saturation, water-filled porosity, cementation exponent, apparent cementation exponent and combinations thereof.

8. The method of claim 7, wherein:
said plurality of parameters of the rock sample are further selected from the group consisting of: a volume fraction of spheroids (p) of the rock sample, and a parameter related to the aspect ratio of spheroids ($d_L$).

9. The method of claim 8, further comprising:
utilizing said p and said $d_L$ to determine a cementation exponent parameter of the rock sample.

10. The method of claim 1, wherein:
the inversion is based on at least one input selected from the group consisting of: temperature (T), pressure (P), total porosity ($\phi_t$), and a real part of the dielectric constant of the grain matrix ($\varepsilon_m$) of the rock sample.

11. The method of claim 1, wherein:
the inversion involves inverting the wideband electromagnetic response data utilizing a single wideband model.

12. The method of claim 11, wherein:
the inversion involves iteratively changing at least one input parameter to minimize a difference between a measured electromagnetic response of the rock sample and a predicted electromagnetic response of the rock sample as determined from the single wideband model.

13. A method of investigating a rock sample, comprising:
using electromagnetic equipment to perform electromagnetic measurements of the rock sample at frequencies that fall within a wideband of frequencies, wherein the wideband of frequencies includes a low frequency sub-band including at least one frequency less than 10 KHz that is sensitive to conductivity of the rock sample and a high frequency sub-band including at least one frequency greater than 10 MHz that is sensitive to the permittivity of the rock sample;
using a data processor to obtain wideband electromagnetic response data derived from the electromagnetic measurements of the rock sample and to perform an inversion of said wideband electromagnetic response data in order to determine values for a plurality of parameters of the rock sample, wherein the inversion involves inverting the wideband electromagnetic response data utilizing a single wideband model, wherein the inversion involves iteratively changing at least one input parameter to minimize a difference between a measured electromagnetic response of the rock sample and a predicted electromagnetic response of the rock sample as determined from the single wideband model, and wherein the difference between the measured electromagnetic response of the rock sample and the predicted electromagnetic response of the rock sample is determined by a cost function.

14. The method of claim 1, wherein:
the inversion involves jointly inverting the wideband electromagnetic response data utilizing a first model describing a high frequency response and a second model describing a low frequency response.

15. The method of claim 14, wherein:
at least one of the first model and the second model accounts for Maxwell-Garnett interfacial polarization related to rock texture; and/or
at least one of the first model and the second model accounts for electrochemical polarization effects.

16. The method of claim 14, wherein:
the jointly inverting involves simultaneous inversion for a set of common parameters in the first and second models.

17. The method of claim 14, wherein:
the jointly inverting involves sequential inversion with first inversion involving one of the first and second models and second inversion involving the other of the first and second models, wherein some or all outputs of the first inversion are used as inputs to the second inversion.

18. The method of claim 1, wherein:
the values for the plurality of parameters of the rock sample that are determined from the inversion characterize an invaded formation zone, and such values are used as inputs to another inversion of electromagnetic response data that determines values of parameters for an uninvaded formation zone.

19. The method of claim 1, wherein:
said rock sample is a geological formation traversed by a borehole and said electromagnetic equipment comprises at least one tool that is run in said borehole in order to investigate the geological formation in situ.

20. The method of claim 19, wherein:
said at least one tool performs electromagnetic measurements at different depth intervals of the borehole; and
the inversion is performed on wideband electromagnetic response data obtained for different depth intervals in order to determine values for a plurality of other parameters of the geological formation at the different depth intervals.

21. The method of claim 20, wherein:
said at least one tool is conveyed through the borehole by a conveyance mechanism selected from the group consisting of: a wireline cable, drill pipe, a tractor device, and a tool string that extends through a drill bit.

22. The method of claim 1, wherein:
the electromagnetic equipment comprises at least one laboratory apparatus.

23. A data processing system that characterizes a rock sample, comprising:
electromagnetic equipment which performs electromagnetic measurements of the rock sample at frequencies that fall within a wideband of frequencies, wherein the wideband of frequencies includes a low frequency sub-band including at least one frequency less than 10 KHz that is sensitive to conductivity of the rock sample, and a high frequency sub-band including at least one frequency greater than 10 MHz that is sensitive to the permittivity of the rock sample;
computer memory storing wideband electromagnetic response data obtained by the electromagnetic equipment; and
a processor configured to perform an inversion of said wideband electromagnetic response data stored by the computer memory in order to determine values for a plurality of parameters of the rock sample, wherein the inversion employs a wideband model that accounts for two different polarization mechanisms, including i) polarization on interfaces between conductive fluid and non-conductive mineral grains and/or non-conductive hydrocarbons, and ii) polarization of an electrical double layer present on charged mineral grains.

* * * * *